United States Patent
Roussel et al.

(10) Patent No.: US 11,390,628 B2
(45) Date of Patent: Jul. 19, 2022

(54) PREPARATION OF BUPRENORPHINE

(71) Applicants: RIVER STONE BIOTECH LLC, Cambridge, MA (US); Jimmy Van Wiltenburg, Groningen (NL); Marco Santella, København (DK)

(72) Inventors: Patrick Roussel, Reinach (CH); Jimmy Van Wiltenburg, Groningen (NL); Marco Santella, København (DK)

(73) Assignee: River Stone Biotech LLC, Cambridge, MA (US)

( * ) Notice: Subject to any disclaimer, the term of this patent is extended or adjusted under 35 U.S.C. 154(b) by 226 days.

(21) Appl. No.: 16/614,228

(22) PCT Filed: May 21, 2018

(86) PCT No.: PCT/IB2018/000732
§ 371 (c)(1),
(2) Date: Nov. 15, 2019

(87) PCT Pub. No.: WO2018/211331
PCT Pub. Date: Nov. 22, 2018

(65) Prior Publication Data
US 2021/0380597 A1 Dec. 9, 2021

Related U.S. Application Data

(60) Provisional application No. 62/508,616, filed on May 19, 2017.

(51) Int. Cl.
*C07D 489/12* (2006.01)

(52) U.S. Cl.
CPC ................... *C07D 489/12* (2013.01)

(58) Field of Classification Search
CPC ............................ C07D 489/12; C07D 489/02
USPC ........................................................ 546/39, 44
See application file for complete search history.

(56) References Cited

FOREIGN PATENT DOCUMENTS

| EP | 2 619 212 | 1/2016 |
| EP | 3 067 357 | 9/2016 |
| WO | 2008/048957 | 4/2008 |
| WO | 2010/121369 | 10/2010 |

OTHER PUBLICATIONS

The International Search Report (ISR) with Written Opinion for PCT/IB2018/000732 dated Oct. 30, 2018, pp. 1-16.
Werner, Lukas et al. "Synthesis of Buprenorphine from Oripavine via N-Demethylation of Oripavine Quaternary Salts" The Journal of Organic Chemistry (2011) vol. 76, pp. 4628-4634.
Maurer, Peter J. et al. "Nitrogen-Bridged Conformationally Constrained Etorphine Analogues. Synthesis and Biological Evaluation" J. Med. Chem. (1987) vol. 30, pp. 2016-2026.

*Primary Examiner* — Charanjit Aulakh
(74) *Attorney, Agent, or Firm* — McDonnell Boehnen Hulbert & Berghoff LLP

(57) ABSTRACT

Disclosed are methods for preparing buprenorphine from, for example, compounds such as nororipavine and northebaine.

17 Claims, No Drawings

PREPARATION OF BUPRENORPHINE

CROSS-REFERENCE TO RELATED APPLICATIONS

This application is a U.S. national phase of International Application No. PCT/IB2018/000732, filed May 21, 2018, which claims the benefit of priority of U.S. Provisional Patent Application No. 62/508,616, filed on May 19, 2017, the disclosures of which are incorporated herein by reference in their entireties.

BACKGROUND OF THE DISCLOSURE

Field of the Disclosure

This disclosure relates to methods for preparing buprenorphine. More particularly, the present disclosure relates to methods for preparing buprenorphine from oripavine, thebaine, and derivatives thereof, such as nor-compounds including nororipavine and northebaine.

Description of Related Art

Total synthesis of natural opiate compounds or semisynthetic opioids is complex and not commercially competitive (Rinner et al., *Top. Curr. Chem.* 309:33-66 (2012)). While natural opiates are obtained from plants, opioids are often obtained semi-synthetically using natural opiate precursors. Buprenorphine and other semisynthetic opioids are, or can be, made from thebaine, an opiate alkaloid (Hudlicky, *Can. J. Chem.* 93(5):492-501 (2015)). Thebaine is currently obtained by crop cultivation of and extraction from plants of the *Papaver* genus. Several possible methods to prepare buprenorphine have been reported from thebaine. A known and likely commercial route to buprenorphine is made up of 6 major steps, starting from thebaine. (Machara et al., *Adv. Synth. Catal.* 354(4):613-26 (2012); Werner et al., *J. Org. Chem.* 76(11):4628-34 (2011)). The first 3 steps are a Diels-Alder reaction of thebaine with methyl vinyl ketone to form a 4+2 product, hydrogenation of the carbon-carbon double bond of the resultant product, and addition of a tertiary butyl group via a Grignard reaction. The final steps are N- and O-demethylation and cyclopropyl alkylation. The number of steps can increase to 8, if the N- and O-demethylation and N-alkylation steps are performed in 2 stages, rather than 1. The order of the hydrogenation and Grignard steps may be reversed but most, if not all, economically viable preparations include the 3 above-mentioned steps prior to the N-demethylation step. One challenge of this known preparation of buprenorphine is the exchange of the N-methyl group for an N-cyclopropyl group. N-demethylation methods can involve highly toxic reagents such as cyanogen bromide (von Braun, *J. Chem. Ber.*, 33:1438-1452 (1900)) and chloroformate reagents (Cooley et al., *Synthesis*, 1:1-7 (1989); Olofson et al., *J. Org. Chem.*, 49:2081-2082 (1984)) or may proceed in low yield, for example, by producing N-oxide intermediates (Polonovski reaction: Kok et al., *Adv Synth. Catal.*, 351:283-286 (2009); Dong et al., *J. Org. Chem.*, 72:9881-9885 (2007)). These methods generate significant amounts of toxic waste. The harsh conditions used for demethylation (e.g., strong bases and high temperatures) generate a significant amount of impurities, requiring additional purification and lowering yields. Attempts to reduce impurities and improve yields have been made by avoiding the O-demethylation step, by using oripavine as starting material, but a principal obstacle to an efficient synthesis remains the N-demethylation step.

Accordingly, there remains a need for an improved route to buprenorphine, such as a route that is shorter, more efficient (due to, e.g., improved total yield, decreased impurities), and/or produces less toxic waste.

SUMMARY OF THE DISCLOSURE

One aspect of the disclosure relates to a method of preparing buprenorphine, or a salt thereof, from Compound HO-I-H, or a salt thereof:

(Compound HO-I-H)

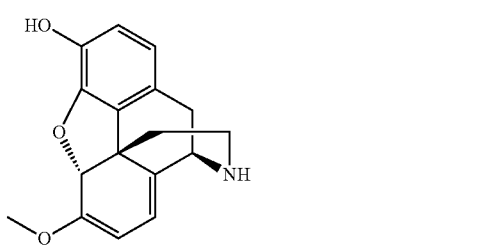

comprising:
(i)(A1) reacting Compound HO-I-H with cyclopropane carboxaldehyde followed by a hydride source; or
(i)(A2) reacting Compound HO-I-H with cyclopropanecarboxylic acid halide followed by a reducing agent; or
(i)(A3) reacting Compound HO-I-H with cyclopropylmethyl halide or activated cyclopropane methanol;
to provide Compound HO-I-MCP:

(Compound HO-I-MCP)

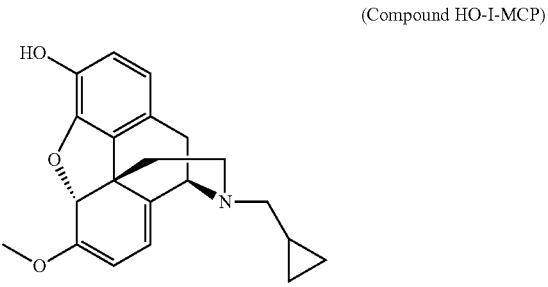 [SMILES: COC1=CC=C2[C@H]3Cc4ccc(O)c5c4[C@@]2(CCN3CC2CC2)[C@H]1O5]

(ii)(B) reacting Compound HO-I-MCP with methyl vinyl ketone to provide Compound HO-II-MCP:

(Compound HO-II-MCP)

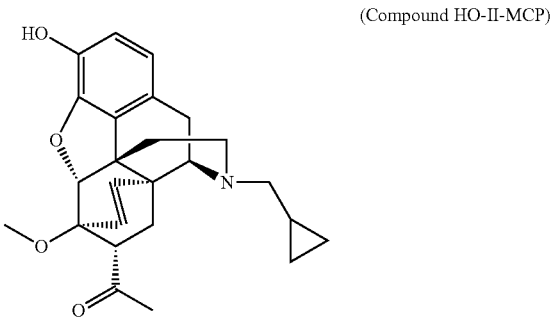 [SMILES: CO[C@]12C=C[C@@]3(C[C@@H]1C(C)=O)[C@H]1Cc4ccc(O)c5c4[C@@]3(CCN1CC1CC1)[C@H]2O5]

(iii)(C) reacting Compound HO-II-MCP with H$_2$ in the presence of a hydrogenation catalyst to provide Compound HO-IIIB-MCP:

(Compound HO-IIIB-MCP)

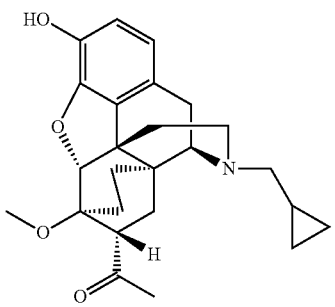

(iv)(D) reacting Compound HO-IIIB-MCP with tert-butylmagnesium halide to provide buprenorphine.

Another aspect of the disclosure relates to a method of preparing buprenorphine, or a salt thereof, from Compound HO-I-H, or a salt thereof:

(Compound HO-I-H)

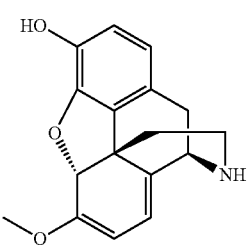

comprising:
(i)(A1) reacting Compound HO-I-H with cyclopropane carboxaldehyde followed by a hydride source; or
(i)(A2) reacting Compound HO-I-H with cyclopropanecarboxylic acid halide followed by a reducing agent; or
(i)(A3) reacting Compound HO-I-H with cyclopropylmethyl halide or activated cyclopropane methanol;
to provide Compound HO-I-MCP:

(Compound HO-I-MCP)

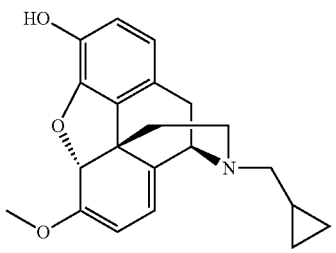

(ii)(B) reacting Compound HO-I-MCP with methyl vinyl ketone to provide Compound HO-II-MCP:

(Compound HO-II-MCP)

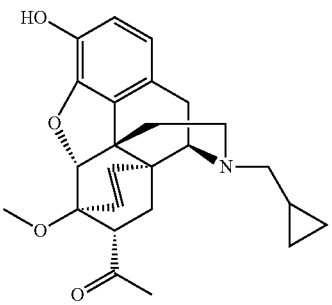

(iii)(D) reacting Compound HO-II-MCP with tert-butylmagnesium halide to provide Compound HO-IIIA-MCP:

(Compound HO-IIIA-MCP)

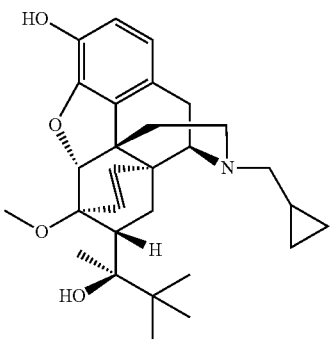

(iv)(C) reacting Compound HO-IIIA-MCP with H$_2$ in the presence of a hydrogenation catalyst to provide buprenorphine.

Another aspect of the disclosure relates to a method of preparing buprenorphine, or a salt thereof, from Compound BnO-I-H, or a salt thereof:

(Compound BnO-I-H)

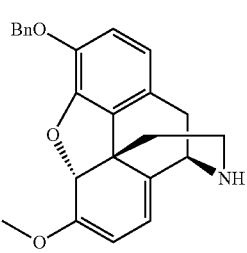

comprising:
(i)(A1) reacting Compound BnO-I-H with cyclopropane carboxaldehyde followed by a hydride source; or
(i)(A2) reacting Compound BnO-I-H with cyclopropanecarboxylic acid halide followed by a reducing agent; or
(i)(A3) reacting Compound BnO-I-H with cyclopropylmethyl halide or activated cyclopropane methanol;

to provide Compound BnO-I-MCP:

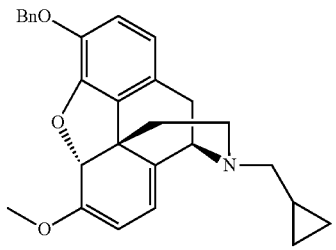
(Compound BnO-I-MCP)

(ii)(B) reacting Compound BnO-I-MCP with methyl vinyl ketone to provide Compound BnO-II-MCP:

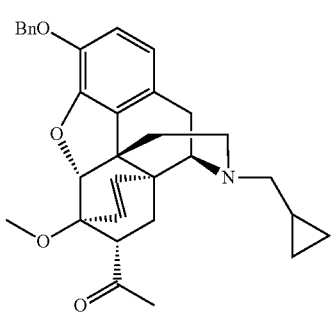
(Compound BnO-II-MCP)

(iii)(D) reacting Compound BnO-II-MCP with tert-butyl-magnesium halide to provide Compound BnO-IIIA-MCP:

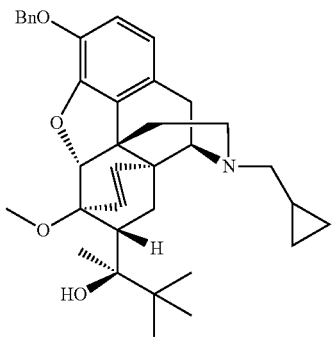
(Compound BnO-IIIA-MCP)

(iv)(C) reacting Compound BnO-IIIA-MCP with $H_2$ in the presence of a hydrogenation catalyst to provide buprenorphine.

Another aspect of the disclosure relates to a method of preparing buprenorphine, or a salt thereof, from Compound MeO-I-H, or a salt thereof:

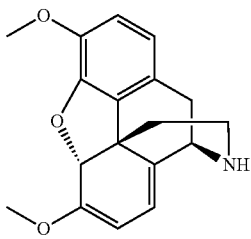
(Compound MeO-I-H)

comprising:

(i)(A1) reacting Compound MeO-I-H with cyclopropane carboxaldehyde followed by a hydride source; or (i)(A2) reacting Compound MeO-I-H with cyclopropanecarboxylic acid halide followed by a reducing agent; or (i)(A3) reacting Compound MeO-I-H with cyclopropylmethyl halide or activated cyclopropane methanol;

to provide Compound MeO-I-MCP:

(Compound MeO-I-MCP)

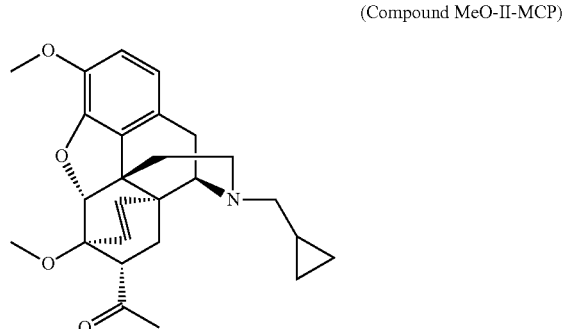

(ii)(B) reacting Compound MeO-I-MCP with methyl vinyl ketone to provide Compound MeO-II-MCP:

(Compound MeO-II-MCP)

(iii)(C) reacting Compound MeO-II-MCP with $H_2$ in the presence of a hydrogenation catalyst to provide Compound MeO-IIIB-MCP:

(Compound MeO-IIIB-MCP)

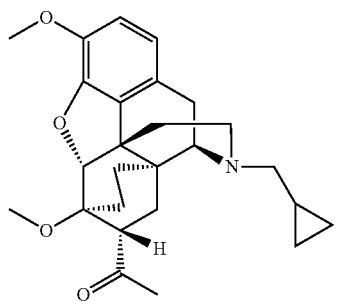

(iv)(D) reacting Compound MeO-IIIB-MCP with tert-butylmagnesium halide to provide Compound MeO-IV-MCP:

(Compound MeO-IV-MCP)

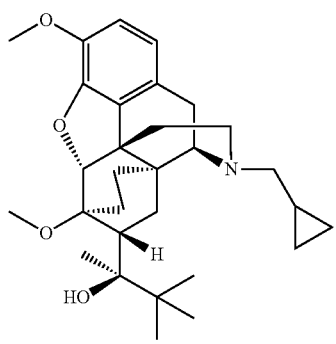

(v)(E) reacting a compound of Compound MeO-IV-MCP with a demethylating agent to provide buprenorphine.

Another aspect of the disclosure relates to a method of preparing buprenorphine, or a salt thereof, from Compound MeO-I-H, or a salt thereof:

(Compound MeO-I-H)

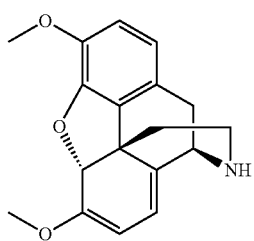

comprising:

(i)(A1) reacting Compound MeO-I-H with cyclopropane carboxaldehyde followed by a hydride source; or (i)(A2) reacting Compound MeO-I-H with cyclopropanecarboxylic acid halide followed by a reducing agent; or (i)(A3) reacting Compound MeO-I-H with cyclopropylmethyl halide or activated cyclopropane methanol;

to provide Compound MeO-I-MCP:

(Compound MeO-I-MCP)

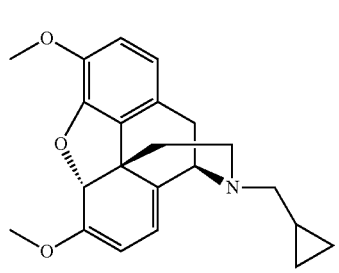

(ii)(B) reacting Compound MeO-I-MCP with methyl vinyl ketone to provide Compound MeO-II-MCP:

(Compound MeO-II-MCP)

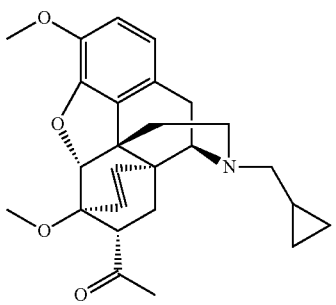

(iii)(D) reacting Compound MeO-II-MCP with tert-butylmagnesium halide to provide Compound MeO-IIIA-MCP:

(Compound MeO-IIIA-MCP)

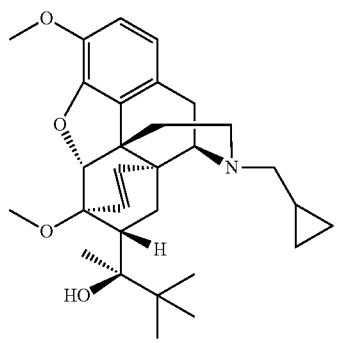

(iv)(C) reacting Compound MeO-IIIA-MCP with $H_2$ in the presence of a hydrogenation catalyst to provide a compound of Compound MeO-IV-MCP:

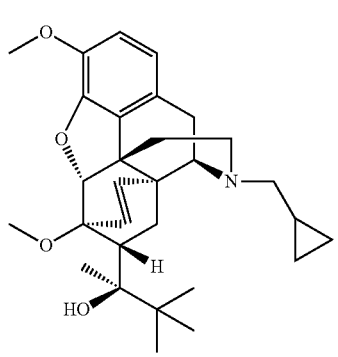
(Compound MeO-IV-MCP)

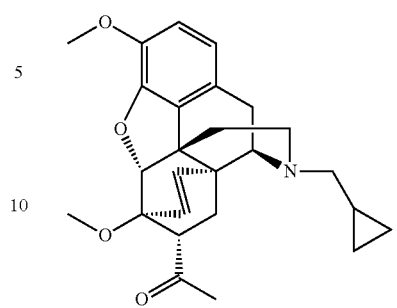
(Compound MeO-II-MCP)

(v)(E) reacting a compound of Compound MeO-IV-MCP with a demethylating agent to provide buprenorphine.

Another aspect of the disclosure relates to a method of preparing buprenorphine, or a salt thereof, from Compound MeO-I-H, or a salt thereof:

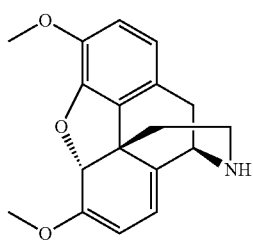
(Compound MeO-I-H)

comprising:

(i)(A1) reacting Compound MeO-I-H with cyclopropane carboxaldehyde followed by a hydride source; or (i)(A2) reacting Compound MeO-I-H with cyclopropanecarboxylic acid halide followed by a reducing agent; or (i)(A3) reacting Compound MeO-I-H with cyclopropylmethyl halide or activated cyclopropane methanol;

to provide Compound MeO-I-MCP:

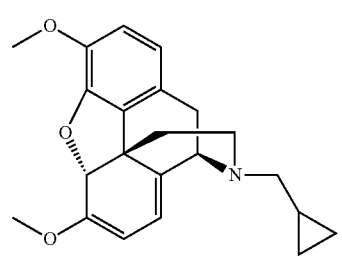
(Compound MeO-I-MCP)

(ii)(B) reacting Compound MeO-I-MCP with methyl vinyl ketone to provide Compound MeO-II-MCP:

(iii)(D) reacting Compound MeO-II-MCP with tert-butyl-magnesium halide to provide Compound MeO-IIIA-MCP:

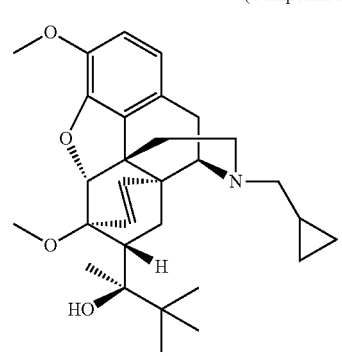
(Compound MeO-IIIA-MCP)

(iv)(E) reacting Compound MeO-IIIA-MCP with a demethylating agent to provide Compound HO-IIIA-MCP:

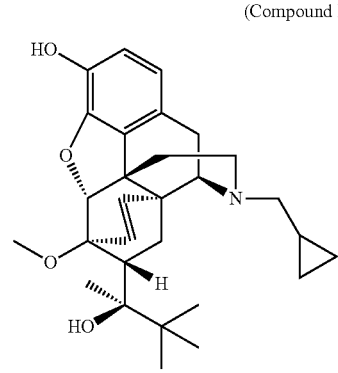
(Compound MeO-IIIA-MCP)

(v)(C) reacting Compound HO-IIIA-MCP with $H_2$ in the presence of a hydrogenation catalyst to provide buprenorphine.

Another aspect of the disclosure relates to a method of preparing buprenorphine, or a salt thereof, from Compound HO-I-Me, or a salt thereof:

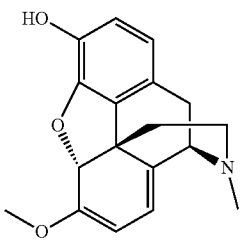
(Compound HO-I-Me)

comprising:
(i)(F) reacting Compound HO-I-Me with benzyl halide, benzyl sulfonate, or activated benzyl alcohol to provide Compound BnO-I-Me:

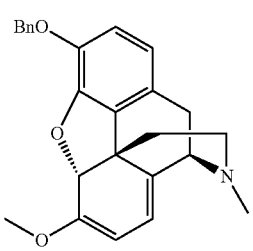
(Compound BnO-I-Me)

(ii)(E) reacting Compound BnO-I-Me with an azodicarboxylate followed by an acid or an addition salt thereof to provide Compound BnO-I-H:

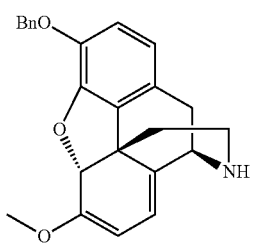
(Compound BnO-I-H)

(iii)(A1) reacting Compound BnO-I-H with cyclopropane carboxaldehyde followed by a hydride source; or
(iii)(A2) reacting Compound BnO-I-H with cyclopropanecarboxylic acid halide followed by a reducing agent; or
(iii)(A3) reacting Compound BnO-I-H with cyclopropylmethyl halide or activated cyclopropane methanol;
to provide Compound BnO-I-MCP:

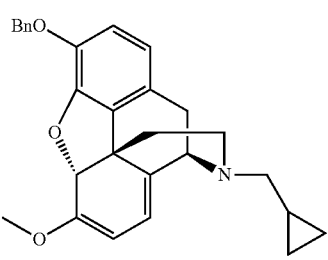
(Compound BnO-I-MCP)

(iv)(B) reacting Compound BnO-I-MCP with methyl vinyl ketone to provide Compound BnO-II-MCP:

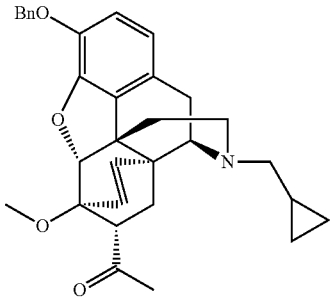
(Compound BnO-II-MCP)

(v)(D) reacting Compound BnO-II-MCP with tert-butylmagnesium halide to provide Compound BnO-IIIA-MCP:

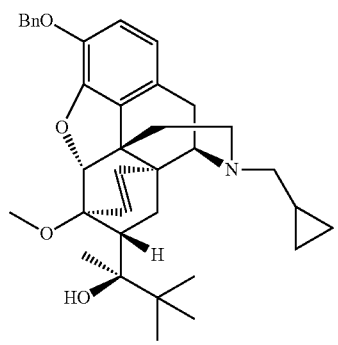
(Compound BnO-IIIA-MCP)

(vi)(C) reacting Compound BnO-IIIA-MCP with $H_2$ in the presence of a hydrogenation catalyst to provide buprenorphine.

Another aspect of the disclosure relates to a method of preparing buprenorphine, or a salt thereof, from Compound HO-I-H, or a salt thereof:

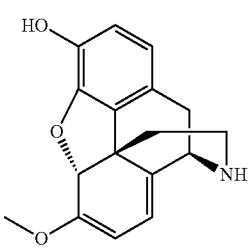
(Compound HO-I-H)

comprising:
(i)(A1) reacting Compound HO-I-H with cyclopropane carboxaldehyde followed by a hydride source; or
(i)(A2) reacting Compound HO-I-H with cyclopropanecarboxylic acid halide followed by a reducing agent; or
(i)(A3) reacting Compound HO-I-H with cyclopropylmethyl halide or activated cyclopropane methanol;

to provide Compound HO-I-MCP:

(Compound HO-I-MCP)

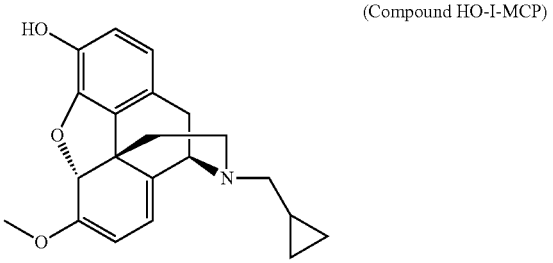 [SMILES: COC1=CC=C2[C@H]3Cc4ccc(O)c5c4[C@@]2(CCN3CC2CC2)[C@H]1O5]

(ii)(B) reacting Compound HO-I-MCP with methyl vinyl ketone to provide Compound HO-II-MCP:

(Compound HO-II-MCP)

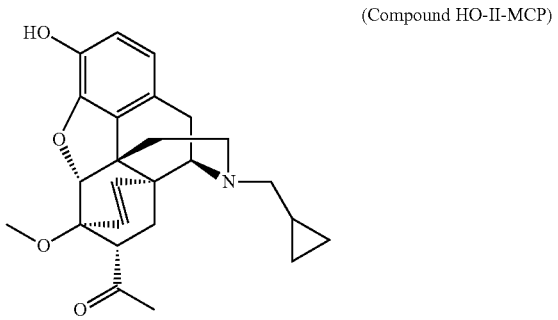 [SMILES: CO[C@]12C=C[C@@]3(C[C@@H]1C(C)=O)[C@H]1Cc4ccc(O)c5c4[C@@]3(CCN1CC1CC1)[C@H]2O5]

(iii)(F) reacting Compound HO-II-MCP with benzyl halide, benzyl sulfonate, or activated benzyl alcohol to provide Compound BnO-II-MCP:

(Compound BnO-II-MCP)

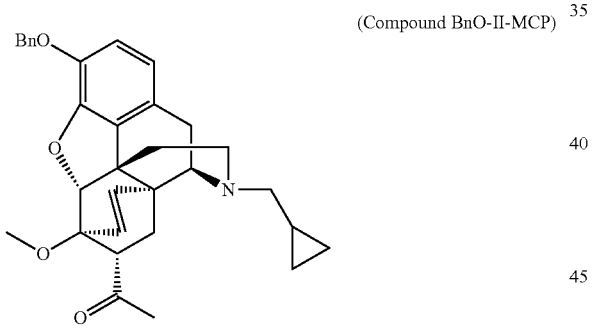

(iv)(D) reacting Compound BnO-II-MCP with tert-butyl-magnesium halide to provide Compound BnO-IIIA-MCP:

(Compound BnO-IIIA-MCP)

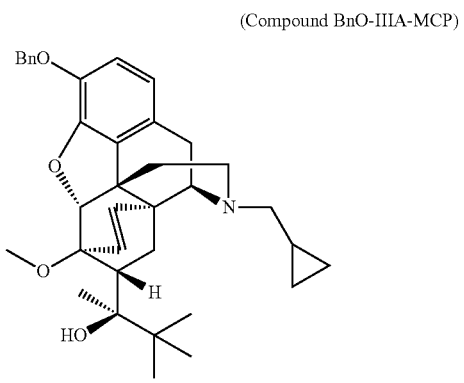 [SMILES: CO[C@]12C=C[C@@]3(C[C@@H]1[C@](C)(O)C(C)(C)C)[C@H]1Cc4ccc(OCc5ccccc5)c5c4[C@@]3(CCN1CC1CC1)[C@H]2O5]

(v)(C) reacting Compound BnO-IIIA-MCP with $H_2$ in the presence of a hydrogenation catalyst to provide buprenorphine.

Another aspect of the disclosure relates to a method of preparing buprenorphine, or a salt thereof, from Compound HO-I-H, or a salt thereof:

(Compound HO-I-H)

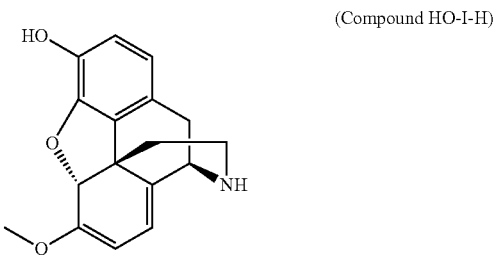 [SMILES: COC1=CC=C2[C@H]3Cc4ccc(O)c5c4[C@@]2(CCN3)[C@H]1O5]

comprising:

(i)(A1) reacting Compound HO-I-H with cyclopropane carboxaldehyde followed by a hydride source; or (i)(A2) reacting Compound HO-I-H with cyclopropanecarboxylic acid halide followed by a reducing agent; or (i)(A3) reacting Compound HO-I-H with cyclopropylmethyl halide or activated cyclopropane methanol;

to provide Compound HO-I-MCP:

(Compound HO-I-MCP)

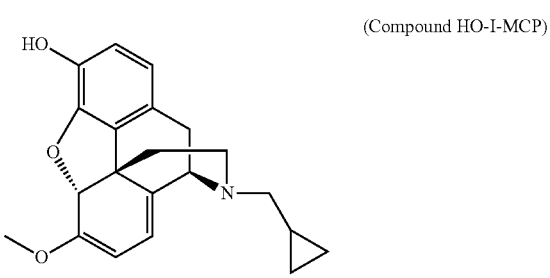 [SMILES: COC1=CC=C2[C@H]3Cc4ccc(O)c5c4[C@@]2(CCN3CC2CC2)[C@H]1O5]

(ii)(F) reacting Compound HO-I-MCP with benzyl halide, benzyl sulfonate, or activated benzyl alcohol to provide Compound BnO-I-MCP:

(Compound BnO-I-MCP)

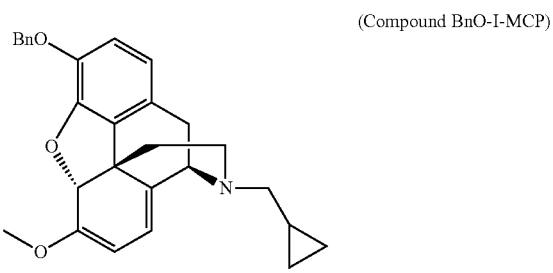 [SMILES: COC1=CC=C2[C@H]3Cc4ccc(OCc5ccccc5)c5c4[C@@]2(CCN3CC2CC2)[C@H]1O5]

(iii)(B) reacting Compound BnO-I-MCP with methyl vinyl ketone to provide Compound BnO-II-MCP:

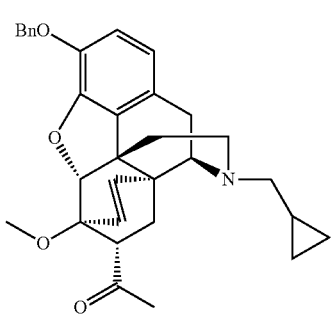
(Compound BnO-II-MCP)

(iv)(D) reacting Compound BnO-II-MCP with tert-butyl-magnesium halide to provide Compound BnO-IIIA-MCP:

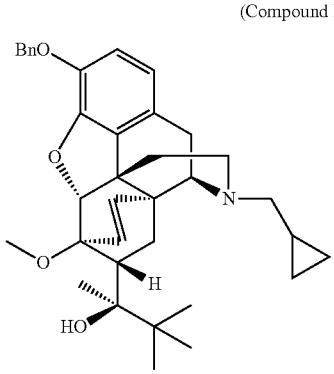
(Compound BnO-IIIA-MCP)

(v)(C) reacting Compound BnO-IIIA-MCP with $H_2$ in the presence of a hydrogenation catalyst to provide buprenorphine.

Another aspect of the disclosure relates to a method of preparing buprenorphine, or a salt thereof, from Compound HO-I-H, or a salt thereof:

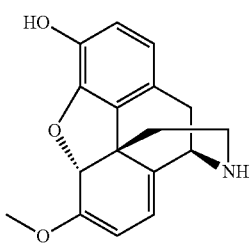
(Compound HO-I-H)

comprising:

(i)(F) reacting Compound HO-I-H with benzyl halide, benzyl sulfonate, or activated benzyl alcohol to provide Compound BnO-I-Bn:

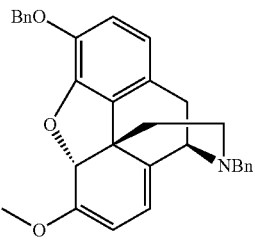
(Compound BnO-I-Bn)

(ii)(B) reacting Compound BnO-I-Bn with methyl vinyl ketone to provide Compound BnO-II-Bn:

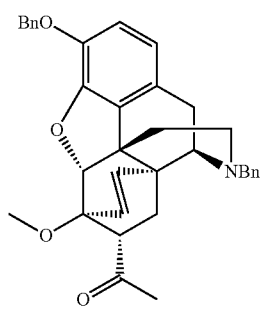
(Compound BnO-II-Bn)

(iii)(D) reacting Compound BnO-II-Bn with tert-butyl-magnesium halide to provide Compound BnO-IIIA-Bn:

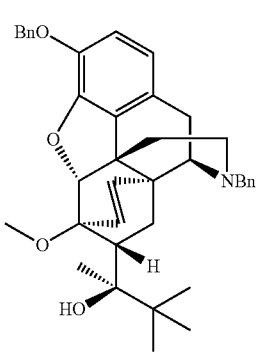
(Compound BnO-IIIA-Bn)

(iv)(C) reacting Compound BnO-IIIA-Bn with $H_2$ in the presence of a hydrogenation catalyst to provide a compound of Compound HO-IV-H:

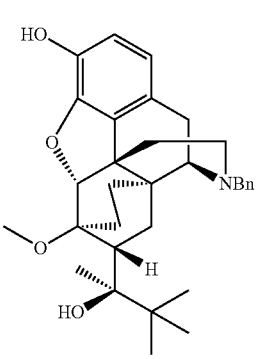
(Compound HO-IV-H)

(v)(A1) reacting Compound HO-IV-H with cyclopropane carboxaldehyde followed by a hydride source; or (v)(A2) reacting Compound HO-IV-H with cyclopropanecarboxylic acid halide followed by a reducing agent; or (v)(A3) reacting Compound HO-IV-H with cyclopropylmethyl halide or activated cyclopropane methanol;

to provide buprenorphine.

Another aspect of the disclosure relates to a method of preparing buprenorphine, or a salt thereof, from Compound HO-I-H, or a salt thereof:

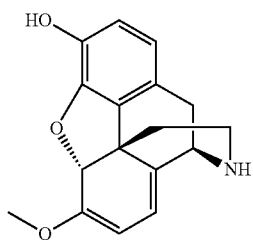
(Compound HO-I-H)

comprising:

(i)(G) reacting Compound HO-I-H with optionally substituted benzoyl halide to provide Compound HO-I-Ac:

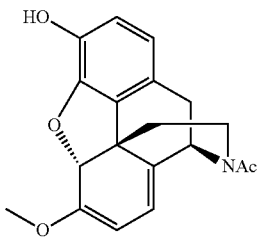
(Compound HO-I-Ac)

(ii)(F) reacting Compound HO-I-Ac with benzyl halide, benzyl sulfonate, or activated benzyl alcohol to provide Compound BnO-I-Ac:

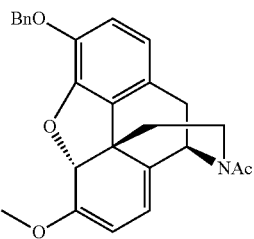
(Compound BnO-I-Ac)

(iii)(H) reacting Compound BnO-I-Ac with lithium aluminum hydride to provide Compound BnO-I-Bn:

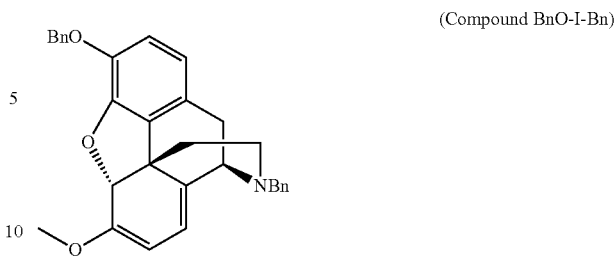
(Compound BnO-I-Bn)

(iv)(B) reacting Compound BnO-I-Bn with methyl vinyl ketone to provide Compound BnO-II-Bn:

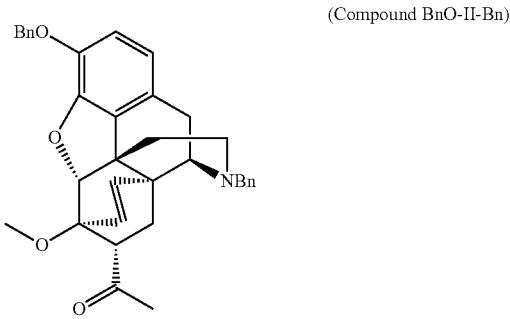
(Compound BnO-II-Bn)

(v)(D) reacting Compound BnO-II-Bn with tert-butylmagnesium halide to provide Compound BnO-IIIA-Bn:

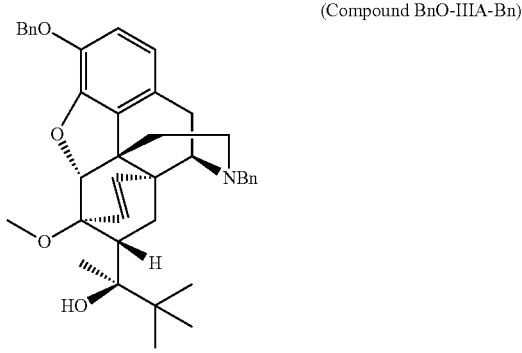 [SMILES: CO[C@]12C=C[C@@]3(C[C@@H]1[C@](C)(O)C(C)(C)C)[C@H]1Cc4ccc(OCc5ccccc5)c5c4[C@@]3(CCN1Cc1ccccc1)[C@H]2O5]
(Compound BnO-IIIA-Bn)

(vi)(C) reacting Compound BnO-IIIA-Bn with H$_2$ in the presence of a hydrogenation catalyst to provide a compound of Compound HO-IV-H:

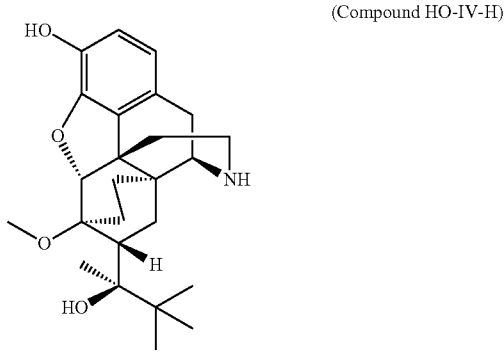 [SMILES: CO[C@]12CC[C@@]3(C[C@@H]1[C@](C)(O)C(C)(C)C)[C@H]1Cc4ccc(O)c5c4[C@@]3(CCN1)[C@H]2O5]
(Compound HO-IV-H)

(vii)(A1) reacting Compound HO-IV-H with cyclopropane carboxaldehyde followed by a hydride source; or (vii)(A2) reacting Compound HO-IV-H with cyclopropanecarboxylic acid halide followed by a reducing agent; or (vii)(A3) reacting Compound HO-IV-H with cyclopropylmethyl halide or activated cyclopropane methanol;

to provide buprenorphine.

Another aspect of the disclosure relates to a method of preparing buprenorphine, or a salt thereof, from Compound HO-I-H, or a salt thereof:

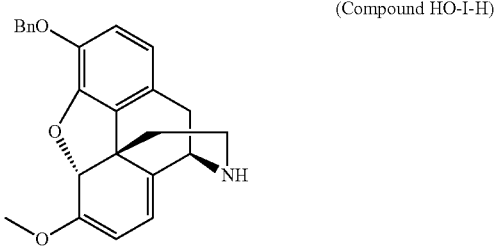 [SMILES: COC1=CC=C2[C@H]3Cc4ccc(OCc5ccccc5)c5c4[C@@]2(CCN3)[C@H]1O5]

(Compound HO-I-H)

comprising:

(i)(G) reacting Compound HO-I-H with optionally substituted benzoyl halide to provide Compound AcO-I-Ac:

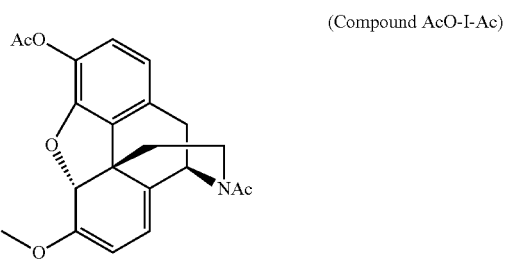

(Compound AcO-I-Ac)

(ii)(B) reacting Compound AcO-I-Ac with methyl vinyl ketone to provide Compound AcO-II-Ac:

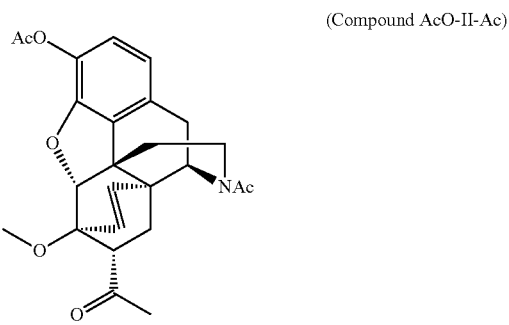

(Compound AcO-II-Ac)

(iii)(D) reacting Compound AcO-II-Ac with tert-butylmagnesium halide to provide Compound HO-IIIA-Ac:

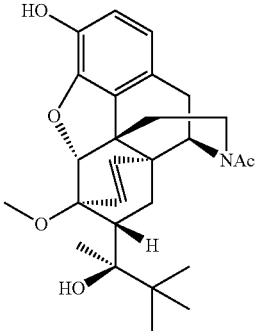

(Compound HO-IIIA-Ac)

(iv)(H) reacting Compound HO-IIIA-Ac with lithium aluminum hydride to provide Compound HO-IIIA-Bn:

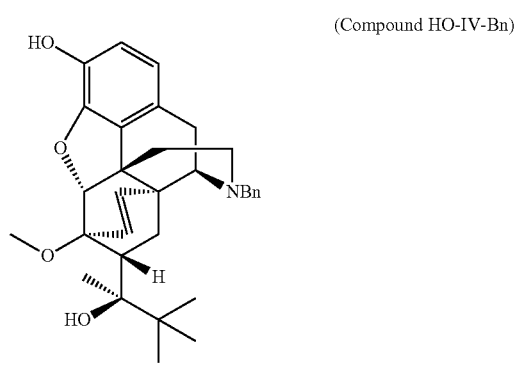 [SMILES: CO[C@]12C=C[C@@]3(C[C@@H]1[C@](C)(O)C(C)(C)C)[C@H]1Cc4ccc(O)c5c4[C@@]3(CCN1Cc1ccccc1)[C@H]2O5]

(Compound HO-IV-Bn)

(v)(C) reacting Compound HO-IV-Bn with H₂ in the presence of a hydrogenation catalyst to provide a compound of Compound HO-IV-H:

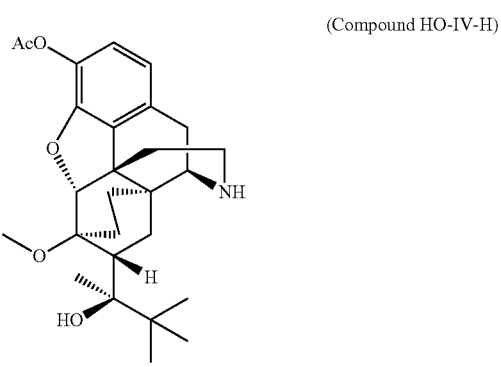 [SMILES: CO[C@]12CC[C@@]3(C[C@@H]1[C@](C)(O)C(C)(C)C)[C@H]1Cc4ccc(OC(C)=O)c5c4[C@@]3(CCN1)[C@H]2O5]

(Compound HO-IV-H)

(vi)(A1) reacting Compound HO-IV-H with cyclopropane carboxaldehyde followed by a hydride source; or (vi)(A2) reacting Compound HO-IV-H with cyclopropanecarboxylic acid halide followed by a reducing agent; or (vi)(A3) reacting Compound HO-IV-H with cyclopropylmethyl halide or activated cyclopropane methanol;

to provide buprenorphine.

Another aspect of the disclosure relates to a method of preparing buprenorphine, or a salt thereof, from Compound HO-I-H, or a salt thereof:

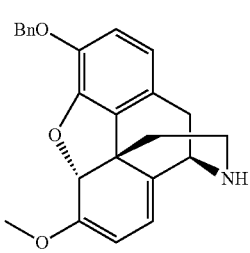
(Compound HO-I-H)

comprising:
(i)(G) reacting Compound HO-I-H with acyl halide to provide Compound AcO-I-Ac:

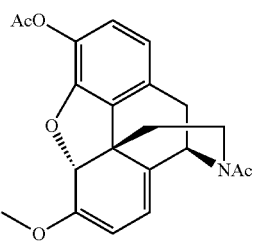
(Compound AcO-I-Ac)

(ii)(B) reacting Compound AcO-I-Ac with methyl vinyl ketone to provide Compound AcO-II-Ac:

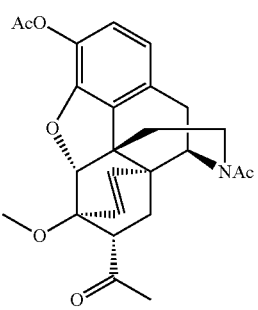
(Compound AcO-II-Ac)

(iii)(D) reacting Compound AcO-II-Ac with tert-butyl-magnesium halide to provide Compound HO-IIIA-Bn:

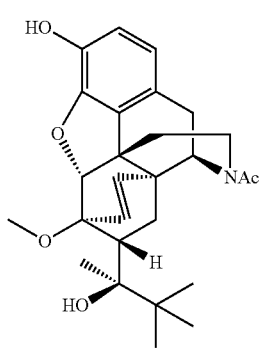
(Compound HO-IIIA-Ac)

(iv)(C) reacting Compound HO-IIIA-Ac with H₂ in the presence of a hydrogenation catalyst to provide a compound of Compound HO-IV-Ac:

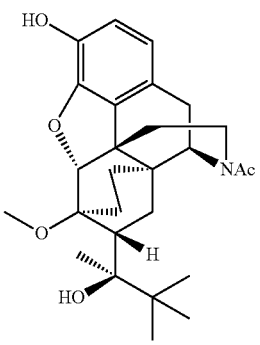
(Compound HO-IV-Ac)

(v)(I) reacting Compound HO-IV-Ac with Schwartz's reagent or base to provide Compound HO-IV-H:

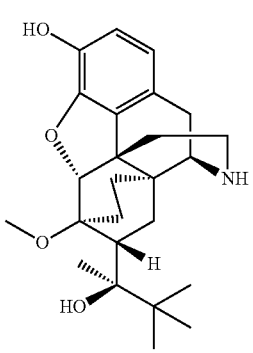
(Compound HO-IV-H)

(vi)(A1) reacting Compound HO-IV-H with cyclopropane carboxaldehyde followed by a hydride source; or (vi)(A2) reacting Compound HO-IV-H with cyclopropanecarboxylic acid halide followed by a reducing agent; or (vi)(A3) reacting Compound HO-IV-H with cyclopropylmethyl halide or activated cyclopropane methanol;

to provide buprenorphine.

Another aspect of the disclosure relates to a method of preparing buprenorphine, or a salt thereof, from Compound HO-I-H, or a salt thereof:

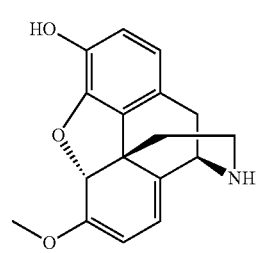
(Compound HO-I-H)

comprising:
(i)(G) reacting Compound HO-I-H with optionally substituted benzoyl halide to provide Compound AcO-I-Ac:

(Compound AcO-I-Ac)

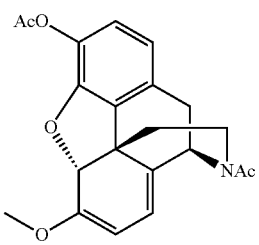

(ii)(B) reacting Compound AcO-I-Ac with methyl vinyl ketone to provide Compound AcO-II-Ac:

(Compound AcO-II-Ac)

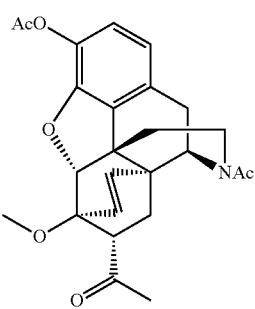

(iii)(C) reacting Compound HO-IIIA-Ac with $H_2$ in the presence of a hydrogenation catalyst to provide a compound of Compound AcO-IIIB-Ac:

(Compound AcO-IIIB-Ac)

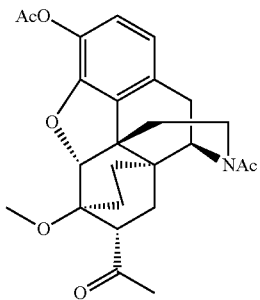

(iv)(D) reacting Compound AcO-II-Ac with tert-butyl-magnesium halide to provide Compound HO-IV-Ac:

(Compound HO-IV-Ac)

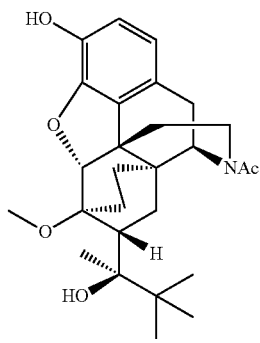

(v)(I) reacting Compound HO-IV-Ac with Schwartz's reagent or base to provide Compound HO-IV-H:

(Compound HO-IV-H)

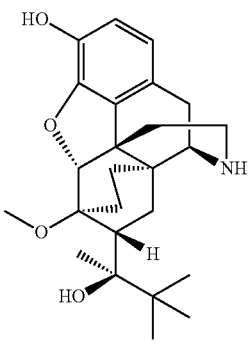

(vi)(A1) reacting Compound HO-IV-H with cyclopropane carboxaldehyde followed by a hydride source; or (vi)(A2) reacting Compound HO-IV-H with cyclopropanecarboxylic acid halide followed by a reducing agent; or (vi)(A3) reacting Compound HO-IV-H with cyclopropylmethyl halide or activated cyclopropane methanol;

to provide buprenorphine.

Another aspect of the disclosure relates to a compound of Formula I-Ac:

Formula I-Ac

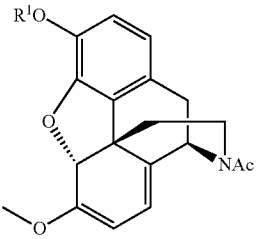

wherein Ac is optionally substituted benzoyl; and $R^1$ is H, Bn, or optionally substituted benzoyl.

Another aspect of the disclosure relates to a compound of Formula II-Ac:

Formula II-Ac

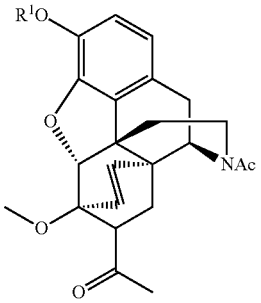

wherein Ac and $R^1$ are each independently optionally substituted benzoyl.

Another aspect of the disclosure relates to a compound of Formula IIIA-Ac:

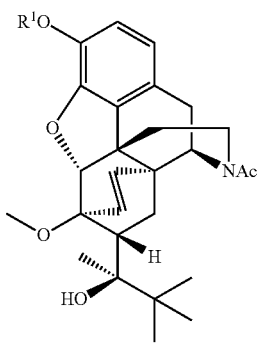

Formula IIIA-Ac wherein Ac is optionally substituted benzoyl, and $R^1$ is H.

Another aspect of the disclosure relates to a compound of Formula IIIA-Bn:

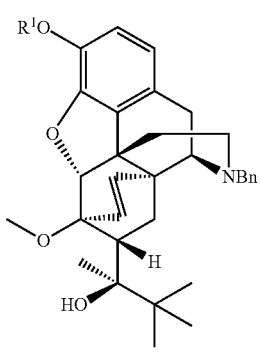

Formula IIIA-Bn wherein $R^1$ is H or Bn.

Aspects and embodiments of the disclosure related to methods of preparing buprenorphine from Compound MeO-I-H, BnO-I-H, or HO-I-H provide improved routes to buprenorphine that can be shorter, more efficient, and/or produce less toxic waste than, e.g., current commercial routes to buprenorphine. As a result, these aspects and embodiments can be well-suited for commercial (e.g., kg-scale) production of buprenorphine. Further, in certain aspects and embodiments, the synthetic routes disclosed herein advantageously avoid the harsh conditions and/or toxic byproducts of an N-demethylation step and can accordingly be particularly well-suited for producing buprenorphine on a commercial, e.g., kg, scale.

DETAILED DESCRIPTION

The particulars shown herein are by way of example and for purposes of illustrative discussion of the preferred embodiments of the invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range.

All percentages, ratios and proportions herein are by weight, unless otherwise specified. A weight percent (weight %, also as wt. %) of a component, unless specifically stated to the contrary, is based on the total weight of the composition in which the component is included (e.g., on the total amount of the reaction mixture).

Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Several embodiments of this invention are described herein. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All patents and printed publications are individually incorporated herein by reference in their entirety.

Terms used herein may be preceded and/or followed by a single dash, "—", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" with reference to the chemical structure referred to unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as —B-$(A)_a$, wherein a is 0 or 1. In such instances, when a is 0 the moiety is —B and when a is 1 the moiety is —B-A.

As used herein, the term "alkyl" includes a saturated hydrocarbon having a designed number of carbon atoms, such as 1 to 40 carbons (i.e., inclusive of 1 and 40), 1 to 35 carbons, 1 to 25 carbons, 1 to 20 carbons, or 1, 2, 3, 4, 5, 6, 7, 8, 9, 10, 11, 12, 13, 14, 15, 16, 17, or 18. Alkyl group may be straight or branched and depending on context, may be a monovalent radical or a divalent radical (i.e., an alkylene group). For example, the moiety "—($C_1$-$C_6$alkyl)-O—" signifies connection of an oxygen through an alkylene bridge having from 1 to 6 carbons and $C_1$-$C_3$alkyl represents methyl, ethyl, and propyl moieties. Examples of "alkyl" include, for example, methyl, ethyl, propyl, isopropyl, butyl, iso-, sec- and tert-butyl, pentyl, and hexyl.

The term "alkoxy" represents an alkyl group of indicated number of carbon atoms attached to the parent molecular moiety through an oxygen bridge. Examples of "alkoxy" include, for example, methoxy, ethoxy, propoxy, and isopropoxy.

The term "alkenyl" as used herein, unsaturated hydrocarbon containing from 2 to 10 carbons (i.e., inclusive of 2 and 10), 2 to 8 carbons, 2 to 6 carbons, or 2, 3, 4, 5 or 6, unless otherwise specified, and containing at least one carbon-carbon double bond. Alkenyl group may be straight or branched and depending on context, may be a monovalent radical or a divalent radical (i.e., an alkenylene group). For example, the moiety "—($C_2$-$C_6$ alkenyl)-O—" signifies connection of an oxygen through an alkenylene bridge having from 2 to 6 carbons. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkynyl" as used herein, unsaturated hydrocarbon containing from 2 to 10 carbons (i.e., inclusive of 2 and 10), 2 to 8 carbons, 2 to 6 carbons, or 2, 3, 4, 5 or 6 unless otherwise specified, and containing at least one carbon-carbon triple bond. Alkynyl group may be straight or branched and depending on context, may be a monovalent radical or a divalent radical (i.e., an alkynylene group). For example, the moiety "—($C_2$-$C_6$ alkynyl)-O—" signifies connection of an oxygen through an alkynylene bridge having from 2 to 6 carbons. Representative examples of alkynyl include, but are not limited to, acetylenyl, 1-propynyl, 2-propynyl, 3-butynyl, 2-pentynyl, and 1-butynyl.

The term "aryl" represents an aromatic ring system having a single ring (e.g., phenyl) which is optionally fused to other aromatic hydrocarbon rings or non-aromatic hydrocarbon or heterocyclic rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. "Aryl" also includes ring systems having a first carbocyclic, aromatic ring fused to a nonaromatic heterocycle, for example, 1H-2,3-dihydrobenzofuranyl and tetrahydroisoquinolinyl. The aryl groups herein are unsubstituted or, when specified as "optionally substituted", can unless stated otherwise be substituted in one or more substitutable positions with various groups as indicated.

The term "heteroaryl" refers to an aromatic ring system containing at least one aromatic heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic rings, for example, cycloalkyl or heterocycloalkyl rings, wherein the cycloalkyl and heterocycloalkyl rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, isoindolinyl, isobenzothienyl, benzoxazolyl, pyridopyridinyl, purinyl, benzodioxolyl, triazinyl, pteridinyl, benzothiazolyl, imidazopyridinyl, imidazothiazolyl, benzisoxazinyl, benzoxazinyl, benzopyranyl, benzothiopyranyl, chromonyl, chromanonyl, pyridinyl-N-oxide, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as indicated.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butyrolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as indicated.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups, as indicated.

The term "ring system" encompasses monocycles, as well as fused and/or bridged polycycles.

The terms "halogen" or "halo" indicate fluorine, chlorine, bromine, and iodine. In certain embodiments of each and every embodiment described herein, the term "halogen" or "halo" refers to fluorine or chlorine. In certain embodiments of each and every embodiment described herein, the term "halogen" or "halo" refers to fluorine.

The term "halide" indicates fluoride, chloride, bromide, and iodide. In certain embodiments of each and every embodiment described herein, the term "halide" refers to bromide or chloride.

The term "substituted," when used to modify a specified group or radical, means that one or more hydrogen atoms of the specified group or radical are each, independently of one another, replaced with the same or different substituent groups as defined below, unless specified otherwise.

Specific protecting groups may be used to protect reactive functionalities of a starting material or intermediate to prepare a desired product. In general, the need for such protecting groups as well as the conditions necessary to attach and remove such groups will be apparent to those skilled in the art of organic synthesis. An authoritative account describing the many alternatives to the trained practitioner are J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Chemical Synthesis of Buprenorphine

The disclosure relates to methods for preparing buprenorphine:

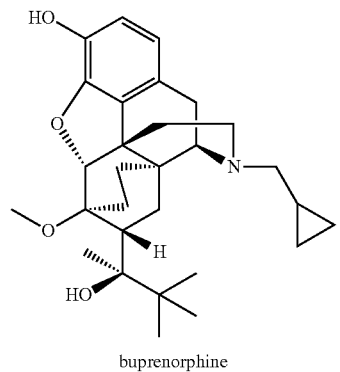 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

buprenorphine

In various aspects and embodiments, the methods comprise a series of reaction steps to prepare buprenorphine from a compound of Formula I-Me:

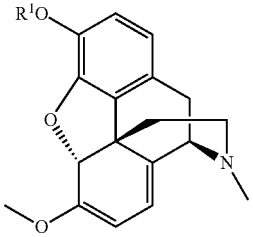

Formula I-Me wherein $R^1$ is H (Compound HO-I-Me; oripavine) or benzyl (Compound BnO-I-Me).

As used herein, the term "benzyl" ("Bn") includes unsubstituted (i.e., ($C_6H_5$)—$CH_2$—) and substituted benzyl (i.e., benzyl substituted at the 2-, 3-, and/or 4-position with $C_1$-$C_8$ alkyl or halide). The person of ordinary skill in the art will appreciate that oxygen protecting groups include alkoxycarbonyl, acyl, acetal, ether, ester, silyl ether, alkylsulfonyl, and arylsulfonyl. Exemplary oxygen protecting groups include allyl, triphenylmethyl (trityl or Tr), benzyl, methanesulfonyl, p-toluenesulfonyl, p-methoxybenzyl (PMB), p-methoxyphenyl (PMP), methoxymethyl (MOM), p-methoxyethoxymethyl (MEM), tetrahydropyranyl (THP), ethoxyethyl (EE), methylthiomethyl (MTM), 2-methoxy-2-propyl (MOP), 2-trimethylsilylethoxymethyl (SEM), benzoate (BZ), allyl carbonate, 2.2.2-trichloroethyl carbonate (Troc), 2-trimethylsilylethyl carbonate, trimethylsilyl (TMS), triethylsilyl (TES), triisopropylsilyl (TIPS), triphenylsilyl (TPS), t-butyldimethylsilyl (TBDMS), and t-butyldiphenylsilyl (TBDPS). A variety of protecting groups for the oxygen and the synthesis thereof may be found in "Protective Groups in Organic Synthesis" by T. W. Greene and P. G. M. Wuts, John Wiley & Sons, 1999. In certain embodiments, an appropriate oxygen protecting group may be used in place of benzyl.

In some embodiments, the methods comprise reacting a compound of Formula I-Me (e.g., Compound HO-I-Me) with benzyl halide, benzyl sulfonate, or activated benzyl alcohol to provide another compound of Formula I-Me (e.g., Compound BnO-I-Me). A preparation of Compound BnO-I-Me was described in International Patent Application Publications nos. WO 2008/048957 and WO 2013/168011.

In some embodiments, the methods comprise reacting a compound of Formula I-Me with an azodicarboxylate followed by an acid or an addition salt thereof to provide a compound of Formula I-H (see below), wherein $R^1$ is benzyl (Compound BnO-I-H). A preparation of Compound BnO-I-H was described in International Patent Application Publications nos. WO 2008/048957 and WO 2013/168011.

In various aspects and embodiments, the methods comprise a series of reaction steps to prepare buprenorphine from a compound of Formula I-H:

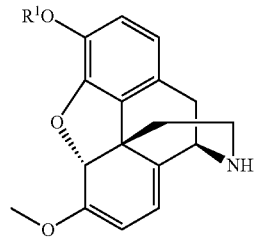

Formula I-H wherein R¹ is H (Compound HO-I-H; nororipavine), methyl (Compound MeO-I-H; northebaine), or benzyl ("Bn") (Compound BnO-I-H; benzyl-protected nororipavine). Such methods provide an improved route to buprenorphine that can be shorter, more efficient, and/or produce less toxic waste than, e.g., current commercial routes to buprenorphine. As a result, these aspects and embodiments can be well-suited for commercial (e.g., kg-scale) production of buprenorphine. Further, such methods advantageously avoid the harsh conditions and/or toxic byproducts of an N-demethylation step and can accordingly be particularly well-suited for producing buprenorphine on a commercial, e.g., kg, scale.

In some embodiments, the methods comprise reacting a compound of Formula I-H with cyclopropane carboxaldehyde followed by a hydride source; or reacting a compound of Formula I-H with cyclopropanecarboxylic acid halide followed by a reducing agent; or reacting a compound of Formula I-H with cyclopropylmethyl halide or activated cyclopropane methanol; to provide a compound of Formula I-MCP:

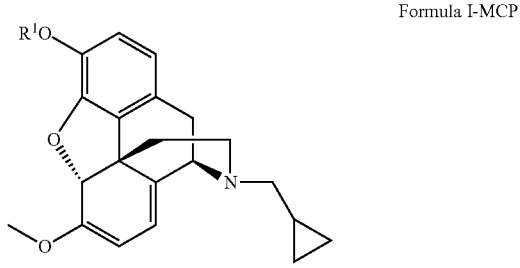

Formula I-MCP wherein R¹ is H (Compound HO-I-MCP), methyl (Compound MeO-I-MCP), or benzyl (Compound BnO-I-MCP).

In some embodiments, the methods comprise reacting a compound of Formula I-H with benzyl halide, benzyl sulfonate, or activated benzyl alcohol to provide a compound of Formula I-Bn:

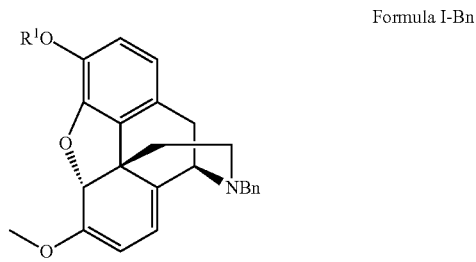

Formula I-Bn wherein R¹ is benzyl (Compound BnO-I-Bn). A preparation of Compound BnO-I-Bn, as an intermediate towards noroxymorphone and ultimately towards naltrexone and naloxone, was described in Helv. Chim. Acta 92:1359-65 (2009).

In some embodiments, the methods comprise reacting a compound of Formula I-H with acyl halide to provide a compound of Formula I-Ac:

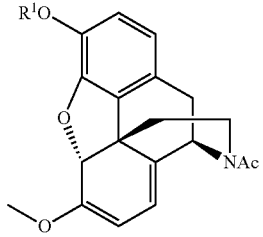

Formula I-Ac wherein R¹ is H (Compound HO-I-Ac), benzyl (Compound BnO-I-Ac), or acyl (Compound AcO-I-Ac).

As used herein, the term "acyl" includes $C_1$-$C_8$ aliphatic acyl groups (e.g., acetyl, ethanoyl, cyclopropanecarbonyl, etc.) and optionally substituted $C_6$-$C_{13}$ aromatic acyl groups (e.g., optionally substituted benzoyl ("Bz"), e.g., benzoyl, 4-methylbenzoyl, 4-fluorobenzoyl, etc.). For example, in certain embodiments, the methods comprise reacting a compound of Formula I-H with benzoyl chloride to provide a compound of Formula I-Ac.

In some embodiments, the methods comprise reacting a compound of Formula I-Ac (e.g., Compound HO-I-Ac) with benzyl halide, benzyl sulfonate, or activated benzyl alcohol to provide another compound of Formula I-Ac (e.g., Compound BnO-I-Ac).

In some embodiments, the methods comprise reacting a compound of Formula I-Ac (e.g., Compound AcO-I-Ac) with lithium aluminum hydride (LAH) to provide a compound of Formula I-Bn (e.g., Compound BnO-I-Bn).

In some embodiments, the methods comprise reacting a compound of Formula I-MCP (e.g., Compound HO-I-MCP) with benzyl halide, benzyl sulfonate, or activated benzyl alcohol to provide another compound of Formula I-MCP (e.g., Compound BnO-I-MCP).

In some embodiments, the methods comprise reacting a compound of Formula I-MCP with methyl vinyl ketone to provide a compound of Formula II-MCP:

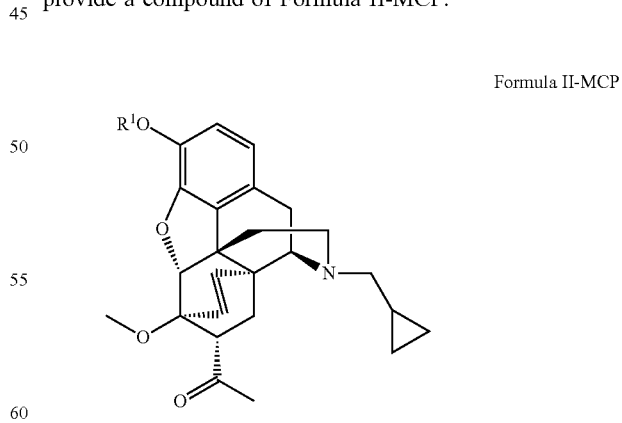

Formula II-MCP wherein R¹ is H (Compound HO-II-MCP), methyl (Compound MeO-II-MCP), or benzyl (Compound BnO-II-MCP).

In some embodiments, the methods comprise reacting a compound of Formula I-Bn with methyl vinyl ketone to provide a compound of Formula II-Bn:

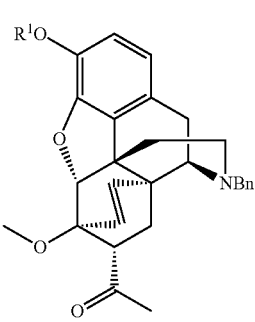

Formula II-Bn wherein R¹ is benzyl (Compound BnO-II-Bn).

In some embodiments, the methods comprise reacting a compound of Formula II-MCP (e.g., Compound HO-II-MCP) with benzyl halide, benzyl sulfonate, or activated benzyl alcohol to provide another compound of Formula II-MCP (e.g., Compound BnO-II-MCP).

In some embodiments, the methods comprise reacting a compound of Formula I-Ac with methyl vinyl ketone to provide a compound of Formula II-Ac:

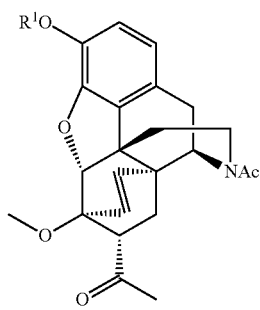

Formula II-Ac wherein R¹ is acyl (Compound AcO-II-Ac).

In some embodiments, the methods comprise reacting a compound of Formula II-MCP with $H_2$ in the presence of a hydrogenation catalyst to provide a compound of Formula IIIB-MCP:

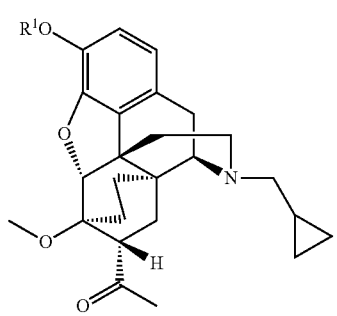

Formula IIIB-MCP wherein R¹ is H (Compound HO-IIIB-MCP) or methyl (Compound MeO-IIIB-MCP).

In some embodiments, the methods comprise reacting a compound of Formula II-Ac with $H_2$ in the presence of a hydrogenation catalyst to provide a compound of Formula IIIB-Ac:

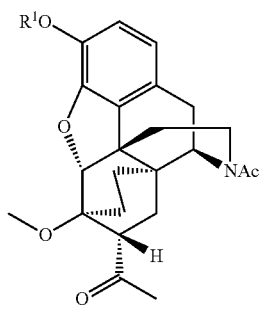

Formula IIIB-Ac wherein R¹ is Ac (Compound AcO-IIIB-Ac).

In some embodiments, the methods comprise reacting a compound of Formula II-MCP with tert-butylmagnesium halide to provide a compound of Formula IIIA-MCP:

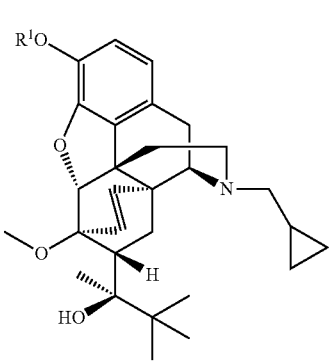

Formula IIIA-MCP wherein R¹ is H (Compound HO-IIIA-MCP), methyl (Compound MeO-IIIA-MCP), or benzyl (Compound BnO-IIIA-MCP).

In some embodiments, the methods comprise reacting a compound of formula IIIA-MCP (e.g., Compound Me-IIIA-MCP) with a demethylating agent to provide another compound of IIIA-MCP (e.g., Compound HO-IIIA-MCP).

In some embodiments, the methods comprise reacting a compound of Formula II-Bn with tert-butylmagnesium halide to provide a compound of Formula IIIA-Bn:

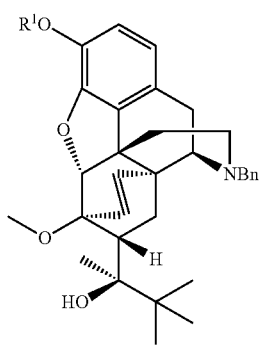

Formula IIIA-Bn wherein R¹ is benzyl (Compound BnO-IIIA-Bn).

In some embodiments, the methods comprise reacting a compound of Formula II-Ac with tert-butylmagnesium halide to provide a compound of Formula IIIA-Ac:

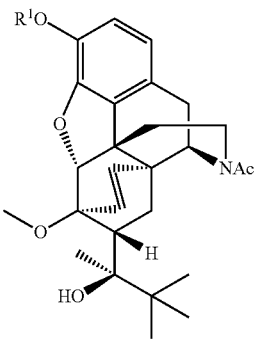

Formula IIIA-Ac wherein R¹ is H (Compound HO-IIIA-Ac).

In some embodiments, the methods comprise reacting a compound of Formula IIIA-Ac (e.g., Compound HO-IIIA-Ac), wherein Ac is optionally substituted benzoyl, with lithium aluminum hydride (LAH) to provide a compound of Formula IIIA-Bn (e.g., Compound HO-IIIA-Bn).

In some embodiments, the methods comprise reacting a compound of Formula IIIB-MCP with tert-butylmagnesium halide to provide a compound of Formula IV-MCP:

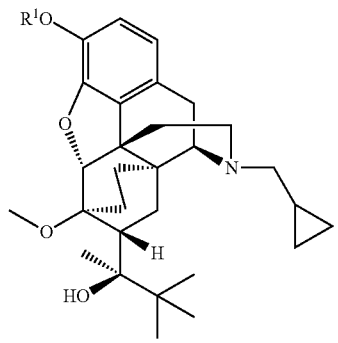

Formula IV-MCP wherein R¹ is H (Compound HO-IV-MCP; buprenorphine) or methyl (Compound MeO-IV-MCP).

In some embodiments, the methods comprise reacting a compound of Formula IIIB-Ac with tert-butylmagnesium halide to provide a compound of Formula IV-Ac:

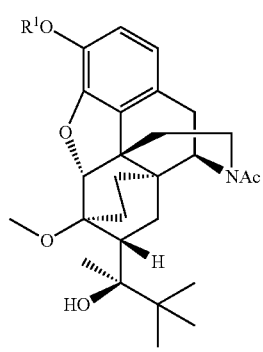

Formula IV-Ac wherein R¹ is H (Compound HO-IV-Ac).

In some embodiments, the methods comprise reacting a compound of Formula IIIA-MCP with $H_2$ in the presence of a hydrogenation catalyst to provide a compound of Formula IV-MCP (see above), wherein $R_1$ is H (Compound HO-IV-MCP; buprenorphine) or methyl (Compound MeO-IV-MCP).

In some embodiments, the methods comprise reacting a compound of Formula IIIA-Ac with $H_2$ in the presence of a hydrogenation catalyst to provide a compound of Formula IV-Ac (see above), wherein $R_1$ is H (Compound HO-IV-Ac).

In some embodiments, the methods comprise reacting a compound of Formula IIIA-Bn with $H_2$ in the presence of a hydrogenation catalyst to provide a compound of Formula IV-H:

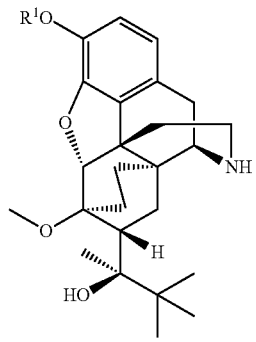

Formula IV-H wherein R¹ is H (Compound HO-IV-H; norbuprenorphine).

In some embodiments, the methods comprise reacting a compound of Formula IV-Ac (e.g., compound HO-IV-Ac) with Schwartz's reagent (zirconocene hydrochloride) or base to provide a compound of Formula IV-H (e.g., compound HO-IV-H).

In some embodiments, the methods comprise reacting a compound of Formula IV-MCP (e.g., Compound Me-IV-MCP) with a demethylating agent to provide buprenorphine.

In some embodiments, the methods comprise reacting a compound of Formula IV-H (e.g., Compound HO-IV-H) with cyclopropane carboxaldehyde followed by a hydride source; or reacting a compound of Formula IV-H (e.g., Compound HO-IV-H) with cyclopropanecarboxylic acid halide followed by a reducing agent; or reacting a compound of Formula IV-H (e.g., Compound HO-IV-H) with cyclopropylmethyl halide or activated cyclopropane methanol; to provide buprenorphine.

Formula I-H→Formula I-MCP

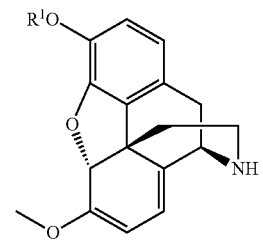

Formula I-H

| $R^1$ of Formula I-H | Compound |
|---|---|
| H | Compound HO-I-H |
| Me | Compound MeO-I-H |
| Bn | Compound BnO-I-H |

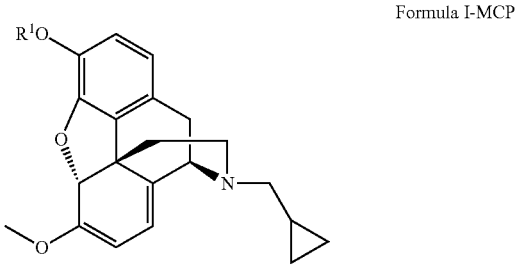

Formula I-MCP

| $R^1$ of Formula I-MCP | Compound |
|---|---|
| H | Compound HO-I-MCP |
| Me | Compound MeO-I-MCP |
| Bn | Compound BnO-I-MCP |

Step (i)(A1)

In some embodiments, reacting a compound of Formula I-H with cyclopropane carboxaldehyde followed by a hydride source provides a compound of Formula I-MCP. In certain embodiments, reacting Compound HO-I-H with cyclopropane carboxaldehyde followed by a hydride source provides Compound HO-I-MCP. In certain embodiments, reacting Compound MeO-I-H with cyclopropane carboxaldehyde followed by a hydride source provides Compound MeO-I-MCP. In certain embodiments, reacting Compound BnO-I-H with cyclopropane carboxaldehyde followed by a hydride source provides Compound BnO-I-MCP. See Examples 1 and 12.

In some embodiments, the hydride source is formic acid, hydrogen, sodium cyanoborohydride, sodium borohydride, or sodium triacetoxy borohydride. In some embodiments, the hydride source is formic acid. In some embodiments, the reaction is catalyzed by a ruthenium(I) complex or a ruthenium(II) complex, e.g., a dichloro(p-cymene)ruthenium(II) dimer. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof. In some embodiments, the reaction is performed in the presence of a trialkylamine, e.g., triethylamine, diisopropylethylamine, 4-methyl-morpholine, or N-methyl-piperidine.

In some embodiments, the cyclopropane carboxaldehyde is reacted at a temperature within the range of about 30° C. to about 90° C., e.g., about 35° C. to about 90° C., or about 40° C. to about 90° C., or about 45° C. to about 90° C., or about 50° C. to about 90° C., or about 55° C. to about 90° C., or about 60° C. to about 90° C., or about 65° C. to about 90° C., or about 70° C. to about 90° C., or about 30° C. to about 85° C., or about 30° C. to about 80° C., or about 30° C. to about 75° C., or about 30° C. to about 70° C., or about 30° C. to about 65° C., or about 30° C. to about 60° C., or about 30° C. to about 55° C., or about 30° C. to about 50° C., or about 35° C. to about 85° C., or about 40° C. to about 80° C., or about 45° C. to about 75° C., or about 50° C. to about 70° C., or about 55° C. to about 65° C. In some embodiments, the cyclopropane carboxaldehyde is reacted for a period of time within the range of about 30 minutes to about 5 hours, e.g., about 1 hour to about 5 hours, or about 1.5 hours to about 5 hours, or about 2 hours to about 5 hours, or about 2.5 hours to about 5 hours, or about 3 hours to about 5 hours, or about 3.5 hours to about 5 hours, or about 4 hours to about 5 hours, or about 30 minutes to about 4.5 hours, or about 30 minutes to about 4 hours, or about 30 minutes to about 3.5 hours, or about 30 minutes to about 3 hours, or about 30 minutes to about 2.5 hours, or about 30 minutes to about 2 hours, or about 30 minutes to about 1.5 hours.

Step (i)(A2)

In some embodiments, reacting a compound of Formula I-H with cyclopropanecarboxylic acid halide followed by a reducing agent provides a compound of Formula I-MCP. In certain embodiments, reacting Compound HO-I-H with cyclopropanecarboxylic acid halide followed by a reducing agent provides Compound HO-I-MCP. In certain embodiments, reacting Compound MeO-I-H with cyclopropanecarboxylic acid halide followed by a reducing agent provides Compound MeO-I-MCP. In certain embodiments, reacting Compound BnO-I-H with cyclopropanecarboxylic acid halide followed by a reducing agent provides Compound BnO-I-MCP. See Examples 2 and 13.

In some embodiments, the cyclopropanecarboxylic acid halide is cyclopropanecarboxylic acid chloride, cyclopropanecarboxylic acid anhydride, cyclopropanecarboxylic acid bromide, or an activated cyclopropanecarboxylic acid (e.g., an activated cyclopropanecarboxylic acid formed by reaction with an alcohol such as pentafluorophenol, 4-nitrophenol, N-hydroxysuccinimide, N-hydroxymaleimide, 1-Hydroxybenzotriazole, or 1-hydroxy-7-azabenzotriazole). In some embodiments, the reducing agent is $LiAlH_4$ or $NaBH_4$. In some embodiments, the reaction with cyclopropanecarboxylic acid halide is performed in a solvent comprising a nonpolar solvent, e.g., dichloromethane, chloroform, toluene, 1,4-dioxane, diethyl ether, benzene, or a mixture thereof. In some embodiments, the reaction with a reducing agent is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the cyclopropanecarboxylic acid halide is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 20° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C.

In some embodiments, the cyclopropanecarboxylic acid halide is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days. In some embodiments, the reducing agent is reacted at a temperature within the range of about 35° C. to about 85° C., e.g., about 40° C. to about 85° C., or about 45° C. to about 85° C., or about 50° C. to about 85° C., or about 55° C. to about 85° C., or about 60° C. to about 85° C., or about 65° C. to about 85° C., or about 35° C. to about 80° C., or about 35° C. to about 75° C., or about 35° C. to about 70° C., or about 35° C. to about 65° C., or about 35° C. to about 60° C., or about 35° C. to about 55° C., or about 40° C. to about 80° C., or about 45° C. to about 75° C., or about 50° C. to about 70° C., or about 55° C. to about 65° C. In some embodiments, the reducing agent is reacted for a period of time within the range of about 5 minutes to about 3 hours, e.g., or about 10 minutes to about 3 hours, or about 15 minutes to about 3 hours, or about 30 minutes to about 3 hours, or about 45 minutes to about 3 hours, or about 1 hour to about 3 hours, or about 1.25 hours to about 3 hours, or about 1.5 hours to about 3 hours, or about 1.75 hours to about 3 hours, or about 2 hours to about 3 hours, or about 5 minutes to about 2.75 hours, or about 5 minutes to about 2.5 hours, or about 5 minutes to about 2.25 hours, or about 5 minutes to about 2 hours, or about 5 minutes to about 1.75 hours, or about 5 minutes to about 1.5 hours, or about 5 minutes to about 1.25 hours, or about 5 minutes to about 1 hour, or about 10 minutes to about 2.75 hours, or about 15 minutes to about 2.5 hours, or about 30 minutes to about 2.25 hours, or about 45 minutes to about 2 hours, or about 1 hour to about 1.75 hours.

Step (i)(A3)

In some embodiments, reacting a compound of Formula I-H with cyclopropylmethyl halide or activated cyclopropane methanol (e.g., activated with a sulfonate group such as a p-toluene sulfonyl group or a methyl sulfonyl group, or with triphenylphosphine) provides a compound of Formula I-MCP. In certain embodiments, reacting Compound HO-I-H with cyclopropylmethyl halide or activated cyclopropane methanol provides Compound HO-I-MCP. In certain embodiments, reacting Compound MeO-I-H with cyclopropylmethyl halide or activated cyclopropane methanol provides Compound MeO-I-MCP. In certain embodiments, reacting Compound BnO-I-H with cyclopropylmethyl halide or activated cyclopropane methanol provides Compound BnO-I-MCP. See Examples 3, 14, and 23.

In some embodiments, the cyclopropylmethyl halide is cyclopropylmethyl chloride or cyclopropylmethyl bromide. In some embodiments, the reaction is performed in the presence of a trialkylamine, e.g., triethylamine, diisopropylethylamine, 4-methyl-morpholine, or N-methyl-piperidine. In some embodiments, the reaction is performed in a solvent comprising a polar protic solvent, e.g., n-butanol, isopropanol, ethanol, methanol, water, or a mixture thereof.

In some embodiments, the cyclopropylmethyl halide or activated cyclopropane methanol is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the cyclopropylmethyl halide or activated cyclopropane methanol is reacted for a period of time within the range of about 30 minutes to about 6 hours, e.g., about 1 hours to about 6 hours, or about 1.5 hours to about 6 hours, or about 2 hours to about 6 hours, or about 2.5 hours to about 6 hours, or about 3 hours to about 6 hours, or about 3.5 hours to about 6 hours, or about 4 hours to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 30 minutes to about 3 hours, or about 30 minutes to about 2.5 hours, or about 1 hours to about 5.5 hours, or about 1.5 hours to about 5 hours, or about 2 hours to about 4.5 hours, or about 2.5 hours to about 4 hours.

Formula I-H→Formula I-Bn

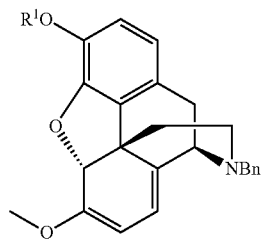

Formula I-Bn

| $R^1$ of Formula I-Bn | Compound |
|---|---|
| Bn | Compound BnO-I-Bn |

Step (i)(F)

In some embodiments, reacting a compound of Formula I-H with benzyl halide, benzyl sulfonate, or activated benzyl alcohol (e.g., activated with a sulfonate group such as a p-toluene sulfonyl group or a methyl sulfonyl group, or with triphenylphosphine) provides a compound of Formula I-Bn. In certain embodiments, reacting Compound HO-I-H with benzyl halide, benzyl sulfonate, or activated benzyl alcohol provides Compound BnO-I-Bn. See Example 31.

In some embodiments, the benzyl halide is benzyl chloride or benzyl bromide. In some embodiments, the reaction is performed in the presence of a strong base, e.g., an alkali metal hydride. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the benzyl halide, benzyl sulfonate, or activated benzyl alcohol is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 20° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the benzyl halide, benzyl sulfonate, or activated benzyl alcohol is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days.

Formula I-H→Formula I-Ac

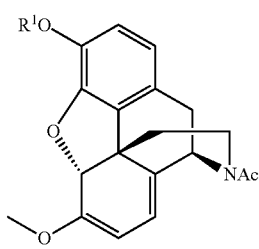

Formula I-Ac

| $R^1$ of Formula I-Ac | Compound |
|---|---|
| H | Compound HO-I-Ac |
| Ac | Compound AcO-I-Ac |
| Bn | Compound BnO-I-Ac |

Step (i)(G)

In some embodiments, reacting a compound of Formula I-H with acyl halide provides a compound of Formula I-Ac. In certain embodiments, reacting Compound HO-I-H with acyl halide provides Compound HO-I-Ac. See Example 36. In certain embodiments, reacting Compound HO-I-H with acyl halide provides Compound AcO-I-Ac. See Example 39.

In some embodiments, the acyl halide is optionally substituted $C_6$-$C_{13}$ aromatic acyl halide, e.g, optionally substituted benzoyl halide. In some embodiments, the acyl halide is aliphatic acylc halide, e.g., acetyl chloride. In some embodiments, the reaction is performed in the presence of a trialkylamine, e.g., triethylamine, diisopropylethylamine, 4-methyl-morpholine, or N-methyl-piperidine. In some embodiments, the reaction is performed in a solvent comprising a nonpolar solvent, e.g., dichloromethane, chloroform, toluene, 1,4-dioxane, diethyl ether, benzene, or a mixture thereof.

In some embodiments, the acyl halide is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 20° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the acyl halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 1.5 hours to about 6.5 hours, or about 1.5 hours to about 6 hours, or about 1.5 hours to about 5.5 hours.

Formula I-Ac→Formula I-Ac
Step (ii)(F)

In some embodiments, reacting a compound of Formula I-Ac with benzyl halide, benzyl sulfonate, or activated benzyl alcohol (e.g., activated with a sulfonate group such as a p-toluene sulfonyl group or a methyl sulfonyl group, or with triphenylphosphine) provides another compound of Formula I-Ac. In certain embodiments, reacting Compound HO-I-Ac with benzyl halide, benzyl sulfonate, or activated benzyl alcohol provides Compound BnO-I-Ac. See Example 37.

In some embodiments, the benzyl halide is benzyl chloride or benzyl bromide. In some embodiments, the reaction is performed in the presence of a strong base, e.g., an alkali metal hydride. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the benzyl halide, benzyl sulfonate, or activated benzyl alcohol is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 20° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the benzyl halide, benzyl sulfonate, or activated benzyl alcohol is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days.

Formula I-Ac→Formula I-Bn
Step (iii)(H)

In some embodiments, reacting a compound of Formula I-Ac with lithium aluminum hydride provides a compound of Formula I-Bn. In certain embodiments, reacting Compound BnO-I-Ac with lithium aluminum hydride provides Compound BnO-I-Bn. See Example 38.

In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the lithium aluminum hydride is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to about 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the lithium aluminum hydride is reacted for a period of time within the range of about 10 minutes to about 8 hours, e.g., about 20 minutes to about 8 hours, about 30 minutes to about 8 hours, about 1 hour to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours.

Formula I-MCP→Formula I-MCP

Step (ii)(F)

In some embodiments, reacting a compound of Formula I-MCP with benzyl halide, benzyl sulfonate, or activated benzyl alcohol (e.g., activated with a sulfonate group such as a p-toluene sulfonyl group or a methyl sulfonyl group, or with triphenylphosphine) provides another compound of Formula I-MCP. In certain embodiments, reacting Compound HO-I-MCP with benzyl halide, benzyl sulfonate, or activated benzyl alcohol provides Compound BnO-I-MCP. See Example 22.

In some embodiments, the benzyl halide is benzyl chloride or benzyl bromide. In some embodiments, the reaction is performed in the presence of a strong base, e.g., an alkali metal hydride. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the benzyl halide, benzyl sulfonate, or activated benzyl alcohol is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 40° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the benzyl halide, benzyl sulfonate, or activated benzyl alcohol is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days.

Formula I-Me→Formula I-Me

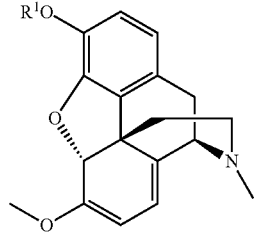

Formula I-Me

| R¹ of Formula I-Me | Compound |
|---|---|
| H | Compound HO-I-Me |
| Bn | Compound BnO-I-Me |

Step (i)(F)

In some embodiments, reacting a compound of Formula I-Me with benzyl halide, benzyl sulfonate, or activated benzyl alcohol provides another compound of Formula I-Me. In certain embodiments, reacting Compound HO-I-Me with benzyl halide, benzyl sulfonate, or activated benzyl alcohol provides Compound BnO-I-Me. See Example 29.

In some embodiments, the benzyl halide is benzyl chloride or benzyl bromide. In some embodiments, the reaction is performed in the presence of a strong base, e.g., an alkali metal hydride. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the benzyl halide, benzyl sulfonate, or activated benzyl alcohol is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 40° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the benzyl halide, benzyl sulfonate, or activated benzyl alcohol is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days.

Formula I-Me→Formula I-H

Step (ii)(E)

In some embodiments, reacting a compound of Formula I-Me with an azodicarboxylate followed by an acid or an addition salt thereof provides a compound of Formula I-H. In certain embodiments, reacting Compound BnO-I-Me with an azodicarboxylate provides Compound BnO-I-H. See Example 30.

In some embodiments, the azodicarboxylate is diethyl azodicarboxylate or diisopropyl azodicarboxylate. In some embodiments, the acid is hydrochloric acid. In some embodiments, the addition salt of the acid is pyridine-HCl. In some embodiments, the reaction with an azodicarboxylate is performed in a solvent comprising a nonpolar solvent, e.g., tert-butylmethyl ether, 2-methyl-tetrahydrofuran, diethyl ether, dimethoxymethane, benzene, toluene, or a mixture of thereof. In some embodiments, the reaction with an acid or an addition salt thereof is performed in a solvent comprising a polar protic solvent, e.g., n-butanol, isopropanol, ethanol, methanol, water, or a mixture thereof.

In some embodiments, the azodicarboxylate is reacted at a temperature within the range of about 35° C. to about 85° C., e.g., about 40° C. to about 85° C., or about 45° C. to about 85° C., or about 50° C. to about 85° C., or about 55° C. to about 85° C., or about 60° C. to about 85° C., or about 65° C. to about 85° C., or about 35° C. to about 80° C., or about 35° C. to about 75° C., or about 35° C. to about 70° C., or about 35° C. to about 65° C., or about 35° C. to about 60° C., or about 35° C. to about 55° C., or about 40° C. to about 80° C., or about 45° C. to about 75° C., or about 50° C. to about 70° C., or about 55° C. to about 65° C. In some embodiments, the acid or the addition salt thereof is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the azodicarboxylate is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days. In some embodiments, the acid or the addition salt thereof is reacted at a temperature of about 30 minutes to about 6 hours, e.g., about 1 hours to about 6 hours, or about 1.5 hours to about 6 hours, or about 2 hours to about 6 hours, or about 2.5 hours to about 6 hours, or about 3 hours to about 6 hours, or about 3.5 hours to about 6 hours, or about 4 hours to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 30 minutes to about 3 hours, or about 30 minutes to about 2.5 hours, or about 1 hours to about 5.5 hours, or about 1.5 hours to about 5 hours, or about 2 hours to about 4.5 hours, or about 2.5 hours to about 4 hours.

Formula I-MCP→Formula II-MCP

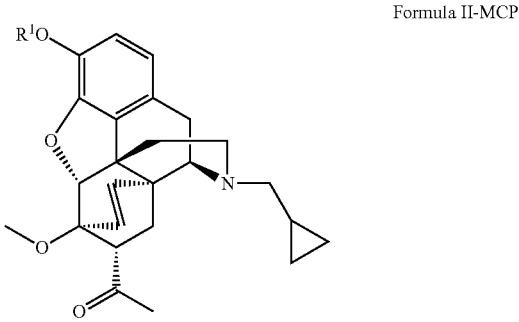

Formula II-MCP

| R¹ of Formula II-MCP | Compound |
|---|---|
| H | Compound HO-II-MCP |
| Me | Compound MeO-II-MCP |
| Bn | Compound BnO-II-MCP |

Step (ii)(B)

In some embodiments, reacting a compound of Formula I-MCP with methyl vinyl ketone provides a compound of Formula II-MCP. In certain embodiments, reacting Compound HO-I-MCP with methyl vinyl ketone provides Compound HO-II-MCP. In certain embodiments, reacting Compound MeO-I-MCP with methyl vinyl ketone provides Compound MeO-II-MCP. See Examples 4 and 15.

In some embodiments, the reaction is performed in a solvent comprising a nonpolar solvent, e.g., dichloromethane, chloroform, toluene, 1,4-dioxane, diethyl ether, benzene, or a mixture thereof.

In some embodiments, the methyl vinyl ketone is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the methyl vinyl ketone is reacted for a period of time within the range of about 2 hours to about 2 days, e.g., about 4 hours to about 2 days, or about 6 hours to about 2 days, or about 12 hours to about 2 days, or about 18 hours to about 2 days, or about 1 days to about 2 days, or about 1.25 days to about 2 days, or about 1.5 days to about 2 days, or about 2 hours to about 1.75 days, or about 2 hours to about 1.5 days, or about 2 hours to about 1.25 days, or about 2 hours to about 1 day, or about 2 hours to about 18 hours, or about 2 hours to about 12 hours, or about 4 hours to about 1.75 days, or about 6 hours to about 1.5 days, or about 12 hours to about 1.25 days, or about 18 hours to about 1 day.

Step (iii)(B)

In some embodiments, reacting a compound of Formula I-MCP with methyl vinyl ketone provides a compound of Formula II-MCP. In certain embodiments, reacting Compound BnO-I-MCP with methyl vinyl ketone provides Compound BnO-II-MCP. See Example 25.

In some embodiments, the reaction is performed in a solvent comprising a nonpolar solvent, e.g., dichloromethane, chloroform, toluene, 1,4-dioxane, diethyl ether, benzene, or a mixture thereof.

In some embodiments, the methyl vinyl ketone is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the methyl vinyl ketone is reacted for a period of time within the range of about 2 hours to about 2 days, e.g., about 4 hours to about 2 days, or about 6 hours to about 2 days, or about 12 hours to about 2 days, or about 18 hours to about 2 days, or about 1 days to about 2 days, or about 1.25 days to about 2 days, or about 1.5 days to about 2 days, or about 2 hours to about 1.75 days, or about 2 hours to about 1.5 days, or about 2 hours to about 1.25 days, or about 2 hours to about 1 day, or about 2 hours to about 18 hours, or about 2 hours to about 12 hours, or about 4 hours to about 1.75 days, or about 6 hours to about 1.5 days, or about 12 hours to about 1.25 days, or about 18 hours to about 1 day.

Formula I-Bn→Formula II-Bn

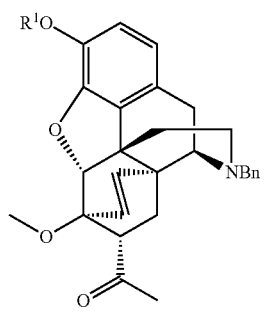

Formula II-Bn

| R¹ of Formula II-Bn | Compound |
|---|---|
| Bn | Compound BnO-II-Bn |

Step (ii)(B), Step (iv)(B)

In some embodiments, reacting a compound of Formula I-Bn with methyl vinyl ketone provides a compound of Formula II-Bn. In certain embodiments, reacting Compound BnO-I-Bn with methyl vinyl ketone provides Compound BnO-II-Bn. See Example 32.

In some embodiments, the reaction is performed in a solvent comprising a nonpolar solvent, e.g., dichloromethane, chloroform, toluene, 1,4-dioxane, diethyl ether, benzene, or a mixture thereof.

In some embodiments, the methyl vinyl ketone is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the methyl vinyl ketone is reacted for a period of time within the range of about 2 hours to about 2 days, e.g., about 4 hours to about 2 days, or about 6 hours to about 2 days, or about 12 hours to about 2 days, or about 18 hours to about 2 days, or about 1 days to about 2 days, or about 1.25 days to about 2 days, or about 1.5 days to about 2 days, or about 2 hours to about 1.75 days, or about 2 hours to about 1.5 days, or about 2 hours to about 1.25 days, or about 2 hours to about 1 day, or about 2 hours to about 18 hours, or about 2 hours to about 12 hours, or about 4 hours to about 1.75 days, or about 6 hours to about 1.5 days, or about 12 hours to about 1.25 days, or about 18 hours to about 1 day.

Formula I-Ac→Formula II-Ac

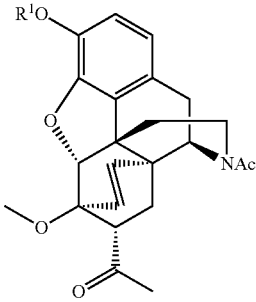

Formula II-Ac

| R¹ of Formula II-Ac | Compound |
|---|---|
| Ac | Compound AcO-II-Ac |

Step (ii)(B)

In some embodiments, reacting a compound of Formula I-Ac with methyl vinyl ketone provides a compound of Formula II-Ac. In certain embodiments, reacting Compound AcO-I-Ac with methyl vinyl ketone provides Compound AcO-II-Ac. See Example 40.

In some embodiments, the reaction is performed in a solvent comprising a nonpolar solvent, e.g., dichloromethane, chloroform, toluene, 1,4-dioxane, diethyl ether, benzene, or a mixture thereof.

In some embodiments, the methyl vinyl ketone is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the methyl vinyl ketone is reacted for a period of time within the range of about 2 hours to about 2 days, e.g., about 4 hours to about 2 days, or about 6 hours to about 2 days, or about 12 hours to about 2 days, or about 18 hours to about 2 days, or about 1 days to about 2 days, or about 1.25 days to about 2 days, or about 1.5 days to about 2 days, or about 2 hours to about 1.75 days, or about 2 hours to about 1.5 days, or about 2 hours to about 1.25 days, or about 2 hours to about 1 day, or about 2 hours to about 18 hours, or about 2 hours to about 12 hours, or about 4 hours to about 1.75 days, or about 6 hours to about 1.5 days, or about 12 hours to about 1.25 days, or about 18 hours to about 1 day.

Formula II-MCP→Formula II-MCP

Step (iii)(F)

In some embodiments, reacting a compound of Formula II-MCP with benzyl halide, benzyl sulfonate, or activated benzyl alcohol provides another compound of Formula II-MCP. In certain embodiments, reacting Compound HO-II-MCP with benzyl halide, benzyl sulfonate, or activated benzyl alcohol provides Compound BnO-II-MCP. See Example 24.

In some embodiments, the benzyl halide is benzyl chloride or benzyl bromide. In some embodiments, the reaction is performed in the presence of a strong base, e.g., an alkali metal hydride. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the benzyl halide, benzyl sulfonate, or activated benzyl alcohol is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 20° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the benzyl halide, benzyl sulfonate, or activated benzyl alcohol is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days.

Formula II-MCP→Formula IIIB-MCP

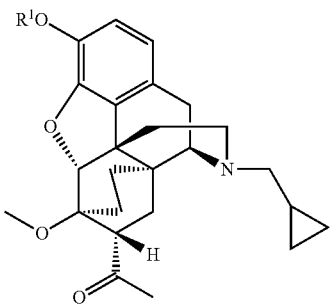

Formula IIIB-MCP

| $R^1$ of Formula IIIB-MCP | Compound |
|---|---|
| H | Compound HO-IIIB-MCP |
| Me | Compound MeO-IIIB-MCP |

Step (iii)(C)

In some embodiments, reacting a compound of Formula II-MCP with $H_2$ in the presence of a hydrogenation catalyst provides a compound of Formula IIIB-MCP. In certain embodiments, reacting Compound HO-II-MCP with $H_2$ in the presence of a hydrogenation catalyst provides Compound HO-IIIB-MCP. In certain embodiments, reacting Compound MeO-II-MCP with $H_2$ in the presence of a hydrogenation catalyst provides Compound MeO-IIIB-MCP. See Examples 5, 16, and 17.

In some embodiments, the hydrogenation catalyst comprises nickel, palladium, platinum, rhodium, or ruthenium. In some embodiments, the hydrogenation catalyst comprises platinum or palladium, supported on carbon. In some embodiments, the reaction is performed in a solvent comprising a polar protic or aprotic solvent, e.g., n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

In some embodiments, the hydrogen is reacted at a temperature within the range of about 15° C. to about 120° C., e.g., about 20° C. to about 120° C., or about 30° C. to about 120° C., or about 40° C. to about 120° C., or about 15° C. to about 115° C., or about 20° C. to about 110° C., or about 30° C. to about 105° C., or about 40° C. to about 115° C., or about 50° C. to about 110° C. In some embodiments, the hydrogen is reacted for a period of time within the range of about 6 hours to about 3 days, e.g., about 12 hours to about 3 days, or about 18 hours to about 3 days, or about 1 day to about 3 days, or about 1.25 days to about 3 days, or about 1.5 days to about 3 days, or about 6 hours to about 2.75 days, or about 6 hours to about 2.5 days, or about 6 hours to about 2.25 days, or about 6 hours to about 2 day, or about 6 hours to about 36 hours, or about 12 hours to about 2.5 days, or about 24 hours to about 2 days. In some embodiments, the hydrogen is reacted at a pressure within the range of about 1 atm to about 3 atm, e.g., about 1.25 atm to about 3 atm, or about 1.5 atm to about 3 atm, or about 1.75 atm to about 3 atm, or about 2 atm to about 3 atm, or about 1 atm to about 2.75 atm, or about 1 atm to about 2.5 atm, or about 1 atm to about 2.25 atm, or about 1 atm to about 2 atm, or about 1.25 atm to about 2.75 atm, or about 1.5 atm to about 2.5 atm, or about 1.75 atm to about 2.25 atm.

Formula II-Ac→Formula IIIB-Ac

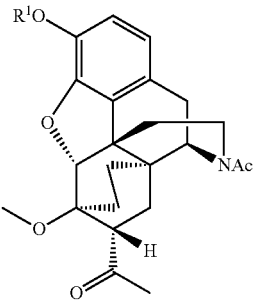

Formula IIIB-Ac

| R¹ of Formula IIIB-Ac | Compound |
|---|---|
| Ac | Compound AcO-IIIB-Ac |

Step (iii)(C)

In some embodiments, reacting a compound of Formula II-Ac with $H_2$ in the presence of a hydrogenation catalyst provides a compound of Formula IIIB-Ac. In certain embodiments, reacting Compound AcO-II-Ac with $H_2$ in the presence of a hydrogenation catalyst provides Compound AcO-IIIB-Ac. See, Example 44.

In some embodiments, the hydrogenation catalyst comprises nickel, palladium, platinum, rhodium, or ruthenium. In some embodiments, the hydrogenation catalyst comprises platinum or palladium, supported on carbon. In some embodiments, the reaction is performed in a solvent comprising a polar protic or aprotic solvent, e.g., n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

In some embodiments, the hydrogen is reacted at a temperature within the range of about 15° C. to about 120° C., e.g., about 20° C. to about 120° C., or about 30° C. to about 120° C., or about 40° C. to about 120° C., or about 15° C. to about 115° C., or about 20° C. to about 110° C., or about 30° C. to about 105° C., or about 40° C. to about 115° C., or about 50° C. to about 110° C. In some embodiments, the hydrogen is reacted for a period of time within the range of about 6 hours to about 3 days, e.g., about 12 hours to about 3 days, or about 18 hours to about 3 days, or about 1 day to about 3 days, or about 1.25 days to about 3 days, or about 1.5 days to about 3 days, or about 6 hours to about 2.75 days, or about 6 hours to about 2.5 days, or about 6 hours to about 2.25 days, or about 6 hours to about 2 day, or about 6 hours to about 36 hours, or about 12 hours to about 2.5 days, or about 24 hours to about 2 days. In some embodiments, the hydrogen is reacted at a pressure within the range of about 1 atm to about 3 atm, e.g., about 1.25 atm to about 3 atm, or about 1.5 atm to about 3 atm, or about 1.75 atm to about 3 atm, or about 2 atm to about 3 atm, or about 1 atm to about 2.75 atm, or about 1 atm to about 2.5 atm, or about 1 atm to about 2.25 atm, or about 1 atm to about 2 atm, or about 1.25 atm to about 2.75 atm, or about 1.5 atm to about 2.5 atm, or about 1.75 atm to about 2.25 atm.

Formula II-MCP→Formula IIIA-MCP

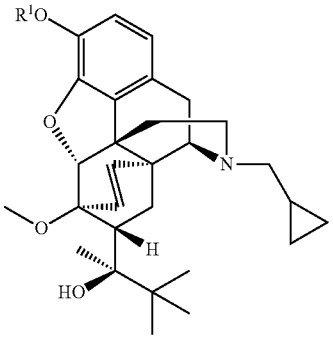

Formula IIIA-MCP

| R¹ of Formula IIIA-MCP | Compound |
|---|---|
| H | Compound HO-IIIA-MCP |
| Me | Compound MeO-IIIA-MCP |
| Bn | Compound BnO-IIIA-MCP |

Step (iii)(D)

In some embodiments, reacting a compound of Formula II-MCP with tert-butylmagnesium halide provides a compound of Formula IIIA-MCP. In certain embodiments, reacting Compound HO-II-MCP with tert-butylmagnesium halide provides Compound HO-IIIA-MCP. In certain embodiments, reacting Compound MeO-II-MCP with tert-butylmagnesium halide provides Compound MeO-IIIA-MCP. In certain embodiments, reacting Compound BnO-II-MCP with tert-butylmagnesium halide provides Compound BnO-IIIA-MCP. See Examples 6 and 18.

In some embodiments, the tert-butylmagnesium halide is tert-butylmagnesium chloride or tert-butylmagnesium bromide. In some embodiments, the reaction is performed in a solvent comprising a nonpolar solvent, e.g., tert-butylmethyl ether, 2-methyl-tetrahydrofuran, diethyl ether, dimethoxymethane, benzene, toluene, or a mixture of thereof.

In some embodiments, the tert-butylmagnesium halide is reacted at a temperature within the range of about 15° C. to about 40° C., e.g., about 20° C. to about 40° C., or about 25° C. to about 40° C., or about 30° C. to about 40° C., or about 15° C. to about 35° C., or about 15° C. to about 30° C., or about 15° C. to about 25° C., or about 20° C. to about 35° C., or about 25° C. to about 30° C. In some embodiments, the tert-butylmagnesium halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 2 hours to about 6.5 hours, or about 2.5 hours to about 6 hours, or about 3 hours to about 5.5 hours.

Formula II-Bn→Formula IIIA-Bn

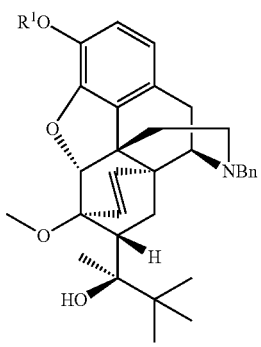

Formula IIIA-Bn

| R¹ of Formula IIIA-Bn | Compound |
|---|---|
| Bn | Compound BnO-IIIA-Bn |
| H | Compound HO-IIIA-Bn |

Step (iii)(D), Step (v)(D)

In some embodiments, reacting a compound of Formula II-Bn with tert-butylmagnesium halide provides a compound of Formula IIIA-Bn. In certain embodiments, reacting Compound BnO-II-Bn with tert-butylmagnesium halide provides Compound BnO-IIIA-Bn. See Example 33.

In some embodiments, the tert-butylmagnesium halide is tert-butylmagnesium chloride or tert-butylmagnesium bromide. In some embodiments, the reaction is performed in a solvent comprising a nonpolar solvent, e.g., tert-butylmethyl ether, 2-methyl-tetrahydrofuran, diethyl ether, dimethoxymethane, benzene, toluene, or a mixture of thereof.

In some embodiments, the tert-butylmagnesium halide is reacted at a temperature within the range of about 15° C. to about 100° C., e.g., about 20° C. to about 100° C., or about 25° C. to about 100° C., or about 30° C. to about 100° C., or about 15° C. to about 95° C., or about 15° C. to about 90° C., or about 15° C. to about 85° C., or about 20° C. to about 95° C., or about 25° C. to about 90° C. In some embodiments, the tert-butylmagnesium halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 2 hours to about 6.5 hours, or about 2.5 hours to about 6 hours, or about 3 hours to about 5.5 hours.

Formula II-Ac→Formula IIIA-Ac

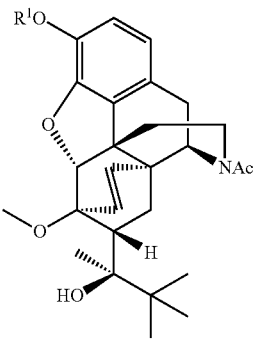

Formula IIIA-Ac

| R¹ of Formula IIIA-Bn | Compound |
|---|---|
| H | Compound HO-IIIA-Ac |

Step (iii)(D)

In some embodiments, reacting a compound of Formula II-Ac with tert-butylmagnesium halide provides a compound of Formula IIIA-Ac. In certain embodiments, reacting Compound AcO-II-Ac with tert-butylmagnesium halide provides Compound HO-IIIA-Ac. See Example 41.

In some embodiments, the tert-butylmagnesium halide is tert-butylmagnesium chloride or tert-butylmagnesium bromide. In some embodiments, the reaction is performed in a solvent comprising a nonpolar solvent, e.g., tert-butylmethyl ether, 2-methyl-tetrahydrofuran, diethyl ether, dimethoxymethane, benzene, toluene, or a mixture of thereof.

In some embodiments, the tert-butylmagnesium halide is reacted at a temperature within the range of about 15° C. to about 100° C., e.g., about 20° C. to about 100° C., or about 25° C. to about 100° C., or about 30° C. to about 100° C., or about 15° C. to about 95° C., or about 15° C. to about 90° C., or about 15° C. to about 85° C., or about 20° C. to about 95° C., or about 25° C. to about 90° C. In some embodiments, the tert-butylmagnesium halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 2 hours to about 6.5 hours, or about 2.5 hours to about 6 hours, or about 3 hours to about 5.5 hours.

Formula IIIA-Ac→Formula IIIA-Bn

Step (iv)(H)

In some embodiments, reacting a compound of Formula IIIA-Ac with lithium aluminum hydride provides a compound of Formula IIIA-Bn. In certain embodiments, reacting Compound HO-IIIA-Ac with lithium aluminum hydride provides Compound HO-IIIA-Bn. See Example 42.

In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the lithium aluminum hydride is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to about 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the lithium aluminum hydride is reacted for a period of time within the range of about 10 minutes to about 8 hours, e.g., about 20 minutes to about 8 hours, about 30 minutes to about 8 hours, about 1 hour to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours.

Formula IIIA-MCP→Formula IIIA-MCP

Step (iv)(E)

In some embodiments, reacting a compound of Formula IIIA-MCP with a demethylating agent provides another compound of Formula IIIA-MCP. In certain embodiments, reacting Compound MeO-IIIA-MCP with a demethylating agent provides Compound HO-IIIA-MCP. See Example 9.

In some embodiments, the demethylating agent is a thiolate, e.g., a dodecane thiolate. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the demethylating agent is reacted at a temperature within the range of about 50° C. to about 190° C., e.g., about 60° C. to about 190° C., or about 70° C. to about 190° C., or about 80° C. to about 190° C., or about 90° C. to about 190° C., or about 100° C. to about 190° C., or about 110° C. to about 190° C., or about 120° C. to about 190° C., or about 130° C. to about 190° C., or about 140° C. to about 190° C., or about 150° C. to about 190° C., or about 50° C. to about 180° C., or about 50° C. to about 170° C., or about 50° C. to about 160° C., or about 50° C. to about 150° C., or about 50° C. to about 140° C., or about 50° C. to about 130° C., or about 50° C. to about 120° C., or about 50° C. to about 110° C., or about 50° C. to about 100° C., or about 50° C. to about 90° C., or about 60° C. to about 180° C., or about 70° C. to about 170° C., or about 80° C. to about 160° C., or about 90° C. to about 150° C., or about 100° C. to about 140° C. In some embodiments, the demethylating agent is reacted for a period of time within the range of about 4 hours to about 2 days, e.g., about 8 hours to about 2 days, or about 12 hours to about 2 days, or about 16 hours to about 2 days, or about 20 hours to about 2 days, or about 1 day to about 2 days, or about 1.25 days to about 2 days, or about 1.5 days to about 2 days, or about 4 hours to about 1.75 days, or about 4 hours to about 1.5 days, or about 4 hours to about 1.25 days, or about 4 hours to about 1 day, or about 4 hours to about 20 hours, or about 4 hours to about 16 hours, or about 4 hours to about 12 hours, or about 8 hours to about 1.75 days, or about 12 hours to about 1.5 days, or about 16 hours to about 1.25 days.

Formula IIIB-MCP→Formula IV-MCP

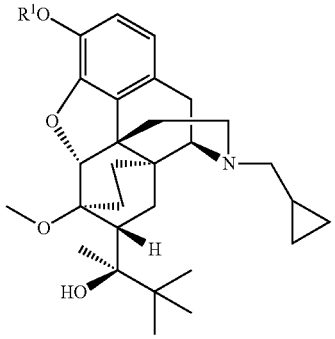

Formula IV-MCP

| R¹ of Formula IV-MCP | Compound |
|---|---|
| H | buprenorphine |
| Me | Compound MeO-IV-MCP |

Step (iv)(D)

In some embodiments, reacting a compound of Formula IIIB-MCP with tert-butylmagnesium halide provides a compound of Formula IV-MCP. In certain embodiments, reacting Compound HO-IIIB-MCP with tert-butylmagnesium halide provides buprenorphine. In certain embodiments, reacting Compound MeO-IIIB-MCP with tert-butylmagnesium halide provides Compound MeO-IV-MCP. See Examples 7, 19, 20, and 26.

In some embodiments, the tert-butylmagnesium halide is tert-butylmagnesium chloride or tert-butylmagnesium bromide. In some embodiments, the reaction is performed in a solvent comprising a nonpolar solvent, e.g., tert-butylmethyl ether, 2-methyl-tetrahydrofuran, diethyl ether, dimethoxymethane, benzene, toluene, or a mixture of thereof.

In some embodiments, the tert-butylmagnesium halide is reacted at a temperature within the range of about 15° C. to about 40° C., e.g., about 20° C. to about 40° C., or about 25° C. to about 40° C., or about 30° C. to about 40° C., or about 15° C. to about 35° C., or about 15° C. to about 30° C., or about 15° C. to about 25° C., or about 20° C. to about 35° C., or about 25° C. to about 30° C. In some embodiments, the tert-butylmagnesium halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 2 hours to about 6.5 hours, or about 2.5 hours to about 6 hours, or about 3 hours to about 5.5 hours.

Formula IIIA-MCP→Formula IV-MCP

Step (iv)(C), Step (v)(C)

In some embodiments, reacting a compound of Formula IIIA-MCP with $H_2$ in the presence of a hydrogenation catalyst provides a compound of Formula IV-MCP. In certain embodiments, reacting Compound HO-IIIA-MCP with $H_2$ in the presence of a hydrogenation catalyst provides buprenorphine. In certain embodiments, reacting Compound MeO-IIIA-MCP with $H_2$ in the presence of a hydrogenation catalyst provides Compound MeO-IV-MCP. In certain embodiments, reacting Compound BnO-IIIA-MCP with $H_2$ in the presence of a hydrogenation catalyst provides buprenorphine. See Examples 8, 11, 21, and 27.

In some embodiments, the hydrogenation catalyst comprises nickel, palladium, platinum, rhodium, or ruthenium. In some embodiments, the hydrogenation catalyst comprises platinum or palladium, supported on carbon. In some embodiments, the reaction is performed in a solvent comprising a polar protic or aprotic solvent, e.g., n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

In some embodiments, the hydrogen is reacted at a temperature within the range of about 15° C. to about 120° C., e.g., about 20° C. to about 120° C., or about 30° C. to about 120° C., or about 40° C. to about 120° C., or about 15° C. to about 115° C., or about 20° C. to about 110° C., or about 30° C. to about 105° C., or about 40° C. to about 115° C., or about 50° C. to about 110° C. In some embodiments, the hydrogen is reacted for a period of time within the range of about 6 hours to about 3 days, e.g., about 12 hours to about 3 days, or about 18 hours to about 3 days, or about 1 day to about 3 days, or about 1.25 days to about 3 days, or about 1.5 days to about 3 days, or about 6 hours to about 2.75 days, or about 6 hours to about 2.5 days, or about 6 hours to about 2.25 days, or about 6 hours to about 2 day, or about 6 hours to about 36 hours, or about 12 hours to about 2.5 days, or about 24 hours to about 2 days. In some embodiments, the hydrogen is reacted at a pressure within the range of about 1 atm to about 3 atm, e.g., about 1.25 atm to about 3 atm, or about 1.5 atm to about 3 atm, or about 1.75 atm to about 3 atm, or about 2 atm to about 3 atm, or about 1 atm to about 2.75 atm, or about 1 atm to about 2.5 atm, or about 1 atm to about 2.25 atm, or about 1 atm to about 2 atm, or about 1.25 atm to about 2.75 atm, or about 1.5 atm to about 2.5 atm, or about 1.75 atm to about 2.25 atm.

Formula IIIB-Ac→Formula IV-Ac

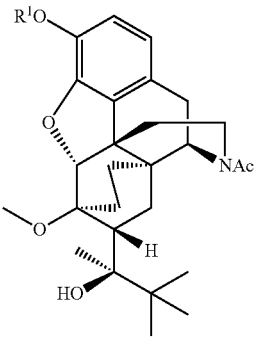

Formula IV-Ac

| $R^1$ of Formula IV-Ac | Compound |
|---|---|
| H | Compound HO-IV-Ac |

Step (iv)(D)

In some embodiments, reacting a compound of Formula IIIB-Ac with tert-butylmagnesium halide provides a compound of Formula IV-Ac. In certain embodiments, reacting Compound AcO-IIIB-Ac with tert-butylmagnesium halide provides Compound HO-IV-Ac. See, Example 45.

In some embodiments, the tert-butylmagnesium halide is tert-butylmagnesium chloride or tert-butylmagnesium bromide. In some embodiments, the reaction is performed in a solvent comprising a nonpolar solvent, e.g., tert-butylmethyl ether, 2-methyl-tetrahydrofuran, diethyl ether, dimethoxymethane, benzene, toluene, or a mixture of thereof.

In some embodiments, the tert-butylmagnesium halide is reacted at a temperature within the range of about 15° C. to about 40° C., e.g., about 20° C. to about 40° C., or about 25° C. to about 40° C., or about 30° C. to about 40° C., or about 15° C. to about 35° C., or about 15° C. to about 30° C., or about 15° C. to about 25° C., or about 20° C. to about 35° C., or about 25° C. to about 30° C. In some embodiments, the tert-butylmagnesium halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 2 hours to about 6.5 hours, or about 2.5 hours to about 6 hours, or about 3 hours to about 5.5 hours.

Formula IIIA-MCP→Formula IV-Ac

Step (iv)(C)

In some embodiments, reacting a compound of Formula IIIA-Ac with $H_2$ in the presence of a hydrogenation catalyst provides a compound of Formula IV-Ac. In certain embodiments, reacting Compound HO-IIIA-Ac with $H_2$ in the presence of a hydrogenation catalyst provides Compound HO-IV-Ac. See, Example 46.

In some embodiments, the hydrogenation catalyst comprises nickel, palladium, platinum, rhodium, or ruthenium. In some embodiments, the hydrogenation catalyst comprises platinum or palladium, supported on carbon. In some embodiments, the reaction is performed in a solvent comprising a polar protic or aprotic solvent, e.g., n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

In some embodiments, the hydrogen is reacted at a temperature within the range of about 15° C. to about 120° C., e.g., about 20° C. to about 120° C., or about 30° C. to about 120° C., or about 40° C. to about 120° C., or about 15° C. to about 115° C., or about 20° C. to about 110° C., or about 30° C. to about 105° C., or about 40° C. to about 115° C., or about 50° C. to about 110° C. In some embodiments, the hydrogen is reacted for a period of time within the range of about 6 hours to about 3 days, e.g., about 12 hours to about 3 days, or about 18 hours to about 3 days, or about 1 day to about 3 days, or about 1.25 days to about 3 days, or about 1.5 days to about 3 days, or about 6 hours to about 2.75 days, or about 6 hours to about 2.5 days, or about 6 hours to about 2.25 days, or about 6 hours to about 2 day, or about 6 hours to about 36 hours, or about 12 hours to about 2.5 days, or about 24 hours to about 2 days. In some embodiments, the hydrogen is reacted at a pressure within the range of about 1 atm to about 3 atm, e.g., about 1.25 atm to about 3 atm, or about 1.5 atm to about 3 atm, or about 1.75 atm to about 3 atm, or about 2 atm to about 3 atm, or about 1 atm to about 2.75 atm, or about 1 atm to about 2.5 atm, or about 1 atm to about 2.25 atm, or about 1 atm to about 2 atm, or about 1.25 atm to about 2.75 atm, or about 1.5 atm to about 2.5 atm, or about 1.75 atm to about 2.25 atm.

Formula IIIA-Bn→Formula IV-H

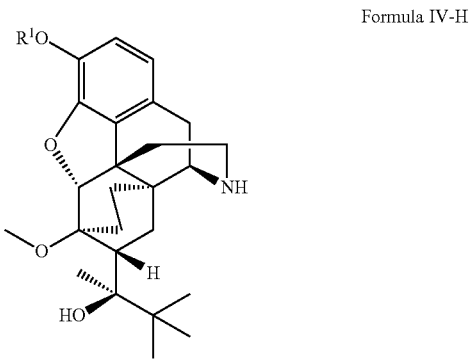

Formula IV-H

| $R^1$ of Formula IV-H | Compound |
|---|---|
| H | HO-IV-H |

Step (iv)(C), Step (v)(C), Step (vi)(C)

In some embodiments, reacting a compound of Formula IIIA-Bn with $H_2$ in the presence of a hydrogenation catalyst provides a compound of Formula IV-Bn. In certain embodiments, reacting Compound BnO-IIIA-Bn with $H_2$ in the presence of a hydrogenation catalyst provides Compound HO-IV-H. See Example 34. In certain embodiments, reacting Compound HO-IIIA-Bn with $H_2$ in the presence of a hydrogenation catalyst provides Compound HO-IV-H. See Examples 34 and 43.

In some embodiments, the hydrogenation catalyst comprises nickel, palladium, platinum, rhodium, or ruthenium. In some embodiments, the hydrogenation catalyst comprises platinum or palladium, supported on carbon. In some embodiments, the reaction is performed in a solvent comprising a polar protic or aprotic solvent, e.g., n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

In some embodiments, the hydrogen is reacted at a temperature within the range of about 15° C. to about 120° C., e.g., about 20° C. to about 120° C., or about 30° C. to about 120° C., or about 40° C. to about 120° C., or about 15° C. to about 115° C., or about 20° C. to about 110° C., or about 30° C. to about 105° C., or about 40° C. to about 115° C., or about 50° C. to about 110° C. In some embodiments, the hydrogen is reacted for a period of time within the range of about 6 hours to about 3 days, e.g., about 12 hours to about 3 days, or about 18 hours to about 3 days, or about 1 day to about 3 days, or about 1.25 days to about 3 days, or about 1.5 days to about 3 days, or about 6 hours to about 2.75 days, or about 6 hours to about 2.5 days, or about 6 hours to about 2.25 days, or about 6 hours to about 2 day, or about 6 hours to about 36 hours, or about 12 hours to about 2.5 days, or about 24 hours to about 2 days. In some embodiments, the hydrogen is reacted at a pressure within the range of about 1 atm to about 3 atm, e.g., about 1.25 atm to about 3 atm, or about 1.5 atm to about 3 atm, or about 1.75 atm to about 3 atm, or about 2 atm to about 3 atm, or about 1 atm to about 2.75 atm, or about 1 atm to about 2.5 atm, or about 1 atm to about 2.25 atm, or about 1 atm to about 2 atm, or about 1.25 atm to about 2.75 atm, or about 1.5 atm to about 2.5 atm, or about 1.75 atm to about 2.25 atm.

Formula IV-Ac→Formula IV-H

Step (v)(I)

In some embodiments, reacting a compound of Formula IV-Ac with Schwartz's reagent (zirconocene hydrochloride) or base provides a compound of Formula IV-H. In certain embodiments, reacting Compound HO-IV-Ac with Schwartz's reagent or base provides Compound HO-IV-H. See Examples 47 and 48.

In some embodiments, the reaction with Schwartz's reagent is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the Schwartz's reagent is reacted at a temperature within the range of about 15° C. to about 40° C., e.g., about 20° C. to about 40° C., or about 25° C. to about 40° C., or about 30° C. to about 40° C., or about 15° C. to about 35° C., or about 15° C. to about 30° C., or about 15° C. to about 25° C., or about 20° C. to about 35° C., or about 25° C. to about 30° C. In some embodiments, the Schwartz's reagent is reacted for a period of time within the range of about 5 minutes to about 3 hours, e.g., or about 10 minutes to about 3 hours, or about 15 minutes to about 3 hours, or about 30 minutes to about 3 hours, or about 45 minutes to about 3 hours, or about 1 hour to about 3 hours, or about 1.25 hours to about 3 hours, or about 1.5 hours to about 3 hours, or about 1.75 hours to about 3 hours, or about 2 hours to about 3 hours, or about 5 minutes to about 2.75 hours, or about 5 minutes to about 2.5 hours, or about 5 minutes to about 2.25 hours, or about 5 minutes to about 2 hours, or about 5 minutes to about 1.75 hours, or about 5 minutes to about 1.5 hours, or about 5 minutes to about 1.25 hours, or about 5 minutes to about 1 hour, or about 10 minutes to about 2.75 hours, or about 15 minutes to about 2.5 hours, or about 30 minutes to about 2.25 hours, or about 45 minutes to about 2 hours, or about 1 hour to about 1.75 hours.

In some embodiments, the base is an inorganic base, e.g., potassium hydroxide or sodium hydroxide. In some embodiments, the reaction with base is performed in a solvent comprising a high-boiling-point polar protic or aprotic solvent, e.g., ethylene glycol, diethylene glycol, N-methylpyrrolidone, dimethylformamide, or dimethylsulfoxide.

In some embodiments, the base is reacted at a temperature within the range of about 50° C. to about 240° C., e.g., about 60° C. to about 240° C., or about 70° C. to about 240° C., or about 80° C. to about 240° C., or about 90° C. to about 240° C., or about 100° C. to about 240° C., or about 110° C. to about 240° C., or about 120° C. to about 240° C., or about 130° C. to about 240° C., or about 140° C. to about 240° C., or about 150° C. to about 240° C., or about 50° C. to about 230° C., or about 50° C. to about 220° C., or about 50° C. to about 2100° C., or about 50° C. to about 2000° C., or about 50° C. to about 190° C., or about 50° C. to about 180° C., or about 90° C. to about 210° C., or about 100° C. to about 200° C. In some embodiments, the base is reacted for a period of time within the range of about 4 hours to about 2 days, e.g., about 8 hours to about 2 days, or about 12 hours to about 2 days, or about 16 hours to about 2 days, or about 20 hours to about 2 days, or about 1 day to about 2 days, or about 1.25 days to about 2 days, or about 1.5 days to about 2 days, or about 4 hours to about 1.75 days, or about 4 hours to about 1.5 days, or about 4 hours to about 1.25 days, or about 4 hours to about 1 day, or about 4 hours to about 20 hours, or about 4 hours to about 16 hours, or about 4 hours to about 12 hours, or about 8 hours to about 1.75 days, or about 12 hours to about 1.5 days, or about 16 hours to about 1.25 days.

Formula IV-H→Formula IV-MCP
Step (v)(A1), Step (vi)(A1)

In some embodiments, reacting a compound of Formula IV-H with cyclopropane carboxaldehyde followed by a hydride source provides a compound of Formula IV-MCP. In certain embodiments, reacting Compound HO-IV-H with cyclopropane carboxaldehyde followed by a hydride source provides buprenoprhine. See Example 35.

In some embodiments, the hydride source is formic acid, hydrogen, sodium cyanoborohydride, sodium borohydride, or sodium triacetoxy borohydride. In some embodiments, the hydride source is formic acid. In some embodiments, the reaction is catalyzed by a ruthenium(I) complex or a ruthenium(II) complex, e.g., a dichloro(p-cymene)ruthenium(II) dimer. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof. In some embodiments, the reaction is performed in the presence of a trialkylamine, e.g., triethylamine, diisopropylethylamine, 4-methyl-morpholine, or N-methyl-piperidine.

In some embodiments, the cyclopropane carboxaldehyde is reacted at a temperature within the range of about 30° C. to about 90° C., e.g., about 35° C. to about 90° C., or about 40° C. to about 90° C., or about 45° C. to about 90° C., or about 50° C. to about 90° C., or about 55° C. to about 90° C., or about 60° C. to about 90° C., or about 65° C. to about 90° C., or about 70° C. to about 90° C., or about 30° C. to about 85° C., or about 30° C. to about 80° C., or about 30° C. to about 75° C., or about 30° C. to about 70° C., or about 30° C. to about 65° C., or about 30° C. to about 60° C., or about 30° C. to about 55° C., or about 30° C. to about 50° C., or about 35° C. to about 85° C., or about 40° C. to about 80° C., or about 45° C. to about 75° C., or about 50° C. to about 70° C., or about 55° C. to about 65° C. In some embodiments, the cyclopropane carboxaldehyde is reacted for a period of time within the range of about 30 minutes to about 5 hours, e.g., about 1 hour to about 5 hours, or about 1.5 hours to about 5 hours, or about 2 hours to about 5 hours, or about 2.5 hours to about 5 hours, or about 3 hours to about 5 hours, or about 3.5 hours to about 5 hours, or about 4 hours to about 5 hours, or about 30 minutes to about 4.5 hours, or about 30 minutes to about 4 hours, or about 30 minutes to about 3.5 hours, or about 30 minutes to about 3 hours, or about 30 minutes to about 2.5 hours, or about 30 minutes to about 2 hours, or about 30 minutes to about 1.5 hours.

Step (v)(A2), Step (vi)(A2)

In some embodiments, reacting a compound of Formula IV-H with cyclopropanecarboxylic acid halide followed by a reducing agent provides a compound of Formula IV-MCP. In certain embodiments, reacting Compound HO-IV-H with cyclopropanecarboxylic acid halide followed by a reducing agent provides buprenorphine.

In some embodiments, the cyclopropanecarboxylic acid halide is cyclopropanecarboxylic acid chloride, cyclopropanecarboxylic acid anhydride, cyclopropanecarboxylic acid bromide, or an activated cyclopropanecarboxylic acid (e.g., an activated cyclopropanecarboxylic acid formed by reaction with an alcohol such as pentafluorophenol, 4-nitrophenol, N-hydroxysuccinimide, N-hydroxymaleimide, 1-Hydroxybenzotriazole, or 1-hydroxy-7-azabenzotriazole). In some embodiments, the reducing agent is LiAlH$_4$ or NaBH$_4$. In some embodiments, the reaction with cyclopropanecarboxylic acid halide is performed in a solvent comprising a nonpolar solvent, e.g., dichloromethane, chloroform, toluene, 1,4-dioxane, diethyl ether, benzene, or a mixture thereof. In some embodiments, the reaction with a reducing agent is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the cyclopropanecarboxylic acid halide is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 20° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the cyclopropanecarboxylic acid halide is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days. In some embodiments, the reducing agent is reacted at a temperature within the range of about 35° C. to about 85° C., e.g., about 40° C. to about 85° C., or about 45° C. to about 85° C., or about 50° C. to about 85° C., or about 55° C. to about 85° C., or about 60° C. to about 85° C., or about 65° C. to about 85° C., or about 35° C. to about 80° C., or about 35° C. to about 75° C., or about 35° C. to about 70° C., or about 35° C. to about 65° C., or about 35° C. to about 60° C., or about 35° C. to about 55° C., or about 40° C. to about 80° C., or about 45° C. to about 75° C., or about 50° C. to about 70° C., or about 55° C. to about 65° C. In some embodiments, the reducing agent is reacted for a period of time within the range of about 5 minutes to about 3 hours, e.g., or about 10 minutes to about 3 hours, or about 15 minutes to about 3 hours, or about 30 minutes to about 3 hours, or about 45 minutes to about 3 hours, or about 1 hour to about 3 hours, or about 1.25 hours to about 3 hours, or about 1.5 hours to about 3 hours, or about 1.75 hours to about 3 hours, or about 2 hours to about 3 hours, or about 5 minutes to about 2.75 hours, or about 5 minutes to about 2.5 hours, or about 5 minutes to about 2.25 hours, or about 5 minutes to about 2 hours, or about 5 minutes to about 1.75 hours, or about 5 minutes to about 1.5 hours, or about 5 minutes to about 1.25 hours, or about 5 minutes to about 1 hour, or about 10 minutes to about 2.75 hours, or about 15 minutes to about 2.5 hours, or about 30 minutes to about 2.25 hours, or about 45 minutes to about 2 hours, or about 1 hour to about 1.75 hours.

Step (v)(A3), Step (vi)(A3)

In some embodiments, reacting a compound of Formula IV-H with cyclopropylmethyl halide or activated cyclopropane methanol (e.g., activated with a sulfonate group such as a p-toluene sulfonyl group or a methyl sulfonyl group, or with triphenylphosphine) provides a compound of Formula IV-MCP. In certain embodiments, reacting Compound HO-IV-H with cyclopropylmethyl halide or activated cyclopropane methanol provides buprenorphine.

In some embodiments, the cyclopropylmethyl halide is cyclopropylmethyl chloride or cyclopropylmethyl bromide. In some embodiments, the reaction is performed in the presence of a trialkylamine, e.g., triethylamine, diisopropylethylamine, 4-methyl-morpholine, or N-methyl-piperidine. In some embodiments, the reaction is performed in a solvent comprising a polar protic solvent, e.g., n-butanol, isopropanol, ethanol, methanol, water, or a mixture thereof.

In some embodiments, the cyclopropylmethyl halide or activated cyclopropane methanol is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the cyclopropylmethyl halide or activated cyclopropane methanol is reacted for a period of time within the range of about 30 minutes to about 6 hours, e.g., about 1 hours to about 6 hours, or about 1.5 hours to about 6 hours, or about 2 hours to about 6 hours, or about 2.5 hours to about 6 hours, or about 3 hours to about 6 hours, or about 3.5 hours to about 6 hours, or about 4 hours to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 30 minutes to about 3 hours, or about 30 minutes to about 2.5 hours, or about 1 hours to about 5.5 hours, or about 1.5 hours to about 5 hours, or about 2 hours to about 4.5 hours, or about 2.5 hours to about 4 hours.

Formula IV-MCP→Formula IV-MCP

Step (v)(E)

In some embodiments, reacting a compound of Formula IV-MCP with a demethylating agent provides another compound of Formula IV-MCP. In certain embodiments, reacting Compound MeO-IV-MCP with a demethylating agent provides buprenorphine. See Example 10.

In some embodiments, the demethylating agent is a thiolate, e.g., a dodecane thiolate. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the demethylating agent is reacted at a temperature within the range of about 50° C. to about 190° C., e.g., about 60° C. to about 190° C., or about 70° C. to about 190° C., or about 80° C. to about 190° C., or about 90° C. to about 190° C., or about 100° C. to about 190° C., or about 110° C. to about 190° C., or about 120° C. to about 190° C., or about 130° C. to about 190° C., or about 140° C. to about 190° C., or about 150° C. to about 190° C., or about 50° C. to about 180° C., or about 50° C. to about 170° C., or about 50° C. to about 160° C., or about 50° C. to about 150° C., or about 50° C. to about 140° C., or about 50° C. to about 130° C., or about 50° C. to about 120° C., or about 50° C. to about 110° C., or about 50° C. to about 100° C., or about 50° C. to about 90° C., or about 60° C. to about 180° C., or about 70° C. to about 170° C., or about 80° C. to about 160° C., or about 90° C. to about 150° C., or about 100° C. to about 140° C. In some embodiments, the demethylating agent is reacted for a period of time within the range of about 4 hours to about 2 days, e.g., about 8 hours to about 2 days, or about 12 hours to about 2 days, or about 16 hours to about 2 days, or about 20 hours to about 2 days, or about 1 day to about 2 days, or about 1.25 days to about 2 days, or about 1.5 days to about 2 days, or about 4 hours to about 1.75 days, or about 4 hours to about 1.5 days, or about 4 hours to about 1.25 days, or about 4 hours to about 1 day, or about 4 hours to about 20 hours, or about 4 hours to about 16 hours, or about 4 hours to about 12 hours, or about 8 hours to about 1.75 days, or about 12 hours to about 1.5 days, or about 16 hours to about 1.25 days.

Formula I-H→Buprenorphine

In one aspect, the method of preparing buprenorphine comprises the series of steps provided in Table 1:

TABLE 1

| 4-step buprenorphine route | | | |
|---|---|---|---|
| No. | Substrate | Step | Product |
| i | Compound HO-I-H | (A1), (A2), or (A3) | Compound HO-I-MCP |
| ii | Compound HO-I-MCP | (B) | Compound HO-II-MCP |
| iii | Compound HO-II-MCP | (C) | Compound HO-IIIB-MCP |
| iv | Compound HO-IIIB-MCP | (D) | buprenorphine |

In another aspect, the method of preparing buprenorphine comprises the series of steps provided in Table 2:

TABLE 2

4-step buprenorphine route

| No. | Substrate | Step | Product |
|---|---|---|---|
| i | Compound HO-I-H | (A1), (A2), or (A3) | Compound HO-I-MCP |
| ii | Compound HO-I-MCP | (B) | Compound HO-II-MCP |
| iii | Compound HO-II-MCP | (D) | Compound HO-IIIA-MCP |
| iv | Compound HO-IIIA-MCP | (C) | buprenorphine |

In another aspect, the method of preparing buprenorphine comprises the series of steps provided in Table 3:

TABLE 3

4-step buprenorphine route

| No. | Substrate | Step | Product |
|---|---|---|---|
| i | Compound BnO-I-H | (A1), (A2), or (A3) | Compound BnO-I-MCP |
| ii | Compound BnO-I-MCP | (B) | Compound BnO-II-MCP |
| iii | Compound BnO-II-MCP | (D) | Compound BnO-IIIA-MCP |
| iv | Compound BnO-IIIA-MCP | (C) | buprenorphine |

In another aspect, the method of preparing buprenorphine comprises the series of steps provided in Table 4:

TABLE 4

5-step buprenorphine route

| No. | Substrate | Step | Product |
|---|---|---|---|
| i | Compound MeO-I-H | (A1), (A2), or (A3) | Compound MeO-I-MCP |
| ii | Compound MeO-I-MCP | (B) | Compound MeO-II-MCP |
| iii | Compound MeO-II-MCP | (C) | Compound MeO-IIIB-MCP |
| iv | Compound MeO-IIIB-MCP | (D) | Compound MeO-IV-MCP |
| v | Compound MeO-IV-MCP | (E) | buprenorphine |

In another aspect, the method of preparing buprenorphine comprises the series of steps provided in Table 5:

TABLE 5

5-step buprenorphine route

| No. | Substrate | Step | Product |
|---|---|---|---|
| i | Compound MeO-I-H | (A1), (A2), or (A3) | Compound MeO-I-MCP |
| ii | Compound MeO-I-MCP | (B) | Compound MeO-II-MCP |
| iii | Compound MeO-II-MCP | (D) | Compound MeO-IIIA-MCP |
| iv | Compound MeO-IIIA-MCP | (C) | Compound MeO-IV-MCP |
| v | Compound MeO-IV-MCP | (E) | buprenorphine |

In another aspect, the method of preparing buprenorphine comprises the series of steps provided in Table 6:

TABLE 6

5-step buprenorphine route

| No. | Substrate | Step | Product |
|---|---|---|---|
| i | Compound MeO-I-H | (A1), (A2), or (A3) | Compound MeO-I-MCP |
| ii | Compound MeO-I-MCP | (B) | Compound MeO-II-MCP |
| iii | Compound MeO-II-MCP | (D) | Compound MeO-IIIA-MCP |
| iv | Compound MeO-IIIA-MCP | (E) | Compound HO-IIIA-MCP |
| v | Compound HO-IIIA-MCP | (C) | buprenorphine |

In another aspect, the method of preparing buprenorphine comprises the series of steps provided in Table 7:

TABLE 7

6-step buprenorphine route

| No. | Substrate | Step | Product |
|---|---|---|---|
| i | Compound HO-I-Me | (F) | Compound BnO-I-Me |
| ii | Compound BnO-I-Me | (E) | Compound BnO-I-H |
| iii | Compound BnO-I-H | (A1), (A2), or (A3) | Compound BnO-I-MCP |
| iv | Compound BnO-I-MCP | (B) | Compound BnO-II-MCP |
| v | Compound BnO-II-MCP | (D) | Compound BnO-IIIA-MCP |
| vi | Compound BnO-IIIA-MCP | (C) | buprenorphine |

In another aspect, the method of preparing buprenorphine comprises the series of steps provided in Table 8:

TABLE 8

5-step buprenorphine route

| No. | Substrate | Step | Product |
|---|---|---|---|
| i | Compound HO-I-H | (A1), (A2), or (A3) | Compound HO-I-MCP |
| ii | Compound HO-I-MCP | (B) | Compound HO-II-MCP |
| iii | Compound HO-II-MCP | (F) | Compound BnO-II-MCP |
| iv | Compound BnO-II-MCP | (D) | Compound BnO-IIIA-MCP |
| v | Compound BnO-IIIA-MCP | (C) | buprenorphine |

In another aspect, the method of preparing buprenorphine comprises the series of steps provided in Table 9:

TABLE 9

5-step buprenorphine route

| No. | Substrate | Step | Product |
|---|---|---|---|
| i | Compound HO-I-H | (A1), (A2), or (A3) | Compound HO-I-MCP |
| ii | Compound HO-I-MCP | (F) | Compound BnO-I-MCP |
| iii | Compound BnO-I-MCP | (B) | Compound BnO-II-MCP |
| iv | Compound BnO-II-MCP | (D) | Compound BnO-IIIA-MCP |
| v | Compound BnO-IIIA-MCP | (C) | buprenorphine |

In another aspect, the method of preparing buprenorphine comprises the series of steps provided in Table 10:

TABLE 10

5-step buprenorphine route

| No. | Substrate | Step | Product |
|---|---|---|---|
| i | Compound HO-I-H | (F) | Compound BnO-I-Bn |
| ii | Compound BnO-I-Bn | (B) | Compound BnO-II-Bn |
| iii | Compound BnO-II-Bn | (D) | Compound BnO-IIIA-Bn |
| iv | Compound BnO-IIIA-Bn | (C) | Compound HO-IV-H |
| v | Compound HO-IV-H | (A1), (A2), or (A3) | buprenorphine |

In another aspect, the method of preparing buprenorphine comprises the series of steps provided in Table 11:

TABLE 11

7-step buprenorphine route

| No. | Substrate | Step | Product |
|---|---|---|---|
| i | Compound HO-I-H | (G) | Compound HO-I-Ac |
| ii | Compound HO-I-Ac | (F) | Compound BnO-I-Ac |
| iii | Compound BnO-I-Ac | (H) | Compound BnO-I-Bn |
| iv | Compound BnO-I-Bn | (B) | Compound BnO-II-Bn |
| v | Compound BnO-II-Bn | (D) | Compound BnO-IIIA-Bn |
| vi | Compound BnO-IIIA-Bn | (C) | Compound HO-IV-H |
| vii | Compound HO-IV-H | (A1), (A2), or (A3) | buprenorphine |

In another aspect, the method of preparing buprenorphine comprises the series of steps provided in Table 12:

TABLE 12

6-step buprenorphine route

| No. | Substrate | Step | Product |
|---|---|---|---|
| i | Compound HO-I-H | (G) | Compound AcO-I-Ac |
| ii | Compound AcO-I-Ac | (B) | Compound AcO-II-Ac |
| iii | Compound AcO-II-Ac | (D) | Compound HO-IIIA-Ac |
| iv | Compound HO-IIIA-Ac | (H) | Compound HO-IIIA-Bn |
| v | Compound HO-IIIA-Bn | (C) | Compound HO-IV-H |
| vi | Compound HO-IV-H | (A1), (A2), or (A3) | Buprenorphine |

In another aspect, the method of preparing buprenorphine comprises the series of steps provided in Table 13:

TABLE 13

6-step buprenorphine route

| No. | Substrate | Step | Product |
|---|---|---|---|
| i | Compound HO-I-H | (G) | Compound AcO-I-Ac |
| ii | Compound AcO-I-Ac | (B) | Compound AcO-II-Ac |
| iii | Compound AcO-II-Ac | (D) | Compound HO-IIIA-Ac |
| iv | Compound HO-IIIA-Ac | (C) | Compound HO-IV-Ac |
| v | Compound HO-IV-Ac | (I) | Compound HO-IV-H |
| vi | Compound HO-IV-H | (A1), (A2), or (A3) | Buprenorphine |

In another aspect, the method of preparing buprenorphine comprises the series of steps provided in Table 14:

TABLE 14

6-step buprenorphine route

| No. | Substrate | Step | Product |
|---|---|---|---|
| i | Compound HO-I-H | (G) | Compound AcO-I-Ac |
| ii | Compound AcO-I-Ac | (B) | Compound AcO-II-Ac |
| iii | Compound AcO-II-Ac | (C) | Compound AcO-IIIB-Ac |
| iv | Compound AcO-IIIB-Ac | (D) | Compound HO-IV-Ac |
| v | Compound HO-IV-Ac | (I) | Compound HO-IV-H |
| vi | Compound HO-IV-H | (A1), (A2), or (A3) | Buprenorphine |

The person of ordinary skill in the art will appreciate that additional steps such as, for example, purification (e.g., crystallization) or formation of an addition salt (e.g., formation of buprenorphine-HCl) may be included in the methods of the disclosure as otherwise described herein.

The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Reagents and solvents used in the Examples provided below are reagent grade (or higher) commercial products. Water utilized in the Examples was de-ionized. Northebaine and nororipavine were prepared according to literature procedures.

Preparation of Buprenorphine from Northebaine

Example 1. Preparation of Compound MeO-I-MCP (Step A1)

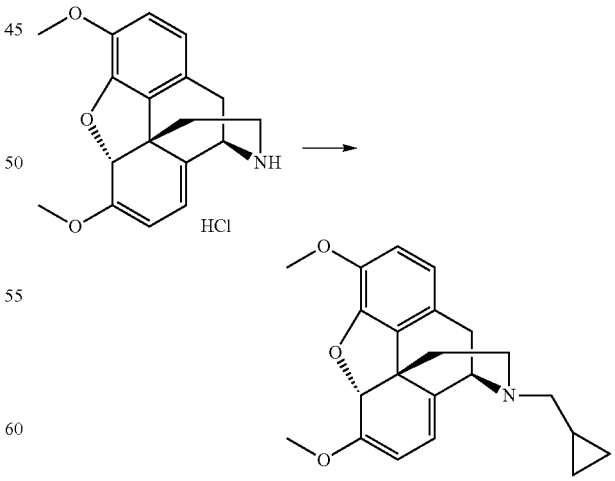

A 100 mL 3-necked flask was charged with Compound MeO-I-H (5.5 g, 16.5 mmol), cyclopropane carboxaldehyde (2.5 mL, 33 mmol), dichloro(p-cymene)ruthenium(II) dimer (100 mg, 0.165 mmol), triethylamine (13.75 mL, 99 mmol), and acetonitrile (50 mL) under a nitrogen atmosphere. The suspension was stirred at room temperature. Formic acid (7.78 mL, 206 mmol) was added slowly. The resulting mixture was heated at 60° C. for 2.5 h. The mixture was cooled to room temperature and concentrated under vacuum. The residue was partitioned between toluene and a 1 N NaOH aqueous solution. The aqueous layer was extracted twice with toluene. The combined organic layers were washed twice with water and then concentrated under vacuum to afford quantitatively Compound MeO-I-MCP (6.2 g).

N-cyclopropylmethyl-northebaine

HPLC 92.5% at 215 nm.
MS (ES-API pos) m/z 352.2 (M+H).
$^1$H NMR (300 MHz, CDCl$_3$) δ [ppm] 6.64 (d, J=8.2 Hz, 1H), 6.57 (d, J=8.2 Hz, 1H), 5.54 (d, J=6.5 Hz, 1H), 5.27 (s, 1H), 5.02 (d, J=6.5 Hz, 1H), 3.91 (d, J=6.4 Hz, 1H), 3.83 (s, 3H), 3.58 (s, 3H), 3.24 (d, J=18H, 1H), 2.65-2.87 (m, 3H), 2.47 (d, J=6.0 Hz, 2H), 2.19 (dt, J=5.8 and 12.3 Hz, 1H), 1.70 (d, J=12 Hz, 1H), 0.90 (m, 1H), 0.54 (m, 2H), 0.15 (m, 2H).
$^{13}$C NMR (75 MHz, CDCl$_3$) δ [ppm] 152.5, 142.8, 133.6, 132.6, 127.8, 119.2, 112.8, 111.7, 96.0, 89.2, 59.1, 58.6, 56.4, 54.9, 46.6, 44.3, 36.8, 30.6, 9.5, 3.9, 3.7.

Example 2. Preparation of Compound MeO-I-MCP (Step A2)

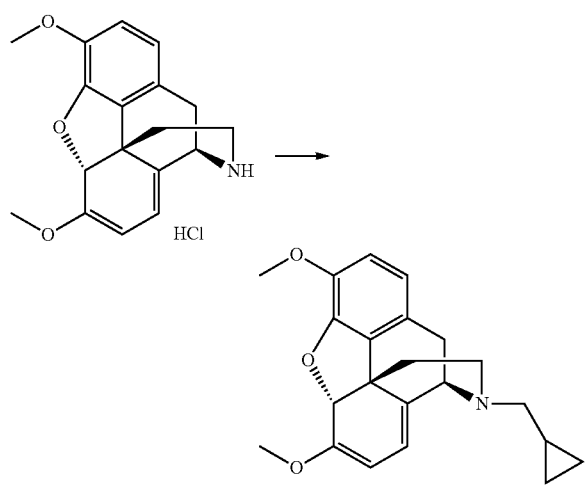

Triethylamine (1.6 mL, 12 mmol) was added to a suspension of Compound MeO-I-H (1.0 g, 3 mmol) in dichloromethane (25 mL). The mixture was cooled in an ice-water bath and cyclopropanecarboxylic acid chloride (0.35 mL, 3.6 mmol) was added dropwise. The cooling bath was removed and the mixture was stirred at room temperature overnight. The mixture was washed with a 1 N HCl aqueous solution, then with brine, dried with sodium sulfate and concentrated to a brown solid. The residue was dissolved in dry THF (10 mL) and slowly added to a stirred slurry of LiAlH$_4$ (0.20 g, 5.4 mmol) in anhydrous THF. The reaction mixture was heated at 60° C. for 1 h and then cooled in an ice-water bath. Wet diethyl ether was added to the mixture until there was no more bubbling. The mixture was filtered and the precipitate was washed several times with THF. The filtrate was concentrated under vacuum to give Compound MeO-I-MCP (0.80 g, 76%).

N-cyclopropylmethyl-northebaine

HPLC 89.8% at 215 nm.
NMR and MS data were in agreement with those obtained from Example 1.

Example 3. Preparation of Compound MeO-I-MCP (Step A3)

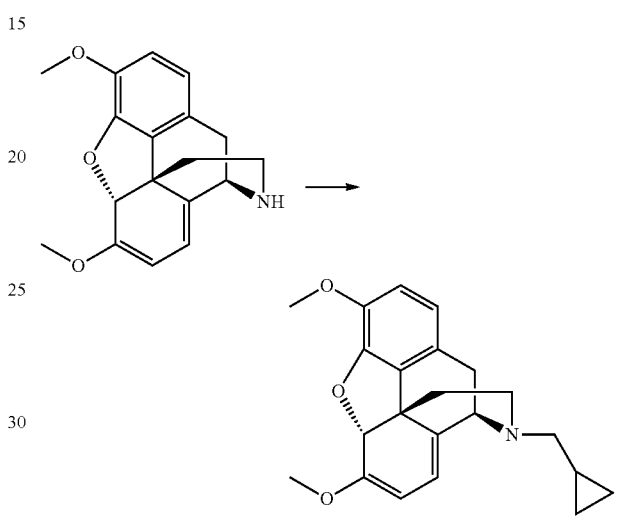

A 50 mL 3-necked flask was charged with Compound MeO-I-H (0.59 g, 2 mmol), cyclopropylmethylbromide (0.54 g, 4 mmol), triethylamine (0.5 g, 5 mmol) and ethanol (15 mL). The mixture was heated to reflux for 3 h. The ethanol was removed under vacuum and the residue was partitioned between dichloromethane and water. The organic layer was dried with sodium sulfate and concentrated under vacuum to obtain Compound MeO-I-MCP as light brown solid (0.60 g, 85% yield).

N-cyclopropylmethyl-northebaine

HPLC purity 97% at 215 nm.
MS (ES-API pos) m/z 352.3 (M+H).
NMR data was in agreement with those obtained from Example 1.

Example 4. Preparation of Compound MeO-II-MCP (Step B)

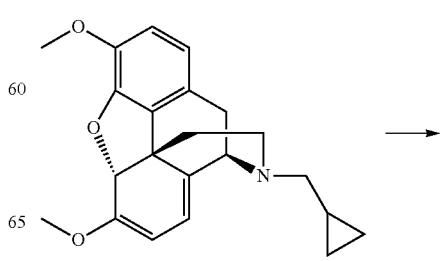

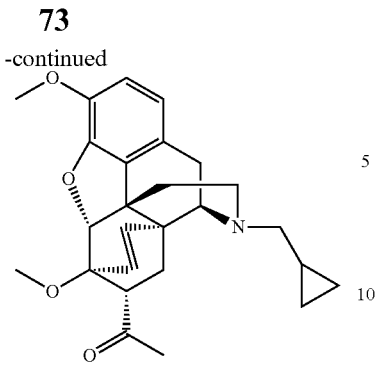

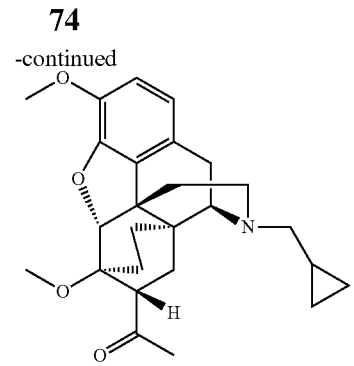

A solution of Compound MeO-I-MCP (5.8 g, 16.5 mmol) and methyl vinyl ketone (12 mL, 144 mmol) in toluene (100 mL) was heated at 80° C. for 16 h. After cooling to room temperature the mixture was concentrated under vacuum to give a brown oily residue (6.5 g), which was purified by column chromatography (120 g SiO$_2$, elution with 0-20% EtOAc in heptane, R$_f$ 0.3) to afford Compound MeO-II-MCP as a colorless solid (6.2 g, 89% yield).

7α-Acetyl-17-cyclopropylmethyl-6,14-endo(etheno)tetrahydro-northebaine

HPLC-purity 92.3% at 215 nm.

MS (ES-API pos) m/z 422.2 (M+H).

$^1$H NMR (300 MHz, CDCl$_3$) δ [ppm] 6.61 (d, J=8.2 Hz, 1H), 6.50 (d, J=8.2 Hz, 1H), 5.89 (d, J=8.8 Hz, 1H), 5.58 (d, J=8.8 Hz, 1H), 4.57 (s, 1H), 3.80 (s, 3H), 3.59 (s, 3H), 3.54 (d, J=6.4 Hz, 1H), 3.10 (d, J=18H, 1H), 2.89-3.03 (m, 2H), 2.66-2.72 (dd, J=4.7 and 11.8 Hz, 1H), 2.29-2.46 (m, 4H), 2.13 (s, 3H), 1.95 (dt, J=5.0 and 12.0 Hz, 1H), 1.83 (dd, J=2.3 and 12.9 Hz, 1H), 1.35 (dd, J=5.9 and 12.3 Hz, 1H), 0.81 (m, 1H), 0.51 (m, 2H), 0.12 (m, 2H).

$^{13}$C NMR (75 MHz, CDCl$_3$) δ [ppm] 209.2, 148.0, 141.7, 136.2 (−), 134.3, 128.3, 125.8 (−), 119.3 (−), 113.5 (−), 95.4 (−), 81.3, 59.8, 57.0 (−), 56.6 (−), 53.5 (−), 50.7 (−), 48.2, 44.0, 43.2, 33.6, 30.5 (−), 30.0, 23.2, 9.5 (−), 4.1, 3.4.

A vigorously stirred mixture of Compound MeO-II-MCP (1.1 g, 2.61 mmol) and Pd/C (10%, 50 mg) in iPrOH (20 mL) was hydrogenated at 80° C. for 16 h under 1 atm. H$_2$ using a hydrogen-filled balloon. The mixture was filtered over Celite and the solid washed with iPrOH. The filtrate was concentrated to 1.1 g oil, which was purified by column chromatography (40 g SiO$_2$, elution 0-25% EtOAc in heptane) to yield Compound MeO-IIIB-MCP (1.0 g, 90% yield).

7α-Acetyl-17-cyclopropylmethyl-6,14-endo(ethano)tetrahydro-northebaine

HPLC-purity 89.3% at 215 nm.

MS (ES-API pos) m/z 424.2 (M+H).

$^1$H NMR (300 MHz, CDCl$_3$) δ [ppm] 6.70 (d, J=7.8 Hz, 1H), 6.56 (d, J=7.8 Hz, 1H), 4.48 (s, 1H), 3.87 (s, 3H), 3.43 (s, 3H), 2.95-3.07 (m, 3H), 2.59-2.78 (m, 2H), 2.21-2.36 (m, 3H), 2.26 (s, 3H), 2.19 (dt, J=5.8 and 12.3 Hz, 1H), 1.51-1.76 (m, 4H), 1.25-1.35 (m, 2H), 0.65-0.85 (m, 2H), 0.48 (m, 2H), 0.09 (m, 2H).

$^{13}$C NMR (75 MHz, CDCl$_3$) δ [ppm] 210.9, 146.8, 141.7, 132.7, 128.8, 119.1, 114.0, 94.7, 77.5, 59.8, 58.4, 56.7, 52.2, 49.7, 46.4, 43.7, 35.4, 35.3, 33.8, 30.3, 28.7, 22.8, 17.4, 9.5, 4.0, 3.4.

Example 5. Preparation of Compound MeO-IIIB-MCP (Step C)

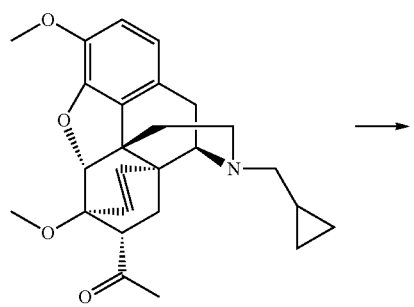 →

Example 6. Preparation of Compound MeO-IIIA-MCP (Step D)

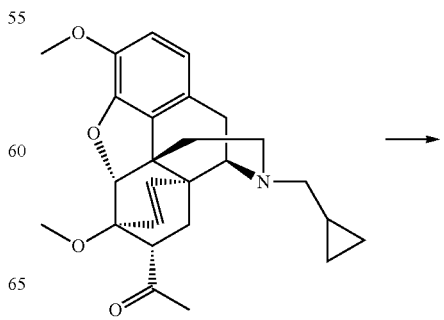 →

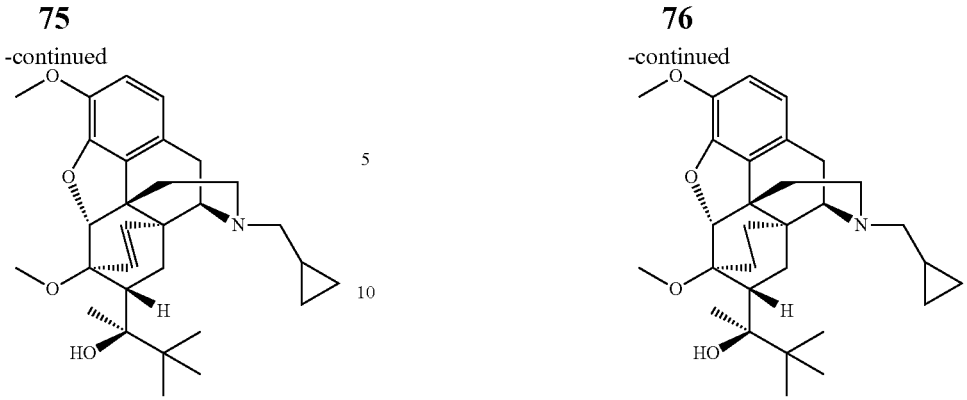

To a magnetically stirred solution of Compound MeO-II-MCP (2.1 g, 5 mmol) in toluene (50 mL) at room temperature was added a solution of tert-butylmagnesium chloride (1.7 M in THF, 20 mL, 34 mmol) over 5 min. The brown solution was stirred at room temperature for 4 h. The mixture was poured in a 10% ammonium chloride aqueous solution (100 mL) and the mixture was extracted with toluene. The extract was dried with sodium sulfate and concentrated to give a waxy solid. Purification by column chromatography (80 g $SiO_2$, 25% EtOAc in Heptane) gave Compound MeO-IIIA-MCP (1 g, 42% yield, $R_f$ 0.6) as a solid. Some starting material (0.32 g, 15%, $R_f$ 0.2) and reduced starting material (0.4 g, 18%, $R_f$ 0.1) were also recovered.

7α-(2-(S)-hydroxy-3,3-dimethyl-2-butyl)-17-cyclopropylmethyl-6,14-endo(etheno)tetrahydro-northebaine HPLC-purity 97.4% at 215 nm.

MS (ES-API pos) m/z 480.3 (M+H).

$^1$H NMR (300 MHz, $CDCl_3$) δ [ppm] 6.61 (d, J=8.2 Hz, 1H), 6.48 (d, J=8.2 Hz, 1H), 5.98 (d, J=8.8 Hz, 1H), 5.64 (s, 1H), 5.43 (d, J=8.8 Hz, 1H), 4.55 (s, 1H), 3.81 (s, 3H), 3.77 (s, 3H), 3.49 (d, J=6.4H, 1H), 3.09 (d, J=18 Hz, 1H), 2.97 (dd, J=12.3 and 8.8 Hz, 1H), 2.64 (m, 1H), 2.35-2.43 (m, 4H), 2.14 (t, J=8.8 Hz, 1H), 1.80-2.0 (m, 2H), 1.00 (s, 9H), 0.80-1.0 (m, 3H), 0.51 (m, 2H), 0.15 (m, 2H).

$^{13}$C NMR (75 MHz, $CDCl_3$) δ [ppm] 148.1, 141.7, 135.5, 134.7, 128.5, 124.8, 119.2, 113.7, 99.0, 84.5, 78.4, 59.5, 56.7, 55.2, 47.1, 45.8, 44.1, 43.1, 39.7, 34.0, 32.2, 26.6, 23.1, 19.6, 9.5, 4.3, 3.2.

Example 7. Preparation of Compound MeO-IV-MCP (Step D)

To a magnetically stirred solution of Compound MeO-IIIB-MCP (0.90 g, 2.1 mmol) in dry toluene (25 mL) at room temperature was added dropwise a solution of tert-butylmagnesium chloride (1.7 M solution in THF, 7.5 mL, 12.75 mmol). The reaction was quenched after 4 h by pouring the mixture into an aqueous solution made of 10% ammonium chloride (50 mL) and ice-water (50 mL). The layers were separated and the aqueous layer was extracted with toluene (3×25 mL). The combined organic layers were washed with brine, dried with sodium sulfate, and concentrated to an oil. Purification by column chromatography (80 g $SiO_2$, elution with 0-20% EtOAc in heptane, $R_f$ 0.5) to yield Compound MeO-IV-MCP as a waxy solid (0.60 g, 60% yield).

7α-(2-(S)-hydroxy-3,3-dimethyl-2-butyl)-17-cyclopropylmethyl-6,14-endo(ethano)tetrahydro-northebaine HPLC-purity 95.6% at 215 nm.

MS (ES-API pos) m/z 482.4 (M+H).

$^1$H NMR (300 MHz, $CDCl_3$) δ [ppm] 6.69 (d, J=8.2 Hz, 1H), 6.54 (d, J=8.2 Hz, 1H), 5.91 (s, 1H), 4.43 (s, 1H), 3.87 (s, 3H), 3.54 (s, 3H), 2.82-3.02 (m, 3H), 2.60 (dd, J=11.7 and 5.3H, 1H), 2.11-2.38 (m, 5H), 1.97 (dt, J=5.8 and 12.3 Hz, 1H), 1.60-1.85 (m, 3H), 1.36 (s, 3H), 1.25-1.30 (m, 1H), 1.00-1.12 (m, 1H), 1.03 (s, 9H), 0.70-0.83 (m, 2H), 0.48 (m, 2H), 0.10 (m, 2H).

$^{13}$C NMR (75 MHz, $CDCl_3$) δ [ppm] 146.9, 141.6, 132.9, 128.9, 119.1, 114.0, 96.7, 80.7, 79.3, 59.5, 58.3, 56.9, 52.6, 46.2, 43.9, 43.7, 40.4, 35.9, 35.8, 33.4, 29.7, 26.4, 22.8, 20.0, 18.2, 9.5, 4.2, 3.2.

Example 8. Preparation of Compound MeO-IV-MCP (Step C)

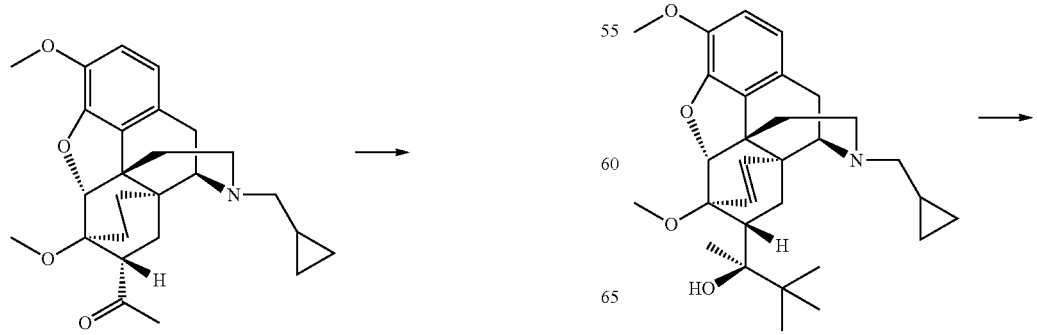

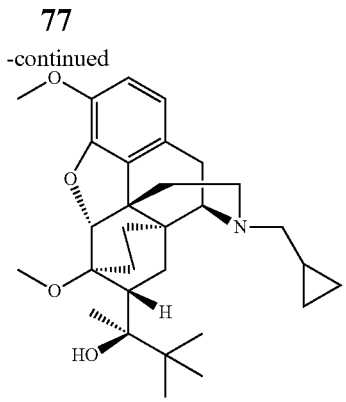

A vigorously stirred mixture of Compound MeO-IIIA-MCP (40 mg, 0.75 mmol), and Pd/C (10%, 10 mg) in iPrOH (10 mL) was hydrogenated at 80° C. for 16 h under 1 atmosphere of hydrogen. The mixture was filtered over Celite. The filtrate was concentrated to give Compound MeO-IV-MCP as a wax (40 mg, 100%).

7α-(2-(S)-hydroxy-3,3-dimethyl-2-butyl)-17-cyclopropylmethyl-6,14-endo(ethano)tetrahydro-northebaine HPLC-purity 83% at 254 nm.
MS (ES-API pos) m/z 482.3 (M+H).
The NMR data were in agreement with those obtained for Example 7.

Example 9. Preparation of Compound HO-IIIA-MCP (Step E)

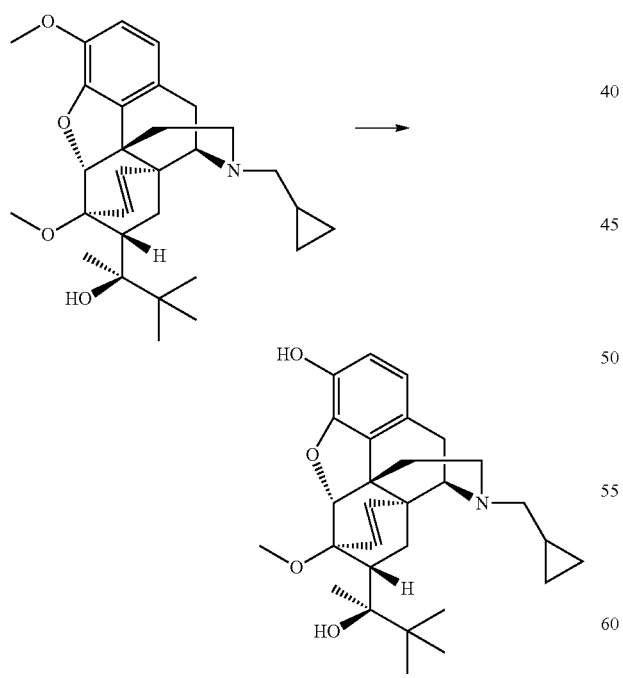

To a magnetically stirred solution of KOtBu (1.12 g, 10 mmol) and DMSO (10 mL) was added 1-dodecanethiol (2.03 g, 10 mmol). The resulting suspension was heated to 70° C. and a solution of Compound MeO-IIIA-MCP (0.90 g, 1.87 mmol) in DMSO (12 mL) was added. The resulting solution was heated at 110° C. for 16 h. The mixture was cooled to room temperature. Heptane (40 mL), EtOAc (10 mL) and a 1 N NH$_4$Cl aqueous solution (50 mL) were added. The layers were separated. The aqueous layer was washed twice with a heptane/EtOAc (4/1) mixture. The acidic aqueous layer was neutralized to pH 7-8 by careful addition of solid NaHCO$_3$ and extracted with EtOAc. The extract was washed with brine, dried with sodium sulfate and concentrated to an oil. Crystallization in MeOH and filtration afforded Compound HO-IIIA-MCP (240 mg, 28%) after drying. The mother liquor was concentrated and the residue purified by column chromatography to afford additional Compound HO-IIIA-MCP (270 mg, 31%), hence a total Compound HO-IIIA-MCP (510 mg, 59%) was obtained.

7α-(2-(S)-hydroxy-3,3-dimethyl-2-butyl)-17-cyclopropylmethyl-6,14-endo(etheno)tetrahydro-nororipavine HPLC-purity 94.1% at 215 nm.
MS (ES-API pos) m/z 466.2 (M+1).
$^1$H NMR (300 MHz, CDCl$_3$) δ [ppm] 6.58 (d, J=8.2 Hz, 1H), 6.44 (d, J=8.2 Hz, 1H), 5.96 (d, J=8.8 Hz, 1H), 5.64 (s, 1H), 5.43 (d, J=8.8 Hz, 1H), 4.89 (br s, 1H), 4.58 (s, 1H), 3.75 (s, 3H), 3.49 (d, J=6.0H, 1H), 3.08 (d, J=18 Hz, 1H), 2.97 (dd, J=12.3 and 8.8 Hz, 1H), 2.65 (m, 1H), 2.31-2.43 (m, 4H), 2.15 (t, J=8.8 Hz, 1H), 1.80-2.0 (m, 2H), 1.00 (s, 9H), 0.80-1.0 (m, 3H), 0.51 (m, 2H), 0.15 (m, 2H).
$^{13}$C NMR (75 MHz, CDCl$_3$) δ [ppm] 146.6, 137.2, 135.7, 134.5, 128.0, 124.4, 119.7, 116.0, 99.4, 84.5, 78.6, 59.5, 56.7, 55.2, 47.4, 45.8, 44.1, 43.1, 39.7, 33.9, 32.1, 26.6, 23.1, 19.6, 9.5, 4.3, 3.2.

Example 10. Preparation of Buprenorphine (Step E)

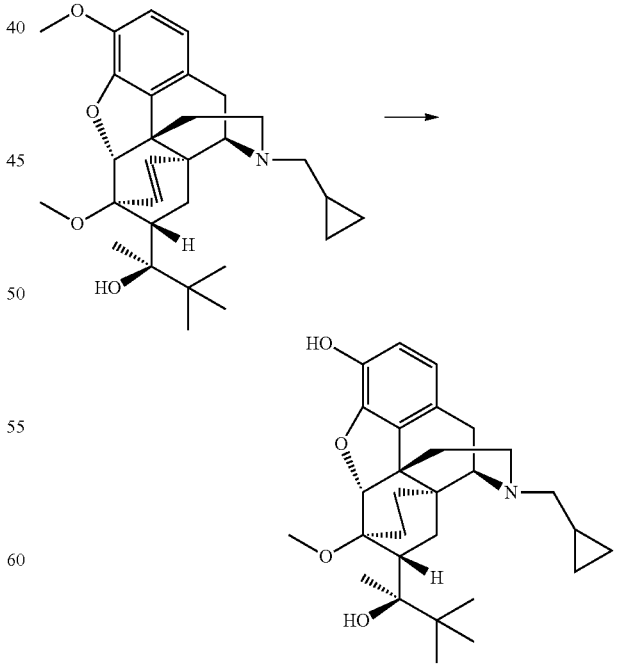

A 100 mL 3-necked flask was charged with KOtBu (200 mg, 1.8 mmol) and DMF (10 mL) under a nitrogen atmosphere, and the mixture was heated to 50° C. After the addition of 1-dodecanethiol (0.43 mL, 0.364 mg, 1.8 mmol) a white suspension was formed. Then a solution of Compound MeO-IV-MCP (600 mg, 1.28 mmol) in DMF (10 mL) was added and the resulting solution was heated at 120° C. for 16 h. The mixture was quenched by addition of 50 mL of a 10% citric acid solution to reach pH 4. The mixture was poured in water (50 mL) and washed with toluene (3×25 mL). The aqueous layer was neutralized to pH 7 by the addition of NaOH and extracted with EtOAc (3×25 mL). The combined extracts were dried with sodium sulfate and concentrated to an oil (0.35 g, 59% yield, HPLC 79% purity). Crystallization from wet MeOH (10 mL) gave crystalline buprenorphine (50 mg). The mother liquor was purified by column chromatography (12 g $SiO_2$, elution with 0-25% EtOAc in heptane) and provided additional buprenorphine as white solid (190 mg). A total of 240 mg of buprenorphine (40% yield) was obtained. Analytical data were in agreement with the literature.

Buprenorphine

HPLC-purity 98.8% at 215 nm.
DSC-Melting point 216.7° C. (Lit. 216-218).
MS (ES-API pos) m/z 468.4 (M+H).
$^1$H NMR (300 MHz, $CDCl_3$) δ [ppm] 6.68 (d, J=8.2 Hz, 1H), 6.51 (d, J=8.2 Hz, 1H), 5.88 (s, 1H), 4.88 (br s, 1H), 4.45 (s, 1H), 3.53 (s, 3H), 2.82-3.02 (m, 3H), 2.60 (dd, J=11.8 and 4.7H, 1H), 2.12-2.36 (m, 5H), 1.97 (dt, J=5.3 and 12.3 Hz, 1H), 1.60-1.85 (m, 3H), 1.36 (s, 3H), 1.26-1.36 (m, 1H), 1.03-1.11 (m, 1H), 1.03 (s, 9H), 0.69-0.82 (m, 2H), 0.48 (m, 2H), 0.10 (m, 2H).
$^{13}$C NMR (75 MHz, $CDCl_3$) δ [ppm] 145.4, 137.2, 132.6, 128.4, 119.6, 116.3, 97.1, 80.8, 79.5, 59.5, 58.3, 52.5, 46.5, 43.7, 43.7, 40.4, 36.0, 35.8, 33.4, 29.6, 26.4, 22.9, 20.1, 18.2, 9.5, 4.1, 3.2.

Example 11. Preparation of Buprenorphine (Step C)

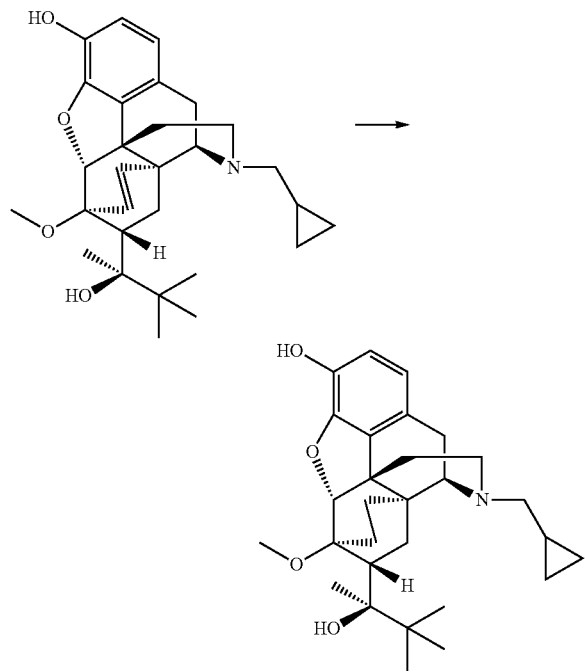

A vigorously stirred mixture of Compound HO-IIIA-MCP (350 mg, 0.75 mmol) and Pd/C (10%, 80 mg, 10 mol % Pd) in iPrOH (20 mL) and water (1 mL) was hydrogenated at 80° C. for 16 h under 1 atm. $H_2$ using a hydrogen-filled balloon. The mixture was filtered over Celite. The filtrate was concentrated to a white foam, which was taken up in MeOH (5 mL) and stirred for 1 h. The solid was collected by filtration and dried under vacuum to give buprenorphine as solid (165 mg, 47%). The mother liquor was concentrated to give more buprenorphine as a solid (180 mg, 51%). A total of 345 mg of buprenorphine (98% yield) was obtained.

Buprenorphine

HPLC-purity 86%.
MS and NMR data were in agreement with those obtained for Example 10.

Preparation of Buprenorphine from Nororipavine

Example 12. Preparation of Compound HO-I-MCP (Step A1)

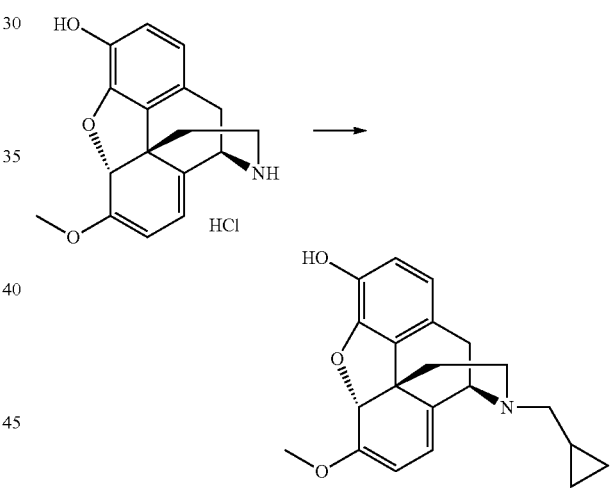

A 50 mL 3-neck round bottom flask was charged with Compound HO-I-H (910 mg, 3.21 mmol), cyclopropane carboxaldehyde (455 mg, 6.49 mmol), triethylamine (1.64 g, 16.22 mmol) and acetonitrile (9 mL), at room temperature and under a nitrogen atmosphere. To the stirred solution was added formic acid (2.4 mL) dropwise, over 10-15 min. After 10 min, di-µ-chlorobis[p-cymene)chlororuthenium(II)] (5 mg, 0.0082 mmol) was added and the mixture was stirred at 50° C. overnight. The volatiles were removed under vacuum and water (50 mL) was added to the resulting mixture. A 25% $NH_4OH$ aqueous solution (10 mL) was added and the aqueous mixture was extracted with $CHCl_3$ (3×50 mL). The combined organic layers were washed with brine (100 mL), dried over sodium sulfate, filtered off and the solvent was removed under vacuum. The crude product was purified by flash chromatography (0 to 10% MeOH in DCM) to afford Compound HO-I-MCP (1.07 g, 98%) was obtained as an off white solid.

(4R,7aR,12bS)-3-(Cyclopropylmethyl)-7-methoxy-2,3,4,7a-tetrahydro-1H-4,12-methanobenzofuro[3,2-e]isoquinolin-9-ol HPLC-purity 98.6% at 215 nm.

MS (ES-API pos) m/z 338.2 (M+H).

$^1$H NMR (300 MHz, CDCl$_3$) δ [ppm] 6.65 (d, J=8.4 Hz, 1H), 6.55 (d, J=8.4 Hz, 1H), 5.59 (d, J=6.6 Hz, 1H), 5.31 (s, 1H), 5.09 (d, J=6.6 Hz, 1H), 3.95 (d, J=6.6 Hz, 1H), 3.63 (s, 3H), 3.26 (d, J=18.0 Hz, 1H), 2.95 (dd, J=12.6, 4.2 Hz, 1H), 2.83 (m, 1H), 2.72 (dd, J=18.0, 7.2 Hz, 1H), 2.52 (m, 2H), 2.22 (dt, 1H), 1.75 (d, J=11.4 Hz, 1H), 0.93 (m, 1H), 0.56 (d, J=8.4 Hz, 2H), 0.18 (d, J=8.4 Hz, 2H).

$^{13}$C NMR (75 MHz, CDCl$_3$) δ [ppm] 151.9, 142.9, 138.3, 133.2, 132.9, 127.3, 119.7, 116.0, 111.5, 96.5, 89.7, 59.0, 58.5, 55.0, 46.9, 44.2, 36.7, 30.6, 9.4, 3.9, 3.8.

Example 13. Preparation of Compound HO-I-MCP (Step A2)

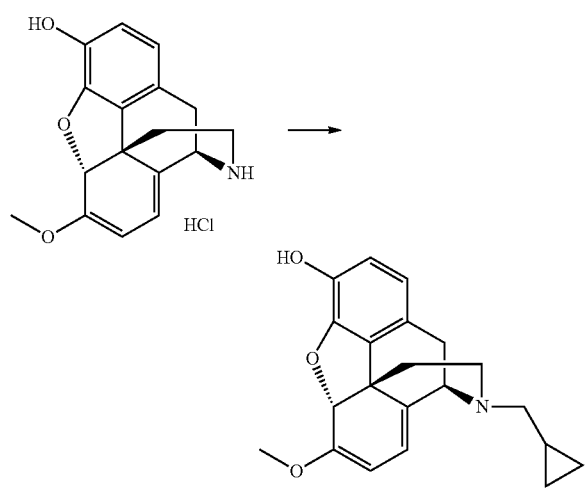

To a suspension of Compound HO-I-H (505 mg, 1.78 mmol) in CHCl$_3$ (14 mL) was added triethylamine (0.65 mL, 4.63 mmol) at room temperature and under a nitrogen atmosphere. The mixture was cooled to 0° C. with an ice/water bath and cyclopropane carboxylic acid chloride (440 mg, 4.12 mmol) dropwise. The mixture was stirred for 3 h at room temperature. The mixture was washed with a 1M HCl aqueous solution (30 mL), water (30 mL), dried over sodium sulfate and filtered off. The solvents were removed under vacuum. The brown residue was dissolved in THF (8 mL) then added dropwise to a slurry of LiAlH$_4$ (203 mg, 5.35 mmol) in THF (8 mL), at room temperature and under a nitrogen atmosphere. The mixture was then refluxed for 1.5 h. The mixture was cooled to 0° C. with an ice/water bath and carefully quenched with an ammonium chloride saturated aqueous solution. The mixture was diluted with THF (20 mL) and filtered off. The solid was washed with THF and the filtrate was concentrated under vacuum. The crude product Compound HO-I-MCP (500 mg, 83%) was obtained as an off white solid.

(4R,7aR,12bS)-3-(Cyclopropylmethyl)-7-methoxy-2,3,4,7a-tetrahydro-1H-4,12-methanobenzofuro[3,2-e]isoquinolin-9-ol HPLC-purity 94% at 215 nm.
NMR and MS data were in agreement with those obtained from Example 12.

Example 14. Preparation of Compound HO-I-MCP (Step A3)

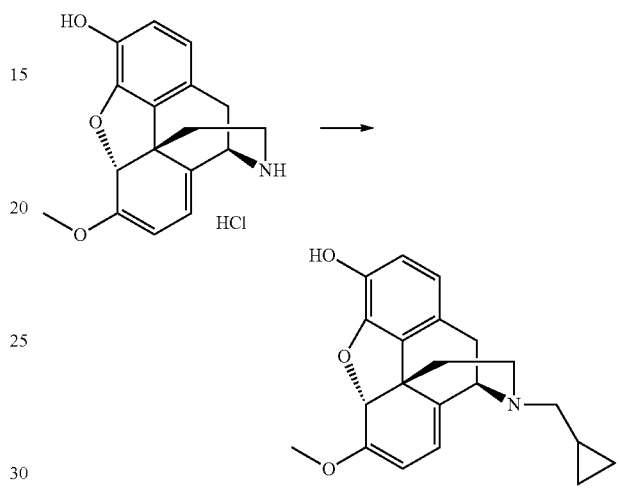

To a suspension or Compound HO-I-H (495 mg, 1.747 mmol) in EtOH (15 mL) were added triethylamine (0.61 mL, 4.37 mmol) and (bromomethyl)cyclopropane (0.35 mL, 3.494 mmol) at room temperature and under a nitrogen atmosphere. The mixture was refluxed overnight. The volatiles were removed under vacuum. Water (50 mL) and CHCl$_3$ (50 mL) were added. The aqueous phase was extracted with CHCl$_3$ (2×50 mL). The combined organic layers were dried over sodium sulfate, filtered off and the solvent was removed under vacuum. The crude product (510 mg) was purified by flash chromatography (0 to 10% MeOH in DCM) to afford Compound HO-I-MCP (370 mg, 63%) was obtained as an off white solid.

(4R,7aR,12bS)-3-(Cyclopropylmethyl)-7-methoxy-2,3,4,7a-tetrahydro-1H-4,12-methanobenzofuro[3,2-e]isoquinolin-9-ol HPLC-purity 94% at 215 nm.
NMR and MS data were in agreement with those obtained from Example 12.

Example 15. Preparation of Compound HO-II-MCP (Step B)

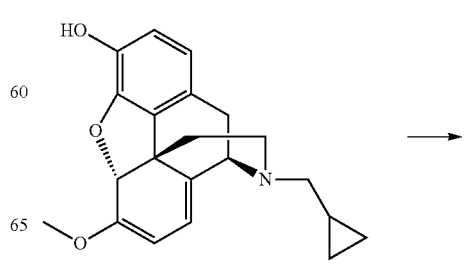

-continued

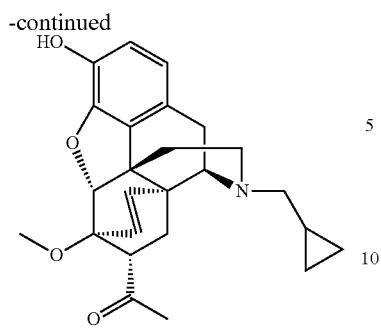

To a suspension of Compound HO-I-MCP (2.51 mg, 6.7 mmol) in toluene (50 mL) was added methyl vinyl ketone (12.2 mL, 139.1 mmol), at room temperature and under a nitrogen atmosphere. The reaction mixture was stirred at 80° C. overnight. The volatiles were removed under vacuum and the obtained crude material was triturated in hot EtOH, filtered off and washed with EtOH. Isolated Compound HO-II-MCP (1.88 g, 67%) was obtained as a beige solid. The mother liquor was concentrated under vacuum and the residue was purified by flash chromatography (0 to 5% MeOH in DCM). The obtained material was further triturated in hot EtOH and the solid was washed 3 times with EtOH prior to being isolated as additional Compound III-A (270 mg, 11%) as a beige solid (total amount: 2.15 g, 78%).

1-((4R,4aI,7I,7aI,12bI)-3-(Cyclopropylmethyl)-9-hydroxy-7-methoxy-1,2,3,4,7,7a-hexahydro-4a,7-ethano-4,12-methanobenzofuro[3,2-e]isoquinolin-14-yl)ethan-1-one HPLC-purity at 215 nm: 95.9% (1.88 g batch); 97.1% (270 mg batch).
MS (ES-API pos) m/z 408.2 (M+H).
$^1$H NMR (300 MHz, CDCl$_3$) δ [ppm] 6.6 (d, J=7.8 Hz, 1H), 6.46 (d, J=7.8 Hz, 1H), 5.83 (d, J=9.0 Hz, 1H), 5.57 (d, J=9.0 Hz, 1H), 4.58 (s, 1H), 3.6-3.53 (m, 4H), 3.09 (d, J=18.6 Hz, 1H), 3.08-2.87 (m, 2H), 2.76-2.62 (dd, J=12.0, 4.8 Hz, 1H), 2.5-2.24 (m, 4H), 2.12 (s, 3H), 1.95 (dt, J=13.2, 5.4 Hz, 1H), 1.83 (dd, J=12.6, 2.4 Hz, 1H), 1.34 (dd, J=12.6, 6.6 Hz, 1H), 0.9-0.72 (m, 1H), 0.6-0.42 (m, 2H), 0.22-0.06 (m, 2H).
$^{13}$C NMR (75 MHz, CDCl$_3$) δ [ppm] 209.3, 146.5, 137.6, 134.0, 127.5, 125.7, 119.9, 116.5, 94.8, 81.3, 59.7, 57.0, 52.9, 50.6, 48.4, 44.0, 43.2, 33.5, 30.1, 30.0, 23.2, 9.4, 4.1, 3.4.

Example 16. Preparation of Compound HO-IIIB-MCP (Step C)

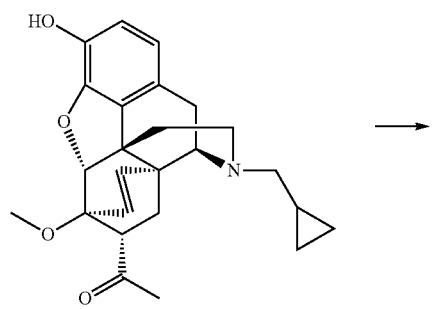

-continued

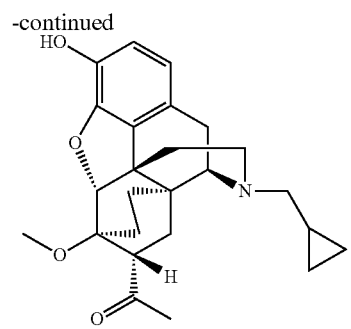

A 50 mL 3-neck round bottom flask was charged with Compound HO-II-MCP (800 mg, 1.963 mmol), tartaric acid (295 mg, 1.963 mmol), water (8 mL) and Pd/C (80 mg, 10% w/w). The mixture was then hydrogenated under 1 atmosphere of hydrogen at 80° C. for 12 h. The reaction mixture was filtered through Celite, while hot, and Celite was rinsed with some hot water. After cooling to room temperature, the pH of the aqueous solution was adjusted to 6.6-6.7 with 10% KOH. The aqueous solution was extracted with CHCl$_3$ (3×50 mL). The combined organic layers were dried over sodium sulfate, filtered off, and the solvent was removed under vacuum. Purification by flash chromatography (0 to 20% ethyl acetate in heptane) yielded Compound HO-IIIB-MCP (570 mg, 71%) as a white solid.

1-((4R,4aS,7R,7aR,12bS)-3-(Cyclopropylmethyl)-9-hydroxy-7-methoxy-1,2,3,4,5,6,7,7a-octahydro-4a,7-ethano-4,12-methanobenzofuro[3,2-e]isoquinolin-6-yl)ethan-1-one HPLC-purity 92.5% at 215 nm.
MS (ES-API pos) m/z 410.2 (M+H).
$^1$H NMR (300 MHz, CDCl$_3$) δ [ppm] 6.7 (d, J=8.1 Hz, 1H), 6.52 (d, J=8.1 Hz, 1H), 4.49 (s, 1H), 3.41 (s, 3H), 3.11-3.01 (m, 2H), 2.96 (d, J=18.3 Hz, 1H), 2.74 (dt, J=13.5, 11.4, 3.9 Hz, 1H), 2.64 (dd, J=12.0, 5.1 Hz, 1H), 2.56-2.28 (m, 7H), 2.04 (dt, J=12.6, 5.7 Hz, 1H), 1.76-1.4 (m, 4H), 1.38-1.21 (m, 1H), 0.96-0.62 (m, 2H), 0.56-0.41 (m, 2H), 0.15-0.05 (m, 2H).
$^{13}$C NMR (75 MHz, CDCl$_3$) δ [ppm] 210.9, 145.2, 137.4, 132.3, 128.1, 119.6, 116.6, 94.7, 77.8, 59.8, 58.3, 52.1, 49.5, 46.7, 43.7, 35.5, 35.1, 33.6, 30.4, 28.5, 22.8, 17.6, 9.4, 4.1, 3.3.

Example 17. Preparation of Compound HO-IIIB-MCP (Step C)

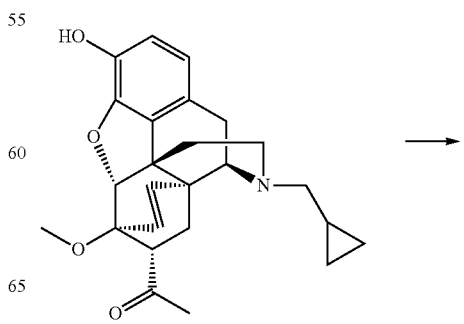

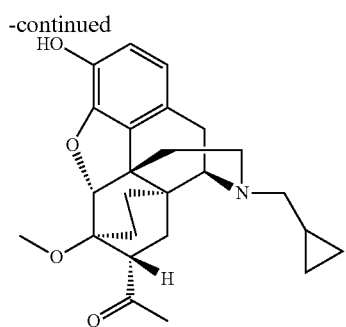

To a suspension of Compound HO-II-MCP (270 mg, 0.662 mmol) in a mixture of iPrOH (4.6 mL) and water (0.4 mL) was added Pd/C (30 mg, 10% w/w), at room temperature and under a nitrogen atmosphere. The mixture was then hydrogenated under 1 atmosphere of hydrogen at 80° C. overnight and was filtered off through Celite. Celite was rinsed with DCM. The filtrate was concentrated under vacuum and purification by flash chromatography (0 to 50% ethyl acetate in heptane) yielded Compound HO-IIIB-MCP (215 mg, 79%) as an off white solid.

1-((4R,4aS,7R,7aR,12bS)-3-(Cyclopropylmethyl)-9-hydroxy-7-methoxy-1,2,3,4,5,6,7,7a-octahydro-4a,7-ethano-4,12-methanobenzofuro[3,2-e]isoquinolin-6-yl)ethan-1-one HPLC-purity 92.5% at 215 nm.
NMR and MS data were in agreement with those obtained with Example 16.

Example 18. Preparation of Compound HO-IIIA-MCP (Step D)

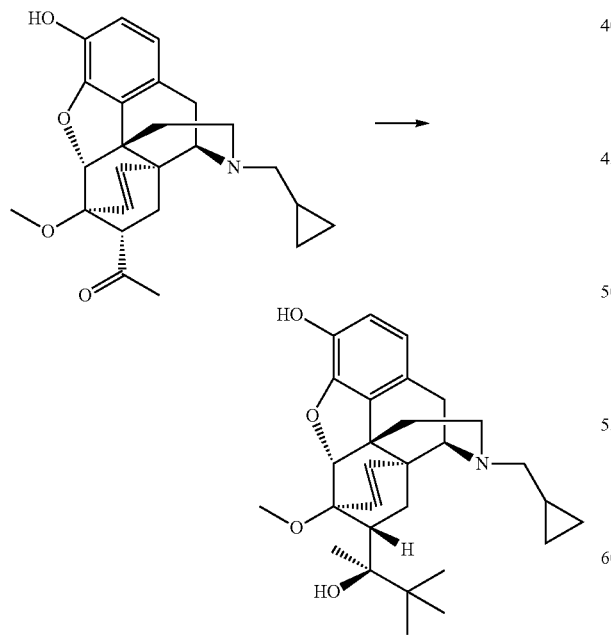

Compound HO-II-MCP (750 mg, 1.84 mmol) dissolved in dioxane (8 mL) was added to a 2.0 M solution of tert-butylmagnesium chloride in ether (11 mL, 22 mmol) and TMEDA (3.31 mL, 22 mmol) dropwise, over 10 min, at room temperature and under a nitrogen atmosphere. Once the addition was complete the mixture was stirred at 60° C. for 4 h under a nitrogen atmosphere. The mixture was then cooled to 0° C. with an ice/water bath and carefully quenched with a saturated aqueous ammonium chloride solution over 15 min. Ethyl acetate (15 mL) was added. After separation the aqueous phase was extracted with ethyl acetate (2×15 mL). The combined organic layers were dried over sodium sulfate, filtered off and the solvents were removed under vacuum. Purification by flash chromatography (0 to 100% ethyl acetate in heptane) yielded Compound HO-IIIA-MCP (200 mg, 23%) as a white solid.

(4R,4aR,7R,7aR,12bS)-3-(cyclopropylmethyl)-14-((S)-2-hydroxy-3,3-dimethylbutan-2-yl)-7-methoxy-1,2,3,4,7,7a-hexahydro-4a,7-ethano-4,12-methanobenzofuro[3,2-e]isoquinolin-9-ol HPLC-purity 99.4% at 215 nm.
MS (ES-API pos) m/z 466.2 (M+1).
$^1$H NMR (300 MHz, CDCl3) δ [ppm] 6.59 (d, 1H), 6.44 (d, 1H), 5.96 (d, 1H), 5.71 (s, 1H), 5.44 (d, 1H), 4.58 (s, 1H), 3.74 (s, 3H), 3.49 (d, 1H), 3.08 (d, 1H), 2.96 (dd, 1H), 2.66 (dd, 1H), 2.48-2.26 (m, 4H), 2.2-2.09 (t, 1H), 1.98-1.78 (m, 2H), 0.99 (s, 12H), 0.91-0.86 (m, 1H), 0.6-0.53 (m, 2H), 0.2-0.09 (m, 2H).
$^{13}$C NMR (75 MHz, CDCl$_3$) δ [ppm] 146.6, 137.3, 135.6, 134.4, 127.8, 124.4, 119.7, 116.1, 99.3, 84.5, 78.7, 59.5, 56.7, 55.2, 47.4, 45.7, 44.1, 43.1, 39.6, 33.8, 32.1, 26.6, 23.1, 19.6, 9.4, 4.3, 3.1.

Example 19. Preparation of Buprenorphine (Step D)

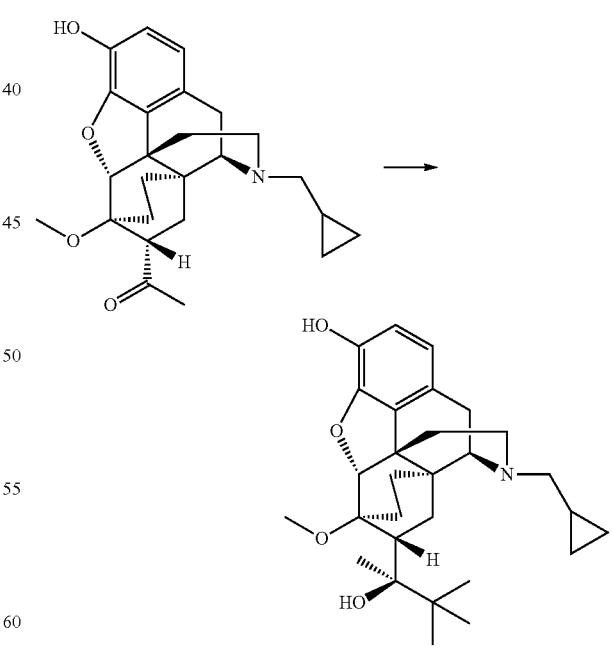

To a stirred solution of Compound HO-IIIB-MCP (130 mg, 0.317 mmol) in a mixture of ether (11 mL) and toluene (5 mL), cooled to 0° C. with an ice/water bath and under a nitrogen atmosphere, was added a 2.0 M solution of tert-butylmagnesium chloride in ether (3.08 mL, 6.153 mmol)

containing TMEDA (0.92 mL, 6.153 mmol) dropwise. After completion of the addition, the mixture was allowed to warm up to room temperature and was stirred for 1.5 h. The mixture was then poured into a mixture of ice/water (25 mL) and a saturated aqueous solution of ammonium chloride (25 mL). The aqueous phase was extracted with ethyl acetate (3×50 mL). The combined organic phases were dried over sodium sulfate, filtered off and the solvent was removed under vacuum. Purification by flash chromatography (0 to 100% ethyl acetate in heptane) yielded buprenorphine (99 mg, 41%) as a white solid.

Buprenorphine

HPLC-purity 98.9% at 215 nm.
MS (ES-API pos) m/z 468.3 (M+H).
$^1$H NMR (300 MHz, CDCl$_3$) δ [ppm] 6.67 (d, J=8.0 Hz, 1H), 6.49 (d, J=8.0 Hz, 1H), 6.02 (s, 1H), 5.78 (br, 1H), 4.43 (d, J=1.2 Hz, 1H), 3.51 (s, 3H), 3.01-2.82 (m, 3H), 2.6 (dd, J=11.9, 5.1 Hz, 1H), 2.38-2.21 (m, 3H), 2.20-2.10 (m, 2H), 1.97 (dt, J=12.6, 5.6 Hz, 1H), 1.9-1.7 (m, 2H), 1.65 (dd, J=12.8, 2.5 Hz, 1H), 1.36 (s, 3H), 1.29 (m, 1H), 1.12-0.96 (m, 10H), 0.9-0.63 (m, 2H), 0.56-0.4 (m, 2H), 0.2-0.07 (m, 2H).
$^{13}$C NMR (75 MHz, CDCl$_3$) δ [ppm] 145.5, 137.4, 132.5, 128.1, 119.5, 116.5, 96.8, 80.8, 79.7, 59.5, 58.3, 52.5, 46.4, 43.7, 43.5, 40.3, 35.9, 35.6, 33.4, 29.6, 26.4, 22.8, 20.1, 18.2, 9.4, 4.1, 3.2.

Example 20. Preparation of Buprenorphine (Step D)

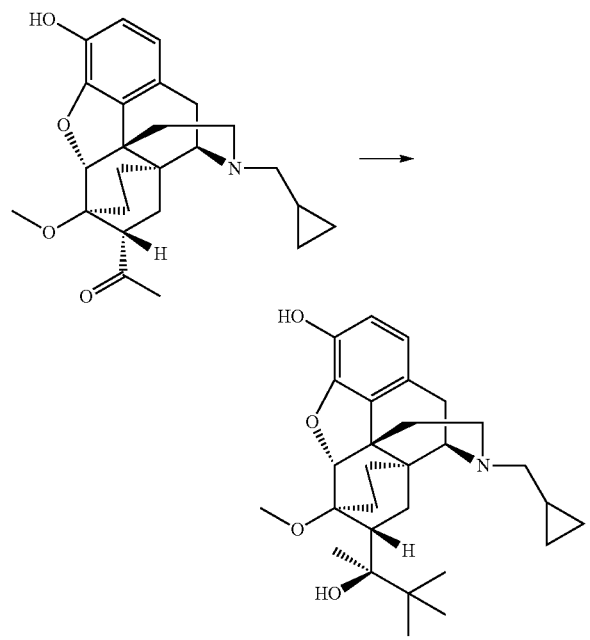 [SMILES: CO[C@]12CC[C@@]3(C[C@@H]1C(C)=O)[C@H]1Cc4ccc(O)c5c4[C@@]3(CCN1CC1CC1)[C@H]2O5 ; CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

To a stirred solution of Compound HO-IIIB-MCP (130 mg, 0.317 mmol) in a mixture of ether and toluene (3:2, 10 mL), cooled to 0° C. with an ice/water bath and under a nitrogen atmosphere, was added a 2.0 M solution of tert-butylmagnesium chloride in ether (2 mL, 4 mmol) dropwise. A white precipitate was obtained. The reaction mixture was allowed to warm to room temperature and the mixture was agitated for 15 h at room temperature. Water (10 mL) was carefully added to the reaction mixture, previously cooled to 0° C. with an ice/water bath, followed by the addition of a saturated aqueous solution of ammonium chloride (10 mL). The aqueous phase was extracted with ethyl acetate (3×50 mL). The combined organic phases were dried over sodium sulfate, filtered off and the solvent was removed under vacuum. Purification by flash chromatography (0 to 100% ethyl acetate in heptane) yielded buprenorphine (47 mg, 32%) as a white solid.

Buprenorphine

HPLC-purity 99.0% at 215 nm.

NMR and MS data were in agreement with those obtained from Example 19.

Example 21. Preparation of Buprenorphine (Step C)

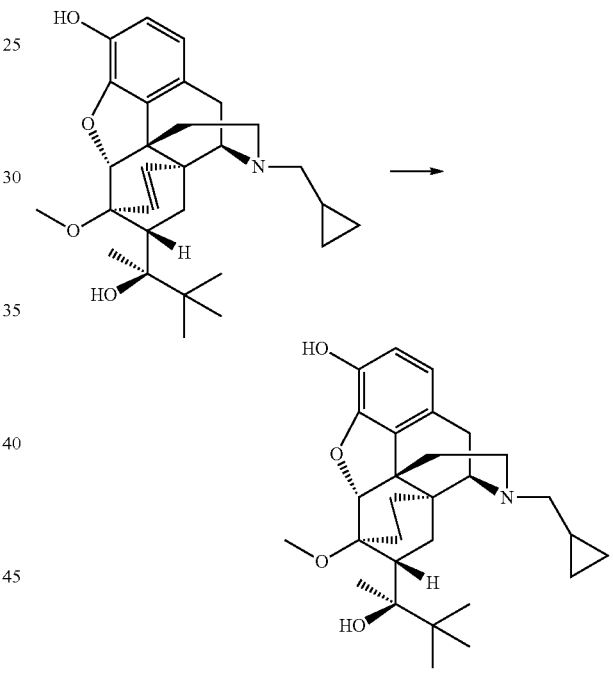

To a suspension of Compound HO-IIIA-MCP (250 mg, 0.537 mmol) in a mixture of isopropanol (4.6 mL) and water (0.4 mL) was added Pd/C (25 mg, 10% w/w) at room temperature. The mixture was then hydrogenated under 1 atmosphere of hydrogen at 80° C. overnight. The mixture was filtered through a plug of Celite and Celite was rinsed with CHCl$_3$. The mother liquor was concentrated under vacuum. Purification by flash chromatography (0 to 80% ethyl acetate in heptane) yielded intermediate buprenorphine (200 mg, 80%) was obtained as a white solid.

Buprenorphine

HPLC-purity 99.1% at 215 nm.

NMR and MS data were in agreement with those obtained for buprenorphine with method A and B previously reported.

Preparation of Buprenorphine from Nororipavine
(Benzyl-Protected Route)

Example 22. Preparation of Compound
BnO-I-MCP (Step F)

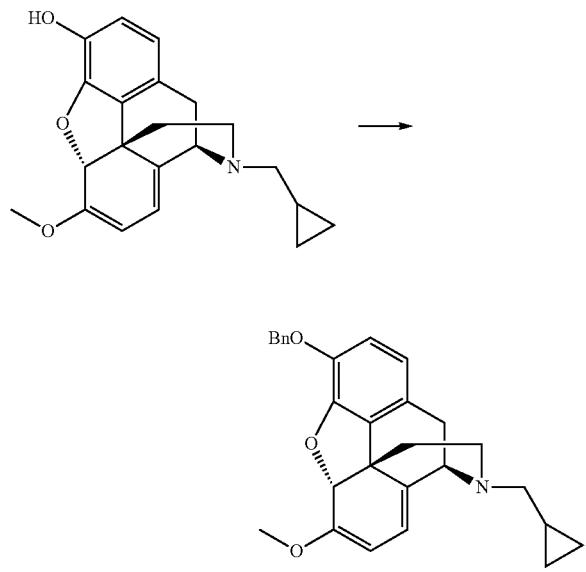

To a solution of intermediate Compound HO-I-MCP (200 mg, 0.59 mmol) in DMF (5 mL) was added sodium hydride (36 mg, 0.89 mmol) at 0° C. and under a nitrogen atmosphere. The mixture was then stirred at 45° C. for 20 min and was cooled to 0° C. Benzyl bromide (130 mg, 0.741 mmol) was added and the mixture was stirred overnight at room temperature. The mixture was cooled to 0° C. with an ice/water bath and water (25 mL) was carefully added. The aqueous mixture was extracted with $CHCl_3$ (3×25 mL). The combined organic layers were washed with water (25 mL), brine (50 mL), dried over sodium sulfate, filtered off and the solvents were removed under vacuum. Purification by flash chromatography (0 to 5% MeOH in DCM) yielded Compound BnO-I-MCP (190 mg, 68%) as an orange/brownish oil.

(4R,7aR,12bS)-9-(Benzyloxy)-3-(cyclopropylmethyl)-7-methoxy-2,3,4,7a-tetrahydro-1H-4,12-methanobenzofuro[3,2-e]isoquinoline HPLC-purity 96.8% at 215 nm.

MS (ES-API pos) m/z 428.2 (M+H).

$^1$H NMR (300 MHz, $CDCl_3$) δ [ppm] 7.95 (br, 1H from DMF), 7.4 (d, 2H), 7.35-7.2 (m, 3H), 6.65 (d, 1H), 6.5 (d, 1H), 5.54 (d, 1H), 5.27 (s, 1H), 5.13 (dd, 2H), 5.02 (d, 1H), 3.94 (d, 1H), 3.55 (s, 3H), 3.26 (d, 1H), 2.95-2.77 (m, 2H+DMF), 2.7 (dd, 1H), 2.5 (d, 2H), 2.18 (dt, 1H), 1.7 (d, 1H), 1.00-0.8 (m, 1H), 0.6-0.47 (m, 2H), 0.2-0.1 (m, 2H).

$^{13}$C NMR (75 MHz, $CDCl_3$) δ [ppm] 152.6, 145.1, 141.6, 137.5, 133.7, 131.7, 128.3, 128.0, 127.7, 127.6, 119.3, 115.8, 112.4, 95.9, 89.0, 71.6, 58.8, 58.6, 54.9, 46.3, 44.1, 36.4, 36.3, 30.8, 9.2, 4.0, 3.8.

Example 23. Preparation of Compound
BnO-I-MCP (Step A3)

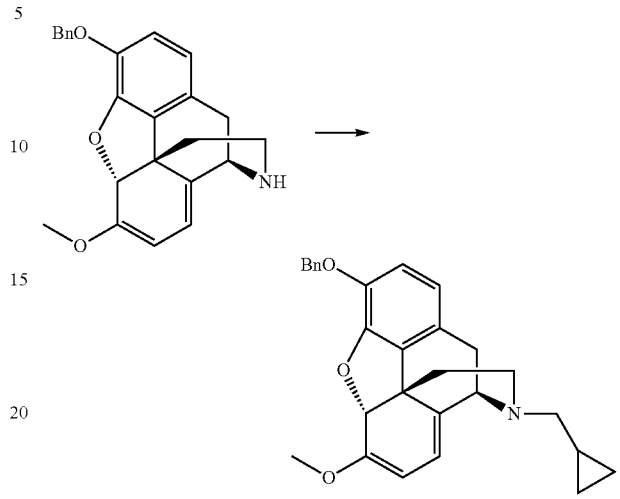

To a solution of Compound BnO-I-H (99 mg, 0.24 mmol), cyclopropane carboxaldehyde (35 mg, 0.48 mmol) and triethylamine (150 mg, 1.21 mmol) in acetonitrile (2.5 mL), at room temperature and under a nitrogen atmosphere, was added formic acid (0.18 mL) dropwise. After stirring the mixture at room temperature for 15 min, di-μ-chlorobis[(p-cymene)chlororuthenium(II)] (0.5 mg, 0.0005 mmol) was added. The mixture was stirred at 50° C. for 15 h. The volatiles were removed under vacuum and water (5 mL) was added to the resulting oil. A 25% ammonium hydroxide aqueous solution (1 mL) was added and the aqueous mixture was extracted with $CHCl_3$ (3×10 mL). The combined organic layers were dried over sodium sulfate, filtered off and concentrated under vacuum. Toluene (10 mL) was added and the solution was concentrated under vacuum to remove the remaining triethylamine. This operation was repeated once more. After concentration to dryness, isolated compound Compound BnO-I-MCP (97 mg, 94%) was obtained as a brown oil.

(4R,7aR,12bS)-9-(Benzyloxy)-3-(cyclopropylmethyl)-7-methoxy-2,3,4,7a-tetrahydro-1H-4,12-methanobenzofuro[3,2-e]isoquinoline HPLC-purity 96.4% at 215 nm.
NMR and MS data were in agreement with those obtained for Example 22.

Example 24. Preparation of Compound
BnO-II-MCP (Step F)

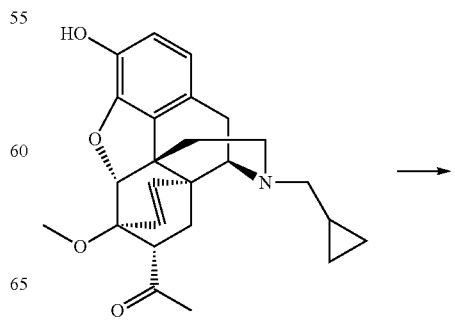

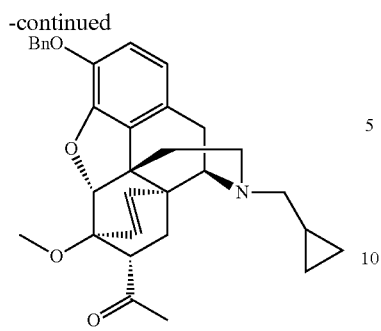

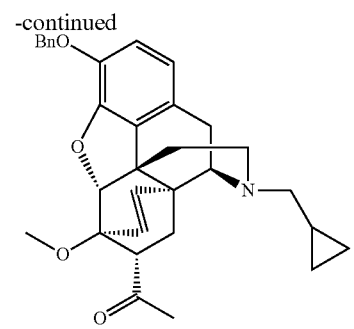

To a suspension of Compound BnO-I-MCP (240 mg, 0.59 mmol) in CHCl$_3$ (3 mL) were added benzyl bromide (0.093 mL, 0.78 mmol) and potassium carbonate (450 mg, 3.26 mmol) at room temperature under a nitrogen atmosphere. The reaction mixture was then refluxed for 15 h. The mixture was cooled down to room temperature and filtered off. The solid was washed with DCM and the filtrate was concentrated under vacuum. Purification by flash chromatography (0 to 50% ethyl acetate in heptane) yielded Compound BnO-II-MCP (270 mg, 92%) as a colorless oil.

1-((4R,4aR,7R,7aR,12bS)-9-(Benzyloxy)-3-(cyclopropylmethyl)-7-methoxy-1,2,3,4,7,7a-hexahydro-4a,7-ethano-4,12-methanobenzofuro[3,2-e]isoquinolin-14-yl)ethan-1-one HPLC-purity 96.4% at 215 nm.

MS (ES-API pos) m/z 498.4 (M+H).

$^1$H NMR (300 MHz, CDCl$_3$) δ [ppm] 7.45-7.23 (m, 5H), 6.65 (d, 1H), 6.47 (d, 1H), 5.91 (d, 1H), 5.59 (d, 1H), 5.19-5.05 (dd, 2H), 4.59 (s, 1H), 3.61 (s, 3H), 3.55 (d, 1H), 3.15-2.86 (m, 3H), 2.75-2.65 (dd, 1H), 2.47-2.28 (m, 4H), 2.15 (s, 3H), 2.05-1.91 (dt, 1H), 1.89-1.8 (dd, 1H), 1.71-1.58 (m, 1H), 1.4-1.31 (dd, 1H), 0.91-0.75 (m, 3H), 0.58-0.42 (m, 2H), 0.18-0.08 (m, 2H).

$^{13}$C NMR (75 MHz, CDCl$_3$) δ [ppm] 209.3, 148.8, 140.6, 137.5, 136.5, 134.6, 129.0, 128.3, 127.7, 127.5, 125.5, 119.4, 116.7, 95.8, 81.4, 72.0, 59.8, 57.0, 53.7, 53.7, 50.8, 48.1, 43.9, 43.2, 33.6, 30.6, 29.9, 23.3, 9.4, 4.1, 3.4.

Example 25. Preparation of Compound BnO-II-MCP (Step B)

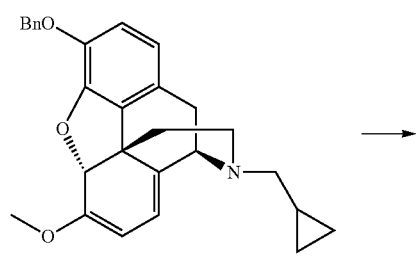

To a solution of Compound BnO-I-MCP (190 mg, 0.415 mmol) in toluene (3 mL) was added methyl vinyl ketone (0.73 mL, 8.35 mmol) at room temperature and under a nitrogen atmosphere. The mixture was stirred at 80° C. for 15 h and the volatiles were removed under vacuum. Purification by flash chromatography (0 to 60% ethyl acetate in heptane) yielded Compound BnO-II-MCP (170 mg, 82%) as a colorless oil.

1-((4R,4aR,7R,7aR,12bS)-9-(Benzyloxy)-3-(cyclopropylmethyl)-7-methoxy-1,2,3,4,7,7a-hexahydro-4a,7-ethano-4,12-methanobenzofuro[3,2-e]isoquinolin-14-yl)ethan-1-one HPLC-purity 92.9% at 215 nm.

NMR and MS data were in agreement with those obtained for Example 24.

Example 26. Preparation of Compound BnO-IIIA-MCP (Step D)

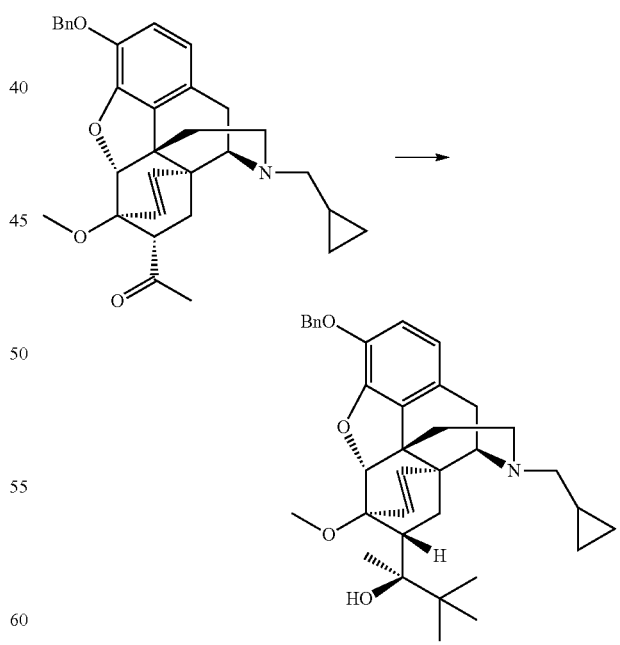

To a solution of Compound BnO-II-MCP (250 mg, 0.5 mmol) in dry toluene (6 mL) at room temperature and under a nitrogen atmosphere, was added a 1.7 M tert-butylmagnesium chloride solution in THF (1.77 mL, 3 mmol) dropwise. The mixture was stirred at room temperature for 18 h prior to further dropwise addition of a 1.7 M tert-butylmagnesium chloride solution in THF (1.77 mL, 3 mmol). The reaction mixture was stirred for 5 h and was poured into a mixture made of ice/water (50 mL) and of an ammonium chloride saturated aqueous solution (50 mL). The mixture was extracted with toluene (3×50 mL). The combined organic layers were washed with brine (50 mL), dried over sodium sulfate, filtered off and the solvents were removed under vacuum. Purification by flash chromatography (0 to 20% ethyl acetate in heptane) yielded Compound BnO-IIIA-MCP (107 mg, 38%) as a colorless oil.

(2 S)-2-((4R,4aR,7R,7aR,12bS)-9-(Benzyloxy)-3-(cyclopropylmethyl)-7-methoxy-1,2,3,4,7,7a-hexahydro-4a, 7-ethano-4, 12-methanobenzofuro[3,2-e]isoquinolin-14-yl)-3,3-di methyl butan-2-ol HPLC-purity 97.2% at 215 nm.
MS (ES-API pos) m/z 556.4 (M+H).
$^1$H NMR (300 MHz, CDCl$_3$) δ [ppm] 7.43-7.3 (m, 5H), 6.65 (d, 1H), 6.46 (d, 1H), 6.00 (d, 1H), 5.65 (s, 1H), 5.43 (d, 1H), 5.19-5.04 (dd, 2H), 4.58 (s, 1H), 3.79 (s, 3H), 3.5 (d, 1H), 3.1 (d, 1H), 2.9 (dd, 1H), 2.69 (dd, 1H), 2.47-2.3 (m, 4H), 2.21-2.12 (t, 1H), 2.01-1.82 (m, 2H), 1.55 (s, 3H), 1.01 (s, 9H), 0.99-0.8 (m, 2H), 0.62-0.43 (m, 2H), 0.22-0.12 (m, 2H).
$^{13}$C NMR (75 MHz, CDCl$_3$) δ [ppm] 148.9, 140.6, 137.8, 137.6, 135.6, 135.1, 129.2, 129.0, 128.4, 128.2, 127.7, 127.5, 125.3, 124.7, 119.4, 116.7, 99.0, 84.5, 78.4, 72.1, 67.9, 59.5, 56.7, 55.2, 47.1, 45.9, 44.1, 43.1, 39.7, 34.0, 32.2, 26.7, 25.6, 23.2, 19.6, 9.5, 4.3, 3.2.

Example 27. Preparation of Buprenorphine (Step C)

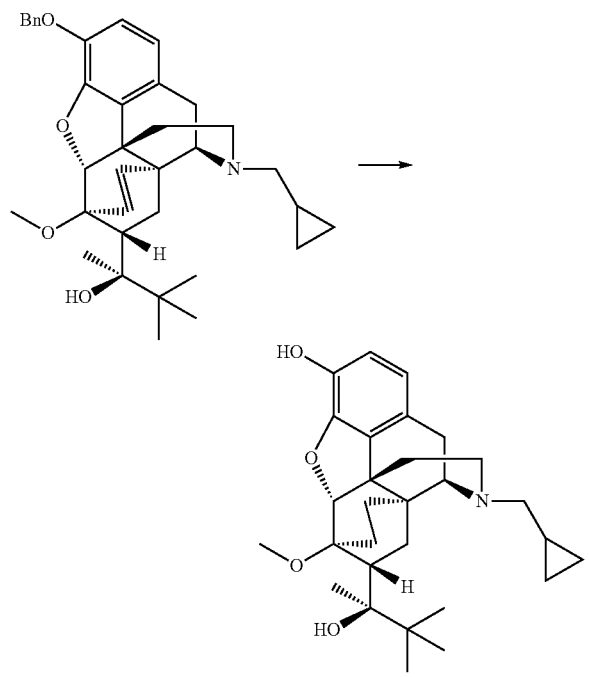 [SMILES: CO[C@]12C=C[C@@]3(C[C@@H]1[C@](C)(O)C(C)(C)C)[C@H]1Cc4ccc(O)c5c4[C@@]3(CCN1CC1CC1)[C@H]2O5 ; CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

To a solution of Compound BnO-IIIA-MCP (194 mg, 0.349 mmol) in a mixture of isopropanol (4.6 mL) and water (0.4 mL) was added Pd/C (20 mg, 10% w/w) at room temperature and under a nitrogen atmosphere. The mixture was then hydrogenated under 1 atmosphere of hydrogen at 80° C. for 15 min. The mixture was filtered through Celite with isopropanol and CHCl$_3$ used as eluents. The solvents were removed under vacuum. Purification by flash chromatography (0 to 60% ethyl acetate in heptane) yielded buprenorphine (115 mg, 70%) as a white solid.

Buprenorphine

HPLC-purity 96.3% at 215 nm.
NMR and MS data were in agreement with those obtained for Examples 10-11 and 19-21.

Example 28. Preparation of Buprenorphine-HCl from Buprenorphine

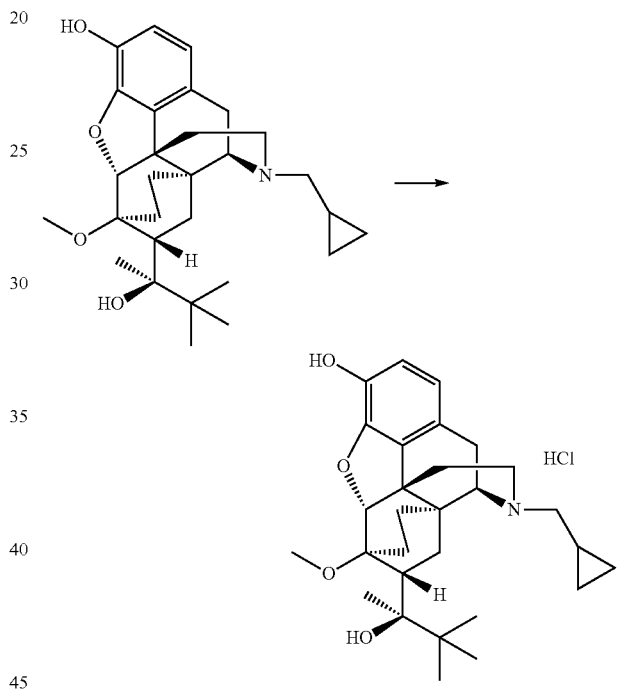

Buprenorphine (100 mg, 0.21 mmol) was taken in EtOH (2 mL) and the mixture was heated until all solid had dissolved. To the warm solution was added 0.5 mL of a mixture of 95 mL EtOH and 5 mL 37% hydrochloric acid (approx. 0.3 mmol). The solution was cooled in the fridge overnight during which time crystals were formed. The crystals were collected and dried under vacuum at 50° C. to yield buprenorphine hydrochloride (102 mg, 96%).

Buprenorphine-HCl

HPLC-purity 99.4% at 215 nm.
DSC-Melting point 267.84-275.26° C.
MS (ES-API pos) m/z 468.2 (M free base+H).
$^1$H NMR (300 MHz, CDCl$_3$/CD$_3$OD) δ [ppm] 6.68 (d, J=8.2 Hz, 1H), 6.50 (d, J=8.2 Hz, 1H), 4.44 (s, 1H), 3.82 (d, J=6.5 Hz, 1H), 3.47 (s, 3H), 3.18-3.35 (m, 4H), 3.0 (d, J=9.5 Hz, 1H), 2.70-2.88 (m, 3H), 2.40 (dt, J=5 and 14 Hz, 1H), 2.22 (t, J=8.8 Hz, 1H), 1.63-1.90 (m, 3H), 1.50 (dd, J=8 and 14 Hz, 1H), 1.29 (s, 3H), 1.20-1.25 (m, 1H), 1.03-1.18 (m, 1H), 1.00 (s, 9H), 0.60-0.85 (m, 4H), 0.38 (m, 1H).

Example 29. Preparation of Compound BnO-I-Me
(Step F)

Example 30. Preparation of Compound BnO-I-H
(Step E)

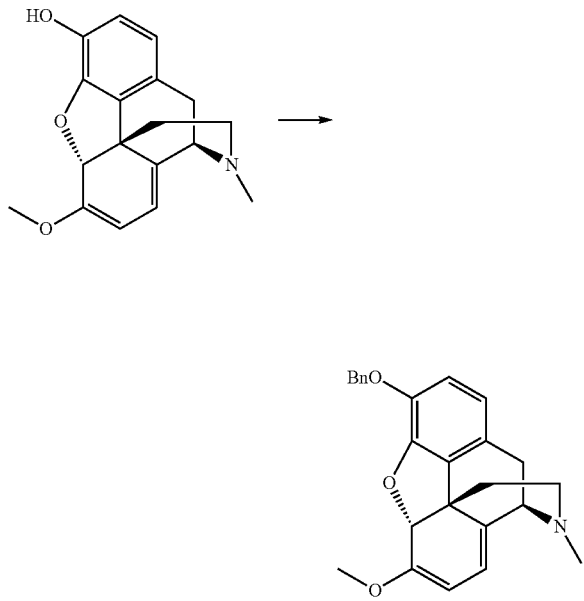

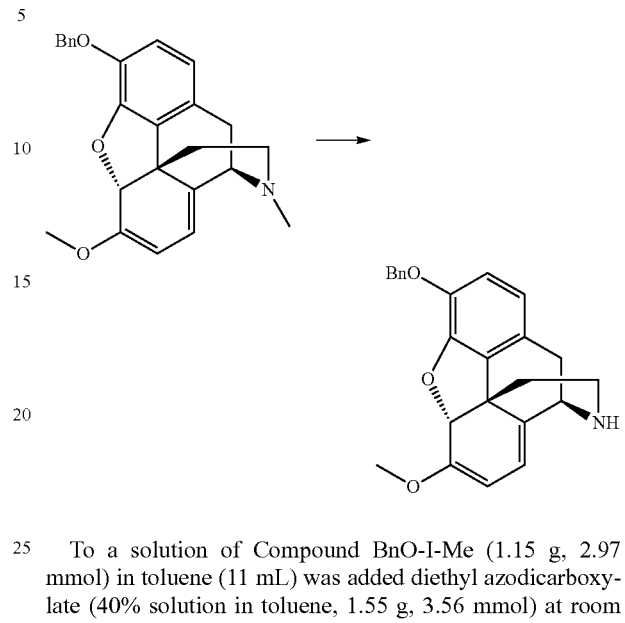

To a solution of Compound HO-I-Me (2.52 g, 8.47 mmol) in DMF (40 mL), previously cooled to 0° C. with an ice/water bath and under a nitrogen atmosphere, was added sodium hydride (440 mg, 11.02 mmol) portion wise. The mixture was allowed to warm up to room temperature and was left stirring for 1 h. The mixture was then cooled to 0° C. with an ice/water bath and benzyl bromide (1.45 g, 8.47 mmol) dissolved in DMF (2 mL) was added dropwise. The mixture was then allowed to warm up slowly to room temperature and was left stirring for 2 h. The mixture was cooled with an ice/water bath to 0° C. and water (200 mL) was added. The mixture was left stirring at room temperature for 30 min and the formed precipitate was filtered off and washed with water. The solid was then dissolved in CHCl$_3$ and washed with brine (50 mL). The organic phase was dried over sodium sulfate$_4$, filtered off and the solvents were removed under vacuum. Purification by flash chromatography (0 to 7% MeOH in DCM) yielded Compound BnO-I-Me (1.21 g, 37%) as a brown oily residue.

(4R,7aR,12bS)-9-(benzyloxy)-7-methoxy-3-methyl-2,3,4,7a-tetrahydro-1H-4,12-methanobenzofuro[3,2-e]isoquinoline HPLC-purity 98.3% at 215 nm.
MS (ES-API pos) m/z 388.2 (M+H).
$^1$H NMR (300 MHz, CDCl$_3$) δ [ppm] 7.5-7.41 (d, 2H), 7.38-7.2 (m, 3H), 6.67 (d, 1H), 6.53 (d, 1H), 5.55 (d, 1H), 5.31 (s, 1H), 5.25-5.1 (q, 2H), 5.04 (d, 1H), 3.62 (s, 3H), 3.35-3.23 (d, 1H), 2.87-2.74 (dt, 1H), 2.72-2.55 (m, 2H), 2.45 (s, 3H), 2.29-2.13 (m, 1H), 1.79-1.7 (dd, 1H)
$^{13}$C NMR (75 MHz, CDCl$_3$) δ [ppm] 152.5, 145.3, 141.6, 137.6, 133.7, 132.4, 128.3, 128.3, 127.7, 127.6, 119.3, 115.9, 111.5, 95.9, 89.1, 71.6, 60.8, 54.9, 46.0, 45.9, 42.4, 37.0, 29.5.

To a solution of Compound BnO-I-Me (1.15 g, 2.97 mmol) in toluene (11 mL) was added diethyl azodicarboxylate (40% solution in toluene, 1.55 g, 3.56 mmol) at room temperature and under a nitrogen atmosphere. The mixture was stirred at 50° C. for 15 h. The solvent was removed under vacuum and the residue was dissolved in a mixture of EtOH (6 mL) and water (3 mL). Pyridine hydrochloride (525 mg, 4.45 mmol) was added and the mixture was refluxed for 2 h. The solvents were removed under vacuum. Purification by flash chromatography (0 to 20% MeOH in DCM) yielded Compound BnO-I-H (590 mg, 48%) as a yellow solid.

(4I,7aI,12bI)-9-(benzyloxy)-7-methoxy-2,3,4,7a-tetrahydro-1H-4,12-methanobenzofuro[3,2-e]isoquinoline hydrochloride HPLC-purity 93.5% at 284 nm.
MS (ES-API pos) m/z 374.2 (M+1).
$^1$H NMR (300 MHz, CDCl$_3$) δ [ppm] 7.42-7.37 (d, 2H), 7.36-7.21 (m, 3H), 6.7 (d, 1H), 6.58 (d, 1H), 5.85 (d, 1H), 5.32 (s, 1H), 5.21-5.07 (q, 2H), 5.01 (d, 1H), 4.62 (d, 1H), 3.63-3.53 (m, 4H), 3.51-3.38 (m, 2H), 3.37-3.21 (m, 1H), 3.20-3.08 (dd, 1H), 2.55-2.39 (m, 1H), 1.96-1.87 (d, 1H).
$^{13}$C NMR (75 MHz, CDCl$_3$) δ [ppm] 154.0, 145.2, 142.2, 137.1, 132.0, 128.4, 127.9, 127.6, 125.0, 124.5, 120.1, 116.9, 116.7, 95.4, 87.9, 71.6, 55.3, 53.2, 50.4, 44.8, 37.1, 34.5, 33.9.

Example 31. Preparation of Compound BnO-I-Bn
(Step F)

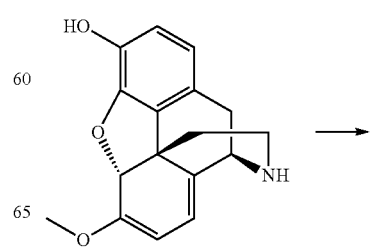

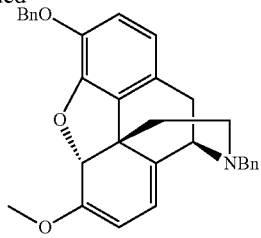

A 500 mL flask was charged with nororipavine (5.66 g, 20 mmol), MeOH (100 mL), and water (50 mL). The suspension was stirred at room temperature and NaOH-pellets (2.50 g, 60 mmol, 3 equiv) were added. After 10 min a light brown solution was obtained and benzyl bromide (8.50 g, 50 mmol, 2.5 equiv) was added over a period of 1 min. A slight exotherm was observed and after 10 min a precipitate was formed. After 2 h the mixture was rotary evaporated to remove most of the MeOH (65 mL). The residue (approximately 100 mL) was cooled in ice-water for 15 min and then filtered. The solid was washed with water (2×10 mL), then with MeOH (10 mL), and dried under vacuum to afford Compound BnO-I-Bn (8.6 g, 93%).

N,O-Dibenzyl-nororipavine

HPLC-purity 95.7% at 254 nm.
MS (ES-API pos) m/z 464.4 (M+H).
$^1$H NMR (300 MHz, CDCl$_3$) δ [ppm] 7.49-7.24 (m, 10H), 6.68 (d, J=8.1 Hz, 1H), 6.54 (d, J=8.2 Hz, 1H), 5.49 (d, J=6.4 Hz, 1H), 5.32 (s, 1H), 5.22 (d, J=12.2 Hz, 1H), 5.15 (d, J=12.1 Hz, 1H), 5.06 (d, J=6.4 Hz, 1H), 3.77 (d, J=2.9 Hz, 2H), 3.63 (s, 4H), 3.33 (d, J=18.0 Hz, 1H), 2.96 (td, J=13.0, 3.5 Hz, 1H), 2.72 (m, 2H), 2.26 (td, J=12.6, 4.9 Hz, 1H), 1.70 (dd, J=12.6, 3.0 Hz, 1H).
$^{13}$C NMR (75 MHz, CDCl$_3$) δ [ppm] 152.6, 145.7, 141.7, 138.7, 137.6, 132.9, 132.5, 129.0, 128.4, 127.7, 127.6, 127.1, 119.3, 115.9, 111.8, 96.0, 89.2, 71.7, 58.3, 58.2, 55.0, 46.6, 44.1, 36.5, 31.7.

Example 32. Preparation of Compound BnO-II-Bn (Step B)

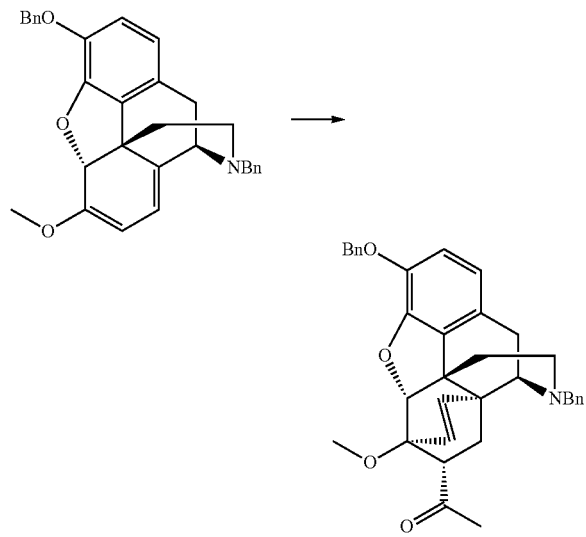

A solution of Compound BnO-I-Bn (4.63 g, 10.0 mmol) and methyl vinyl ketone (8 mL, 100 mmol) in toluene (50 mL) was heated at 80° C. for 16 h. After cooling to room temperature the mixture was concentrated under vacuum to give a brown oily residue (5.5 g), which was purified by column chromatography (120 g SiO$_2$, elution with 0-20% EtOAc in heptane, R$_f$ 0.3) to afford Compound BnO-II-Bn as a colorless solid (4.25 g, 77% yield).

7α-Acetyl-N,O-dibenzyl-6,14-endo(etheno)tetra-hydro-nororipavine

HPLC-purity 97.3% at 215 nm.
MS (ES-API pos) m/z 534.4 (M+H).
$^1$H NMR (300 MHz, CDCl$_3$) δ [ppm] 7.45-7.20 (m, 10H), 6.68 (d, J=8.1 Hz, 1H), 6.51 (d, J=8.2 Hz, 1H), 5.89 (dt, J=8.9, 1.2 Hz, 1H), 5.53 (d, J=8.8 Hz, 1H), 5.13 (d, J=5.4 Hz, 2H), 4.60 (d, J=1.5 Hz, 1H), 3.66 (s, 2H), 3.62 (s, 3H), 3.27 (dd, J=12.5, 6.0 Hz, 2H), 3.09 (dd, J=12.6, 9.4 Hz, 1H), 2.95 (dd, J=9.4, 6.5 Hz, 1H), 2.67-2.38 (m, 3H), 2.16 (s, 3H), 2.00 (td, J=12.5, 5.9 Hz, 1H), 1.87 (ddd, J=13.1, 4.0, 1.8 Hz, 1H), 1.35 (dd, J=12.6, 6.5 Hz, 1H).
$^{13}$C NMR (75 MHz, CDCl$_3$) δ [ppm] 209.35, 148.84, 140.76, 139.09, 137.57, 136.20, 134.56, 128.86, 128.65, 128.38, 127.77, 127.53, 127.10, 125.62, 119.54, 116.84, 95.69, 81.33, 72.08, 59.50, 57.04, 53.70, 50.98, 48.09, 43.81, 43.35, 33.60, 30.56, 29.89, 23.53.

Example 33. Preparation of Compound BnO-IIIA-Bn (Step D)

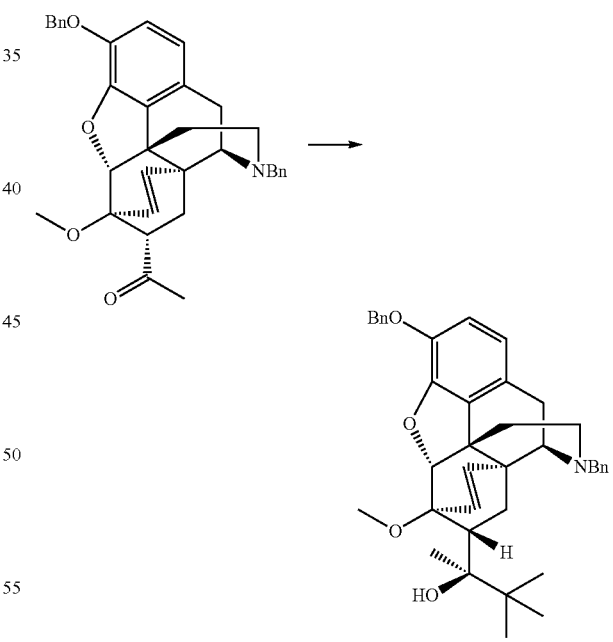

A 50 mL flask was charged with a solution of tert-butylmagnesium chloride (1.7 M solution in THF, 5 mL, 8.5 mmol) and toluene (8 mL). The THF was evaporated in vacuo and to the residual Grignard solution in toluene (approximately 10 mL) was added a solution of Compound BnO-II-Bn (0.70 g, 1.3 mmol) in dry toluene (8 mL). The reaction mixture was heated to 60° C. for 2 h and then cooled in an ice-water bath and quenched by addition of 10% aqueous ammonium chloride (25 mL). The layers were separated and the aqueous layer was extracted with toluene (3×25 mL). The combined organic layers were washed with brine, dried with sodium sulfate, and concentrated to an oil. Purification by column chromatography (120 g SiO$_2$, elution with 0-20% EtOAc in heptane, Rf 0.6) afforded Compound BnO-III-Bn as white solid (0.38 g, 50%).

N,O-Dibenzyl-7α-(2-(S)-hydroxy-3,3-dimethyl-2-butyl)-6,14-endo(etheno)tetrahydro-nororipavine (3)

HPLC-purity 95.6% at 215 nm.
MS (ES-API pos) m/z 492.4 (M+H).
$^1$H NMR (300 MHz, CDCl$_3$) δ [ppm] 7.43-7.30 (m, 10H), 6.66 (d, J=8.1 Hz, 1H), 6.48 (d, J=8.2 Hz, 1H), 5.95 (d, J=8.9 Hz, 1H), 5.60 (s, 1H), 5.34 (d, J=8.9 Hz, 1H), 5.14 (d, J=12.0 Hz, 1H), 5.07 (d, J=12.0 Hz, 1H), 4.58 (d, J=1.4 Hz, 1H), 3.76 (s, 3H), 3.68 (d, J=2.7 Hz, 2H), 3.22 (d, J=12 Hz, 1H), 3.17-3.01 (m, 2H), 2.70-2.52 (m, 2H), 2.39 (dd, J=18.5, 6.6 Hz, 1H), 2.17 (t, J=8.6 Hz, 1H), 1.99 (td, J=12.1, 11.3, 6.1 Hz, 1H), 1.89 (d, J=12.6 Hz, 1H), 1.04 (s, 9H), 0.98 (s, 3H), 1.01-0.82 (m, 1H).
$^{13}$C NMR (75 MHz, CDCl$_3$) δ [ppm] 148.89, 140.64, 139.37, 137.56, 135.31, 135.00, 128.93, 128.61, 128.38, 128.32, 127.78, 127.46, 127.06, 124.71, 119.44, 116.71, 98.94, 84.46, 78.34, 72.11, 59.10, 56.04, 55.21, 47.00, 45.92, 44.28, 43.14, 39.70, 34.08, 32.22, 26.64, 23.39, 19.57.

Example 34. Preparation of Compound HO-IV-H (Step C)

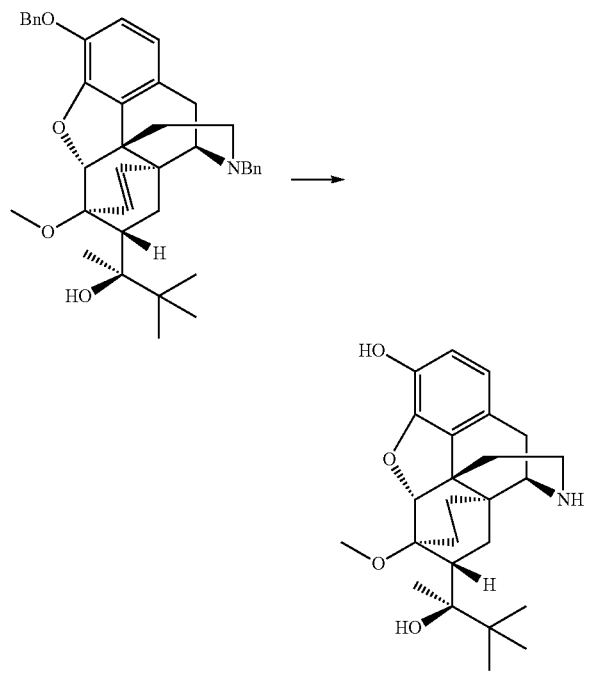

A vigorously stirred mixture of Compound BnO-III-Bn (355 mg, 0.6 mmol), and Pd/C (10%, 30 mg) in iPrOH (10 mL), water (0.2 mL), and acetic acid (0.1 mL) was hydrogenated at 60° C. for 16 h under 1 atmosphere of hydrogen. IPC NMR showed that both benzyl groups were removed and the double bond was only partly reduced. The catalyst was refreshed and hydrogenation was continued at 80° C. for 60 h. ICP NMR showed no more double bond signals. The mixture was filtered over Celite. The filter was flushed with iPrOH and DCM. The filtrate was concentrated to give Compound HO-IV-H as acetate salt (300 mg, 100%).

Norbuprenorphine

HPLC-purity 89% at 215 nm.
MS (ES-API pos) m/z 414.3 (M+H).
$^1$H NMR (300 MHz, CDCl$_3$) δ [ppm] 7.64 (br s, 2H), 6.76 (d, J=8.0 Hz, 1H), 6.49 (d, J=8.1 Hz, 1H), 5.80 (br s, 1H), 4.40 (s, 1H), 3.59 (d, J=6.4 Hz, 1H), 3.51 (s, 3H), 3.35-3.25 (m, 2H), 3.04 (t, J=13.5 Hz, 1H), 2.88 (dd, J=19.2, 6.4 Hz, 1H), 2.75 (t, J=13.5 Hz, 1H), 2.22-2.07 (m, 2H), 2.01 (s, 3H), 1.90-1.70 (m, 3H), 1.52 (dd, J=13.1, 9.0 Hz, 1H), 1.33 (s, 3H), 1.18 (m, 1H), 1.03 (s, 9H), 0.76 (t, J=12.3 Hz, 1H).
$^{13}$C NMR (75 MHz, CDCl$_3$) δ [ppm] 145.91, 139.04, 129.99, 123.75, 120.29, 118.23, 95.53, 79.85, 79.62, 53.66, 52.69, 45.00, 42.97, 40.34, 34.40, 32.1, 31.8, 29.9, 29.1, 26.23, 22.9, 20.13, 17.8.

Example 35. Preparation of Buprenorphine (Step A1)

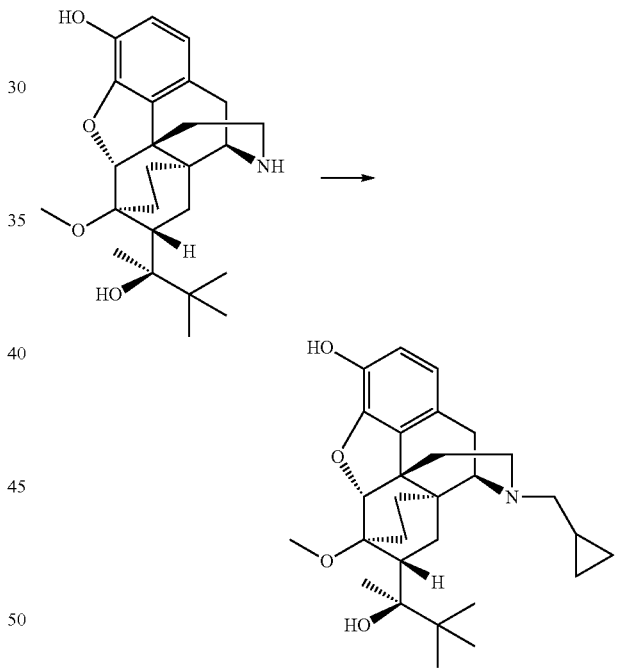

A 50 mL flask was charged with Compound HO-I-H (210 mg, 0.44 mmol), cyclopropane carboxaldehyde (80 μL, 1 mmol), dichloro(p-cymene)ruthenium(II) dimer (10 mg, 0.016 mmol), triethylamine (0.42 mL, 3.1 mmol), and acetonitrile (5 mL). The mixture was stirred under nitrogen at room temperature and formic acid (0.24 mL, 6.2 mmol) was added dropwise. The resulting mixture was heated at 60° C. for 1 h. The mixture was cooled to room temperature and concentrated under vacuum. The residue was partitioned between toluene and 1 N aqueous NaOH. The aqueous layer was extracted twice with toluene. The combined organic layers were washed with brine, dried on sodium sulfate, and concentrated under vacuum to afford buprenorphine (160 mg, 78%).

101

Buprenorphine

HPLC-purity 85.6% at 215 nm.
MS and NMR data were in agreement with those obtained in previous examples.

Example 36. Preparation of Compound HO-I-Ac (Step G)

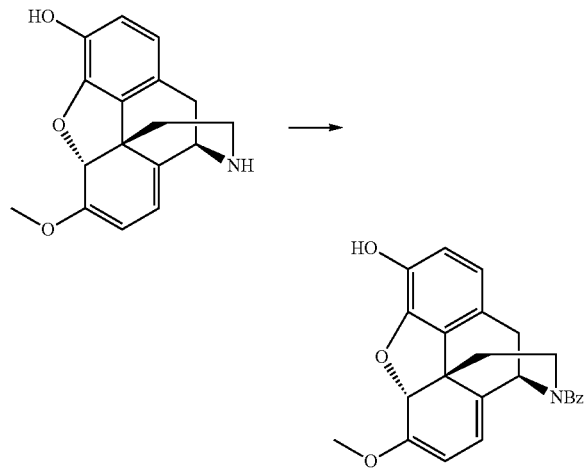

Under a nitrogen atmosphere benzoyl chloride (0.45 mL, 3.88 mmol) was added slowly to a stirred mixture of nororipavine (1.00 g, 3.53 mmol) and triethylamine (0.59 mL) in dichloromethane (10 mL). The resulting mixture was stirred for 50 minutes at room temperature. Dichloromethane (20 mL) was added. The mixture was extracted with water (2×10 mL). The organic layer was dried over $Na_2SO_4$, filtered and concentrated under reduced pressure. The residue was purified by column chromatography (4 g of silica, 0-60% EtOAc in heptanes) to afford Compound HO-I-Ac (0.82 g, 60%).

((12bS)-9-hydroxy-7-methoxy-1,2,4,7a-tetrahydro-3H-4,12-methanobenzofuro[3,2-e]isoquinolin-3-yl)(phenyl)methanone MS (ES-API pos) m/z 388.3 (M+H).
$^1$H NMR (300 MHz, $CDCl_3$) δ [ppm] 7.44 and 7.40 (2×s, 5H), 6.69 (d, J=8.2 Hz, 1H), 6.59 and 6.54 (2×d, J=8.2 Hz, 1H), 5.76 (m, 1H), 5.54 (s, 1H), 5.33 (d, J=7.6 Hz, 1H), 5.11 (d, J=5.9 Hz, 0.5H), 5.02 (d, J=6.5 Hz, 0.5H), 4.69 (m, 1H), 3.70-3.51 (m, 1H), 3.62 (s, 3H), 3.28-2.95 (m, 3H), 2.25-1.60 (m, 2H).

Example 37. Preparation of Compound BnO-I-Ac (Step F)

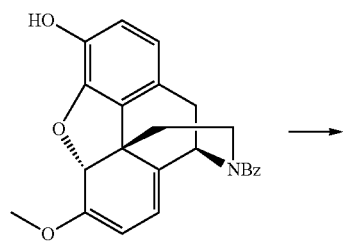

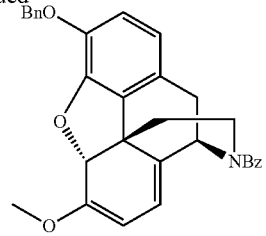

Under a nitrogen atmosphere a mixture of Compound 4 (826 mg, 2.13 mmol), benzyl bromide (0.38 mL, 3.20 mmol) and potassium carbonate (589 mg, 4.26 mmol) in acetone (6 mL) was heated to reflux for 18 h. The solvent was removed under reduced pressure. Water (20 mL) was added and the mixture was extracted with EtOAc (2×20 mL). The combined extracts were dried over $Na_2SO_4$, filtered and concentrated under reduced pressure. The residue was stirred with heptanes. The solvent was decanted and the residue was dried under reduced pressure at 50° C. to afford Compound BnO-I-Ac (1.13 g, quantitative yield).

((12bS)-9-(benzyloxy)-7-methoxy-1,2,4,7a-tetrahydro-3H-4,12-methanobenzofuro[3,2-e]isoquinolin-3-yl)(phenyl)methanone MS (ES-API pos) m/z 478.3 (M+H).
$^1$H NMR (300 MHz, $CDCl_3$) δ [ppm] 8.22-7.28 (m, 10H), 6.71 (d, J=8.2 Hz, 1H), 6.58 and 6.52 (2×d, J=8.2 Hz, 1H), 5.77 (m, 1H), 5.34 (d, J=8.8 Hz, 1H), 5.19 (m, 2H), 5.10 (d, J=5.9 Hz, 0.5H), 5.01 (d, J=6.5 Hz, 0.5H), 4.69 (m, 1H), 3.70-3.46 (m, 1H), 3.64 (s, 3H), 3.31-2.95 (m, 3H), 2.21-1.65 (m, 2H).

Example 38. Preparation of Compound BnO-I-Bn (Step H)

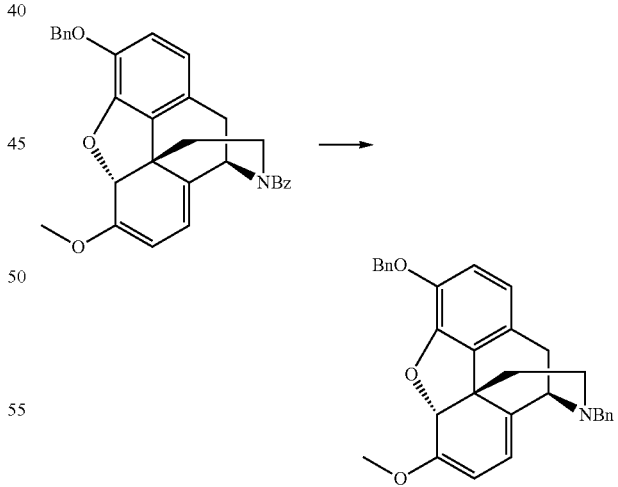

Under a nitrogen atmosphere lithium aluminium hydride (162 mg, 4.26 mmol) was added to a stirred solution of Compound 5 (1.02 g, 2.13 mmol) in THF (15 mL). The mixture was heated at 60° C. for 1.5 h. Water (0.16 mL), 15% aqueous NaOH (0.16 mL) and water (0.48 mL) were added. After stirring for 15 minutes EtOAc was added and the mixture was filtered over a pad of Celite. The filtrate was concentrated under reduced pressure and the residue was purified by column chromatography (25 g of silica, 0-90% EtOAc in heptanes to afford Compound BnO-I-Bn (694 mg, 70%) as an off-white solid.

N,O-Dibenzyl-nororipavine (1) (12bS)-3-benzyl-9-(benzyloxy)-7-methoxy-2,3,4,7a-tetrahydro-1H-4,12-methanobenzofuro[3,2-e]isoquinoline MS (ES-API pos) m/z 464.3 (M+H).
$^1$H NMR (300 MHz, CDCl$_3$) δ [ppm] 7.58-7.16 (m, 10H), 6.68 (d, J=8.1 Hz, 1H), 6.54 (d, J=8.2 Hz, 1H), 5.49 (d, J=6.4 Hz, 1H), 5.32 (s, 1H), 5.26-5.10 (m, 2H), 5.06 (d, J=6.4 Hz, 1H), 3.76 (m, 2H), 3.63 (s, 3H+m, 1H), 3.32 (d, J=17.9 Hz, 1H), 2.95 (td, J=13.0, 3.5 Hz, 1H), 2.76-2.66 (m, 2H), 2.26 (td, J=12.6, 5.0 Hz, 1H), 1.69 (d, J=12.3 Hz, 1H).

MS and NMR data were in agreement with those obtained in previous examples.

Example 39. Preparation of Compound AcO-I-Ac (Step G)

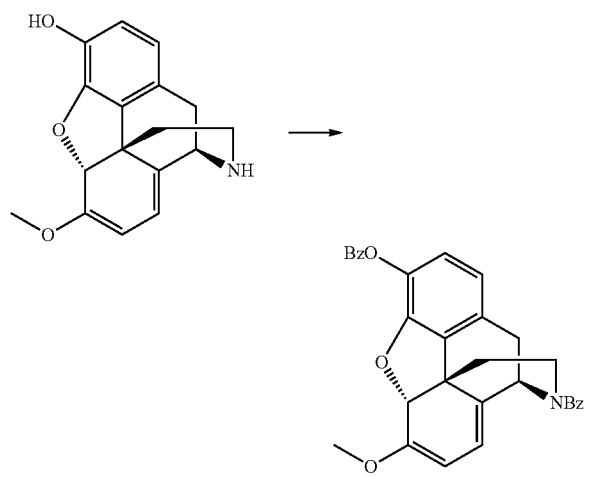

Under a nitrogen atmosphere benzoyl chloride (1.8 mL, 15.5 mmol) was added slowly to a stirred mixture of nor-oripavine (2.00 g, 7.06 mmol) and triethylamine (2.3 mL, 16.9 mmol) in dichloromethane (10 mL), while cooling in an ice-bath. The cooling bath was removed and the mixture was stirred at room temperature for 1.5 h. Dichloromethane (65 mL) was added and the mixture was extracted with water (2×30 mL). The organic layer was dried over Na$_2$SO$_4$, filtered and concentrated under reduced pressure. The residue was purified by column chromatography (40 g of silica, 0-85% EtOAc in heptanes) to afford Compound AcO-I-Ac (2.93 g, 84%).

(12bS)-3-benzoyl-7-methoxy-2,3,4,7a-tetrahydro-1H-4,12-methanobenzofuro[3,2-e]isoquinolin-9-yl benzoate MS (ES-API pos) m/z 492.2 (M+H).
$^1$H NMR (300 MHz, CDCl$_3$) δ [ppm] 8.20 (d, J=7.1 Hz, 2H), 7.62 (m, 1H), 7.51-7.42 (m, 7H), 6.94 (d, J=8.2 Hz, 1H), 6.73 and 6.68 (2×d, J=8.2 Hz, 1H), 5.80 (m, 1H), 5.36 (m, 1H), 5.11 (d, J=5.9 Hz, 0.5H), 5.02 (d, J=5.3 Hz, 0.5H), 4.73 (m, 1H), 3.73-3.49 (m, 1H), 3.61 (s, 3H), 3.37-3.03 (m, 3H), 2.26-1.82 (m, 2H).

Example 40. Preparation of Compound AcO-II-Ac (Step B)

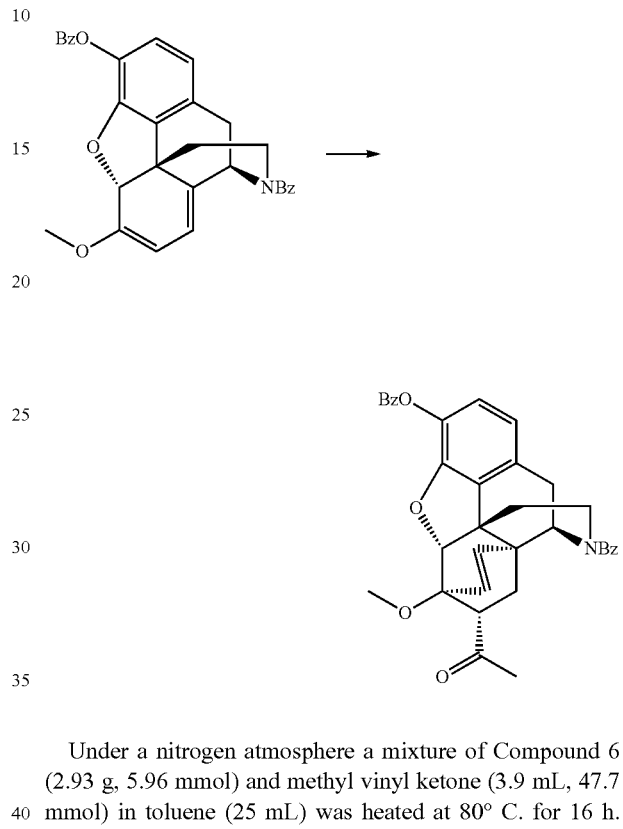

Under a nitrogen atmosphere a mixture of Compound 6 (2.93 g, 5.96 mmol) and methyl vinyl ketone (3.9 mL, 47.7 mmol) in toluene (25 mL) was heated at 80° C. for 16 h. After standing for 2 days at room temperature methyl vinyl ketone (3.9 mL, 47.7 mmol) was added. The mixture was heated at 80° C. for 16 h. The solvent was removed by evaporation under reduced pressure. The residue was purified by column chromatography (120 g of silica, 0-50% EtOAc in heptanes) to afford Compound AcO-II-Ac (2.89 g, 86%).

(4R,4aR,7R,7aR,12bS,14S)-14-acetyl-3-benzoyl-7-methoxy-1,2,3,4,7,7a-hexahydro-7,4a-ethano-4,12-methanobenzofuro[3,2-e]isoquinolin-9-yl benzoate MS (ES-API pos) m/z 562.2 (M+H).
$^1$H NMR (300 MHz, CDCl$_3$) δ [ppm] 8.15 (d, J=7.6 Hz, 2H), 7.62 (m, 1H), 7.52-7.39 (m, 7H), 6.91 (d, J=8.2 Hz, 1H), 6.70 and 6.66 (2×d, J=8.2 Hz, 1H), 6.10 (d, J=8.8 Hz, 0.5H), 5.97 (d, J=8.8 Hz, 0.5H), 5.73 (d, J=8.8 Hz, 0.5H), 5.52 (d, J=6.4 Hz, 0.5H), 5.43 (d, J=8.8 Hz, 0.5H), 4.75 (d, J=10.0 Hz, 0.5H), 4.60 (s, 1H), 4.40 (d, J=4.7 Hz, 0.5H), 3.71 (d, J=14.7 Hz, 0.5H), 3.55-3.26 (m, 1H), 3.50 (s, 3H), 3.20-3.03 (m, 2H), 2.93-2.84 (m, 1H), 2.38 (dd, J=12.9, 9.4 Hz, 1H), 2.18-2.02 (m, 4H), 1.91 (m, 1H), 1.71-1.56 (m, 1H).

Example 41. Preparation of Compound HO-IIIA-Ac (Step D)

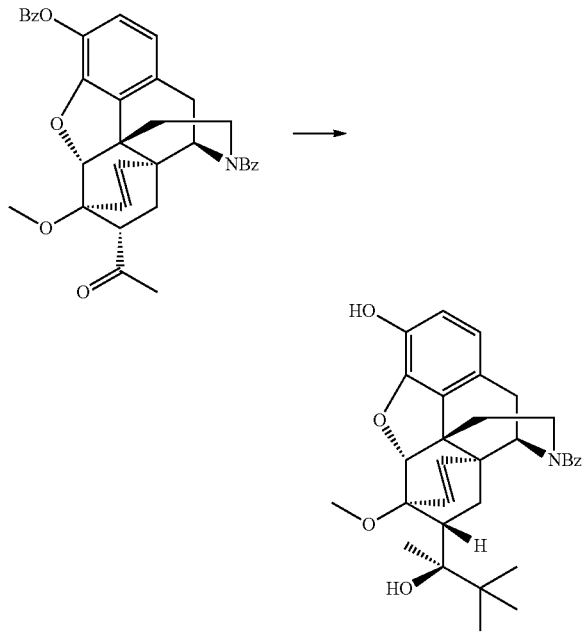

Dry toluene (120 mL) was added to a solution of tert-butylmagnesium chloride (1.7 M in THF, 27 mL). Part of the solvent was evaporated under reduced pressure at 50° C., leaving around 30 mL. Under a nitrogen atmosphere a solution of Compound 7 (1.69 g, 3.01 mmol) in dry toluene (12 mL) was added slowly by means of a syringe. The mixture was stirred at 60° C. for 3 h. After cooling to room temperature diethyl ether (50 mL) and water (75 mL) were added. The mixture was acidified with 1N aqueous HCl. Both layers were separated. The aqueous layer was extracted with EtOAc (2×50 mL). The combined organic layers were dried over Na$_2$SO$_4$, filtered and concentrated under reduced. The residue was purified by column chromatography (40 g of silica, 0-50% EtOAc in heptanes) to afford Compound HO-IIIA-Ac (1.10 g, 71%).

((4R,4aR,7R,7aR,12bS,14R)-9-hydroxy-14-(2-hydroxy-3,3-dimethylbutan-2-yl)-7-methoxy-1,2,7,7a-tetrahydro-7,4a-ethano-4,12-methanobenzofuro[3,2-e]isoquinolin-3(4H)-yl)(phenyl)methanone MS (ES-API pos) m/z 516.3 (M+H).

$^1$H NMR (300 MHz, CDCl$_3$) δ [ppm] 7.44-7.40 (m, 5H), 6.65 (d, J=8.2 Hz, 1H), 6.54 and 6.49 (2×d, J=8.2 Hz, 1H), 6.07 and 5.99 (2×d, J=9.4 Hz, 1H), 5.54-5.42 (m, 2H), 5.23 (d, J=8.8 Hz, 0.5H), 4.90-4.71 (m, 1.5H), 4.60 (d, J=10.6 Hz, 1H), 4.28 (d, J=6.5 Hz, 0.5H), 3.76 and 3.74 (2×s, 3H), 3.70-3.65 (m, 0.5H), 3.44-3.33 (m, 0.5H), 3.26-2.94 (m, 2.5H), 2.39-2.27 (m, 1H), 2.20-2.11 (m, 1H), 2.08-1.88 (m, 1H), 1.88-1.78 (m, 1H), 1.38-1.20 (m, 1H), 1.01 (s, 9H), 0.92 (s, 3H).

Example 42. Preparation of Compound HO-IIIA-Bn (Step h)

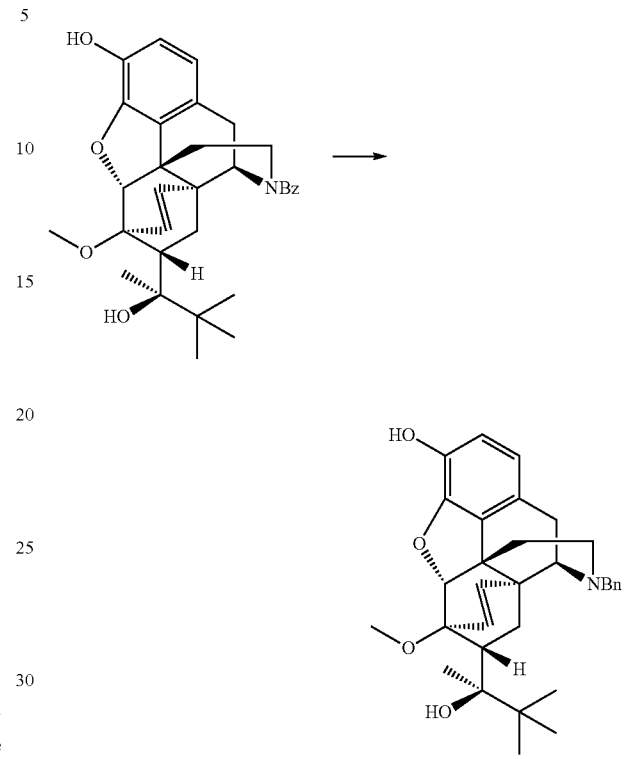

Under a nitrogen atmosphere Compound 8 (1.01 g, 1.96 mmol) was dissolved in THF (25 mL). Lithium aluminum hydride (149 mg, 3.92 mmol) was added and the mixture was heated at 70° C. for 3 h. After standing for 18 h at room temperature water (70 mL) was added and the mixture was extracted with EtOAc (3×70 mL). The combined extracts were dried over Na$_2$SO$_4$, filtered and concentrated under reduced pressure. The residue was purified by column chromatography (24 g of silica, 0-30% EtOAc in heptanes) to afford Compound HO-IIIA-Bn (564 mg, 57%).

(4R,4aR,7R,7aR,12bS,14R)-3-benzyl-14-(2-hydroxy-3,3-dimethylbutan-2-yl)-7-methoxy-1,2,3,4,7,7a-hexahydro-7,4a-ethano-4,12-methanobenzofuro[3,2-e]isoquinolin-9-ol MS (ES-API pos) m/z 502.3 (M+H).

$^1$H NMR (300 MHz, CDCl$_3$) δ [ppm] 7.46-7.21 (m, 5H), 6.62 (d, J=8.0 Hz, 1H), 6.49 (d, J=8.1 Hz, 1H), 5.95 (d, J=8.9 Hz, 1H), 5.67 (s, 1H), 5.35 (d, J=8.9 Hz, 1H), 5.29 (s, 1H), 4.61 (s, 1H), 3.75 (s, 3H), 3.69 (s, 2H), 3.24 (d, J=18.4 Hz, 1H), 3.18-3.03 (m, 2H), 2.74-2.49 (m, 2H), 2.40 (dd, J=18.4, 6.7 Hz, 1H), 2.19 (t, J=8.6 Hz, 1H), 2.12-1.81 (m, 2H), 1.06 (s, 9H), 0.99 (s, 3H), 0.93 (dd, J=12.3, 8.8 Hz, 1H).

Example 43. Preparation of Compound HO-IV-H
(Step C)

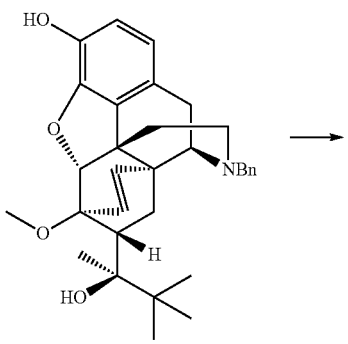

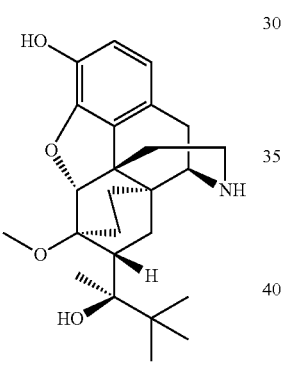

Compound 9 (560 mg, 1.12 mmol) was dissolved in 2-propanol (20 mL), followed by the addition of water (1 mL), 10% Pd/C (280 mg) and glacial acetic acid (0.2 mL). The mixture was reduced at 1 atmosphere of hydrogen pressure for 3 days. The reaction mixture was filtered over a pad of Celite and the filtrate was concentrated under reduced pressure. The residue was dissolved in a mixture of methanol (20 mL), water (1 mL) and glacial acetic acid (0.2 mL). After the addition of 10% Pd/C (280 mg) the mixture was reduced at 1 atmosphere of hydrogen pressure at 60° C. for 3 days. After cooling to room temperature the reaction mixture was filtered over a pad of Celite and the filtrate was concentrated under reduced pressure. The residue was purified by column chromatography (24 g of silica, 0-10% methanol in dichloromethane) to afford Compound HO-IV-H (228 mg, 49%).

Norbuprenorphine

MS and NMR data were in agreement with those obtained in previous examples.

Example 44. Preparation of Compound AcO-IIIB-Ac (step C)

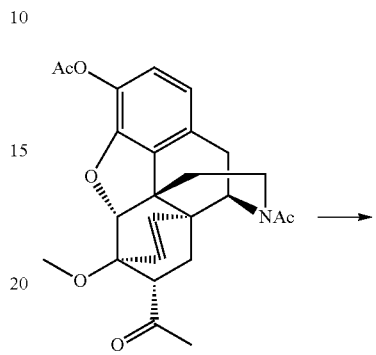

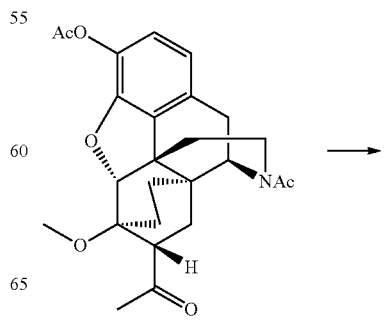

Compound AcO-II-Ac is dissolved in 2-propanol, followed by the addition of water, 10% Pd/C (10%) and glacial acetic acid. The mixture is reduced at 1 atmosphere of hydrogen pressure for 3 days at 80° C. After cooling to room temperature the reaction mixture is filtered over a pad of Celite and the filtrate is concentrated under reduced pressure. The residue is purified by column chromatography.

Example 45. Preparation of Compound HO-IV-Ac
(Step D)

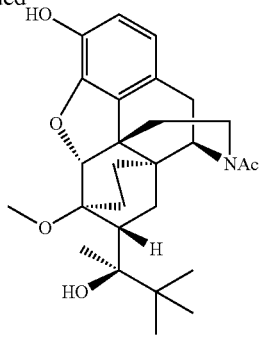

Dry toluene is added to a solution of tert-butylmagnesium chloride (1.7 M in THF). Under a nitrogen atmosphere a solution of Compound AcO-IIIB-Ac in dry toluene is added to the Grignard solution slowly by means of a syringe. The mixture is stirred at 60° C. for 3 h. After cooling to room temperature diethyl ether and water are added. The mixture is acidified with 1N aqueous HCl. Both layers are separated. The aqueous layer is extracted with EtOAc. The combined organic layers are dried over Na2SO4, filtered and concentrated under reduced. The residue is purified by column chromatography.

Example 46. Preparation of Compound HO-IV-Ac (Step C)

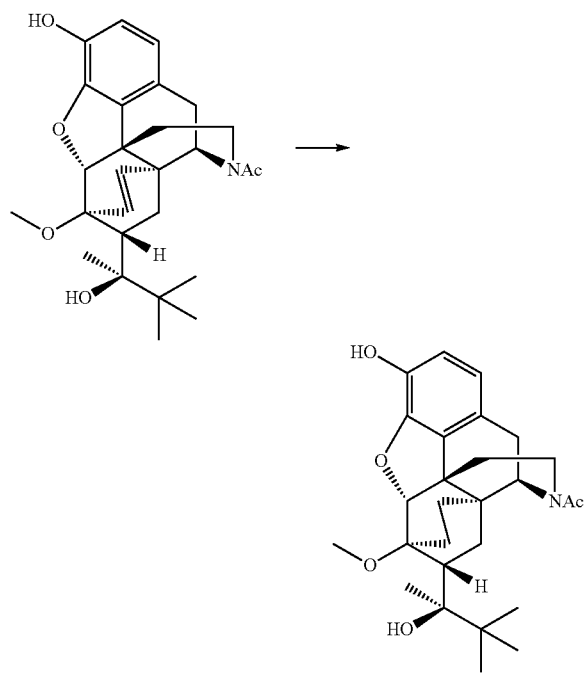

Compound HO-IIIA-Ac is dissolved in 2-propanol, followed by the addition of water, 10% Pd/C (10%) and glacial acetic acid). The mixture is reduced at 1 atmosphere of hydrogen pressure for 3 days at 80° C. After cooling to room temperature the reaction mixture is filtered over a pad of Celite and the filtrate is concentrated under reduced pressure. The residue is purified by column chromatography.

Example 47. Preparation of Compound HO-IV-H (Step I)

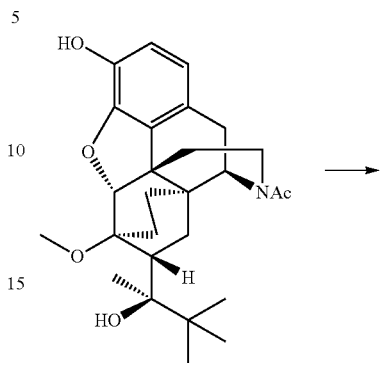

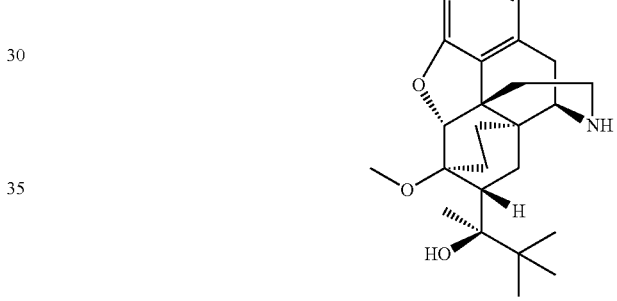

To a solution of HO-IV-Ac in THF at room temperature is added Schwartzs reagent in one portion. The resulting suspension is stirred under an argon atmosphere for 40 min, when the suspension turns pale red. The reaction mixture is evaporated to a thick oil, which is purified by column chromatography.

Example 48. Preparation of Compound HO-IV-H (Step I)

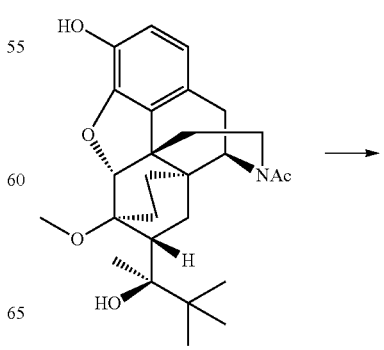

-continued

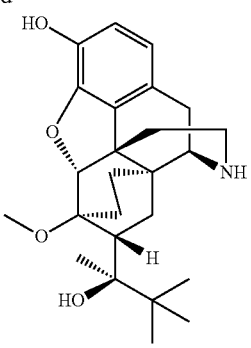

A mixture of HO-IV-Ac, KOH and diethylene glycol is stirred under an inert atmosphere at 170-180° C. for 7 h. The reaction mixture is then quenched with water (10 mL) and the products are extracted with dichloromethane. The combined organic layers are washed with water, brine, dried over Na2SO4 and concentrated. The product is isolated by column chromatography.

Exemplary methods, compounds and other embodiments of the present invention are set out in the following items:

Item 1. A method of preparing buprenorphine, or a salt thereof, from Compound HO-I-H, or a salt thereof:

(Compound HO-I-H)

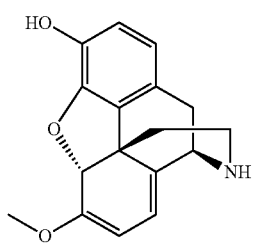

comprising:

(i)(A1) reacting Compound HO-I-H with cyclopropane carboxaldehyde followed by a hydride source; or (i)(A2) reacting Compound HO-I-H with cyclopropanecarboxylic acid halide followed by a reducing agent; or (i)(A3) reacting Compound HO-I-H with cyclopropylmethyl halide or activated cyclopropane methanol;

to provide Compound HO-I-MCP:

(Compound HO-I-MCP)

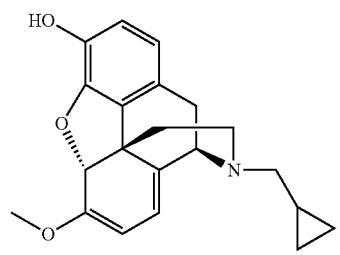

(ii)(B) reacting Compound HO-I-MCP with methyl vinyl ketone to provide Compound HO-II-MCP:

(Compound HO-II-MCP)

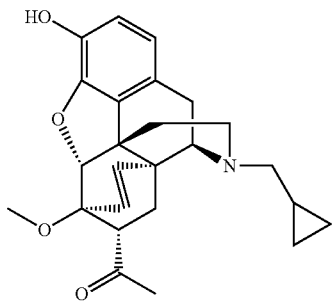

(iii)(C) reacting Compound HO-II-MCP with $H_2$ in the presence of a hydrogenation catalyst to provide Compound HO-IIIB-MCP:

(Compound HO-IIIB-MCP)

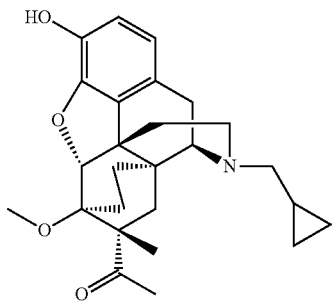

(iv)(D) reacting Compound HO-IIIB-MCP with tert-butylmagnesium halide to provide buprenorphine.

Item 2. A method of preparing buprenorphine, or a salt thereof, from Compound HO-I-H, or a salt thereof:

(Compound HO-I-H)

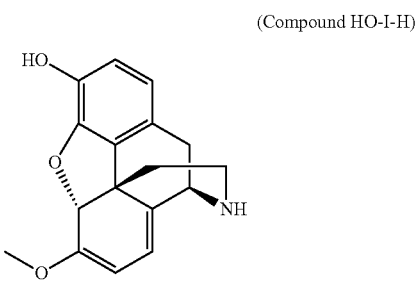 [SMILES: COC1=CC=C2[C@H]3Cc4ccc(O)c5c4[C@@]2(CCN3)[C@H]1O5]

comprising:

(i)(A1) reacting Compound HO-I-H with cyclopropane carboxaldehyde followed by a hydride source; or (i)(A2) reacting Compound HO-I-H with cyclopropanecarboxylic acid halide followed by a reducing agent; or (i)(A3) reacting Compound HO-I-H with cyclopropylmethyl halide or activated cyclopropane methanol;

to provide Compound HO-I-MCP:

(Compound HO-I-MCP)

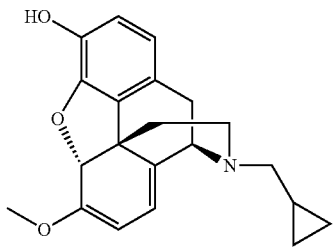

(ii)(B) reacting Compound HO-I-MCP with methyl vinyl ketone to provide Compound HO-II-MCP:

(Compound HO-II-MCP)

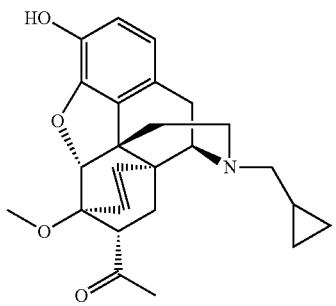

(iii)(D) reacting Compound HO-II-MCP with tert-butyl-magnesium halide to provide Compound HO-IIIA-MCP:

(Compound HO-IIIA-MCP)

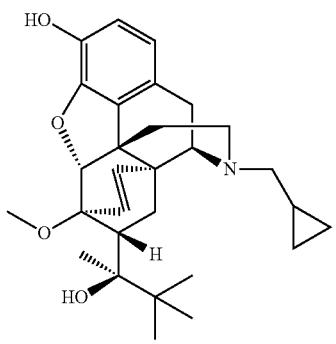

(iv)(C) reacting Compound HO-IIIA-MCP with $H_2$ in the presence of a hydrogenation catalyst to provide buprenorphine.

Item 3. A method of preparing buprenorphine, or a salt thereof, from Compound BnO-I-H, or a salt thereof:

(Compound BnO-I-H)

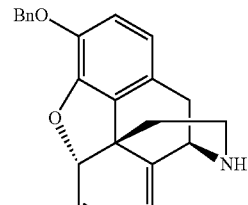

comprising:

(i)(A1) reacting Compound BnO-I-H with cyclopropane carboxaldehyde followed by a hydride source; or (i)(A2) reacting Compound BnO-I-H with cyclopropan-ecarboxylic acid halide followed by a reducing agent; or (i)(A3) reacting Compound BnO-I-H with cyclopropyl-methyl halide or activated cyclopropane methanol;

to provide Compound BnO-I-MCP:

(Compound BnO-I-MCP)

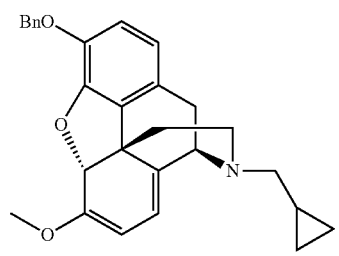

(ii)(B) reacting Compound BnO-I-MCP with methyl vinyl ketone to provide Compound BnO-II-MCP:

(Compound BnO-II-MCP)

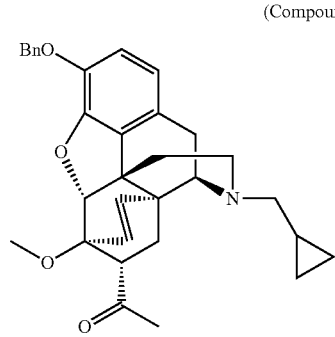

(iii)(D) reacting Compound BnO-II-MCP with tert-butyl-magnesium halide to provide Compound BnO-IIIA-MCP:

(Compound BnO-IIIA-MCP)

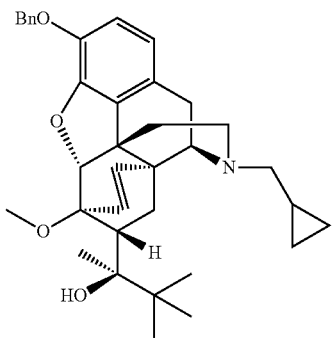

(iv)(C) reacting Compound BnO-IIIA-MCP with H₂ in the presence of a hydrogenation catalyst to provide buprenorphine.

Item 4. A method of preparing buprenorphine, or a salt thereof, from Compound MeO-I-H, or a salt thereof:

(Compound MeO-I-H)

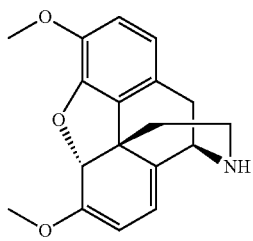

comprising:
(i)(A1) reacting Compound MeO-I-H with cyclopropane carboxaldehyde followed by a hydride source; or
(i)(A2) reacting Compound MeO-I-H with cyclopropanecarboxylic acid halide followed by a reducing agent; or
(i)(A3) reacting Compound MeO-I-H with cyclopropylmethyl halide or activated cyclopropane methanol;
to provide Compound MeO-I-MCP:

(Compound MeO-I-MCP)

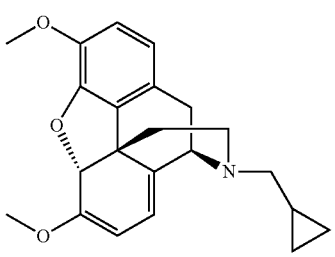

(ii)(B) reacting Compound MeO-I-MCP with methyl vinyl ketone to provide Compound MeO-II-MCP:

(Compound MeO-II-MCP)

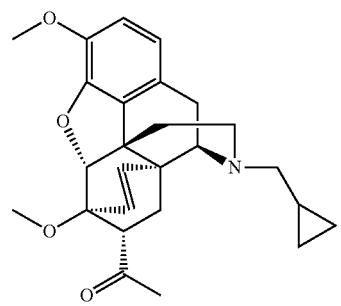

(iii)(C) reacting Compound MeO-II-MCP with H₂ in the presence of a hydrogenation catalyst to provide Compound MeO-IIIB-MCP:

(Compound MeO-IIIB-MCP)

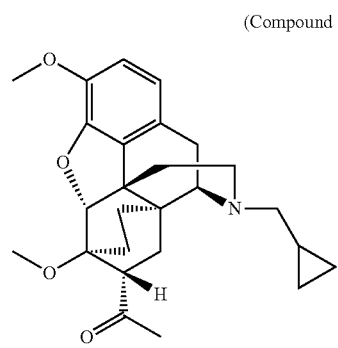

(iv)(D) reacting Compound MeO-IIIB-MCP with tert-butylmagnesium halide to provide Compound MeO-IV-MCP:

(Compound MeO-IV-MCP)

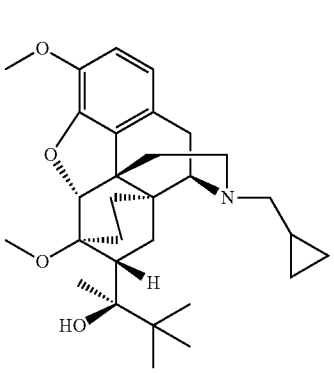

(v)(E) reacting a compound of Compound MeO-IV-MCP with a demethylating agent to provide buprenorphine.

Item 5. A method of preparing buprenorphine, or a salt thereof, from Compound MeO-I-H, or a salt thereof:

(Compound MeO-I-H)

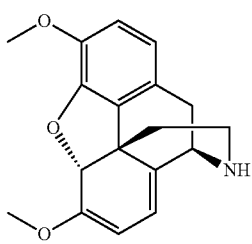

comprising:
(i)(A1) reacting Compound MeO-I-H with cyclopropane carboxaldehyde followed by a hydride source; or
(i)(A2) reacting Compound MeO-I-H with cyclopropanecarboxylic acid halide followed by a reducing agent; or
(i)(A3) reacting Compound MeO-I-H with cyclopropylmethyl halide or activated cyclopropane methanol;
to provide Compound MeO-I-MCP:

(Compound MeO-I-MCP)

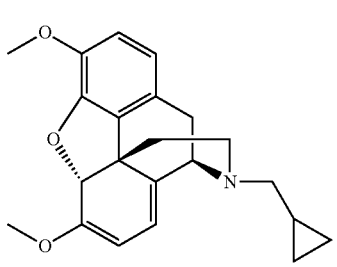

(ii)(B) reacting Compound MeO-I-MCP with methyl vinyl ketone to provide Compound MeO-II-MCP:

(Compound MeO-II-MCP)

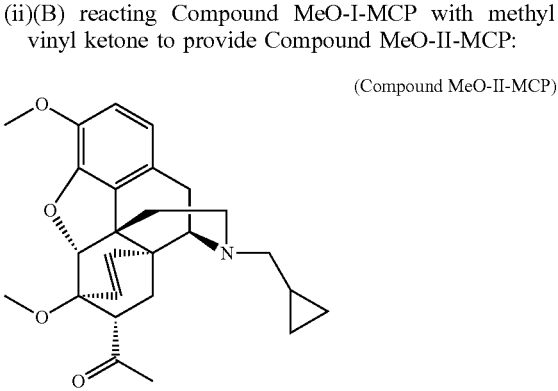

(iii)(D) reacting Compound MeO-II-MCP with tert-butylmagnesium halide to provide Compound MeO-IIIA-MCP:

(Compound MeO-IIIA-MCP)

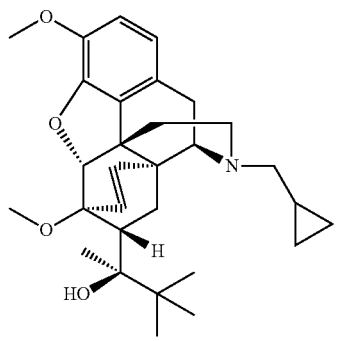

(iv)(C) reacting Compound MeO-IIIA-MCP with $H_2$ in the presence of a hydrogenation catalyst to provide a compound of Compound MeO-IV-MCP:

(Compound MeO-IV-MCP)

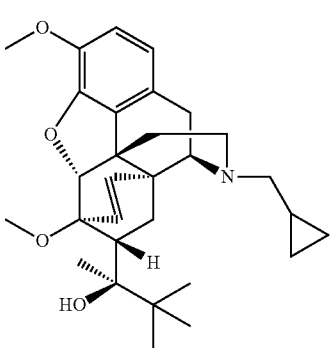

(v)(E) reacting a compound of Compound MeO-IV-MCP with a demethylating agent to provide buprenorphine.

Item 6. A method of preparing buprenorphine, or a salt thereof, from Compound MeO-I-H, or a salt thereof:

(Compound MeO-I-H)

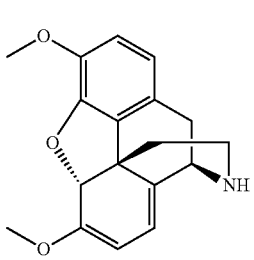

comprising:
(i)(A1) reacting Compound MeO-I-H with cyclopropane carboxaldehyde followed by a hydride source; or
(i)(A2) reacting Compound MeO-I-H with cyclopropanecarboxylic acid halide followed by a reducing agent; or
(i)(A3) reacting Compound MeO-I-H with cyclopropylmethyl halide or activated cyclopropane methanol;
to provide Compound MeO-I-MCP:

(Compound MeO-I-MCP)

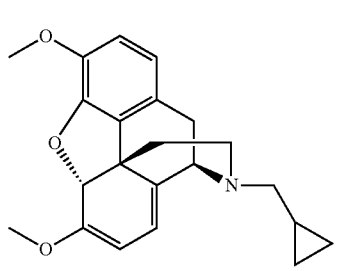

(ii)(B) reacting Compound MeO-I-MCP with methyl vinyl ketone to provide Compound MeO-II-MCP:

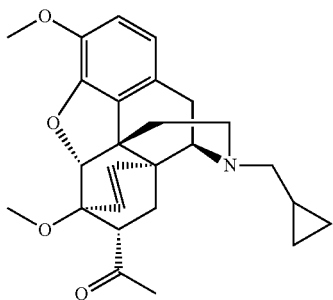
(Compound MeO-II-MCP)

(iii)(D) reacting Compound MeO-II-MCP with tert-butyl-magnesium halide to provide Compound MeO-IIIA-MCP:

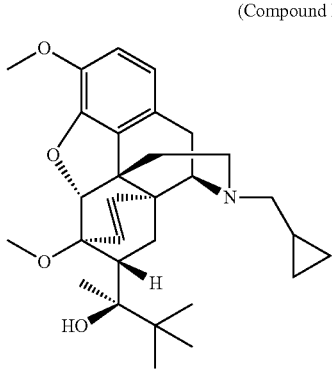
(Compound MeO-IIIA-MCP)

(iv)(E) reacting Compound MeO-IIIA-MCP with a demethylating agent to provide Compound HO-IIIA-MCP:

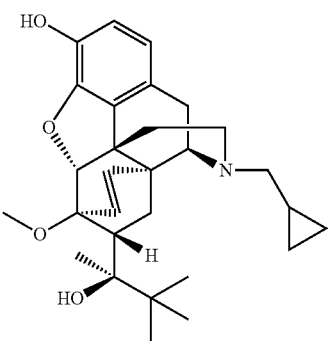
(Compound HO-IIIA-MCP)

(v)(C) reacting Compound HO-IIIA-MCP with $H_2$ in the presence of a hydrogenation catalyst to provide buprenorphine.

Item 7. A method of preparing buprenorphine, or a salt thereof, from Compound HO-I-Me, or a salt thereof:

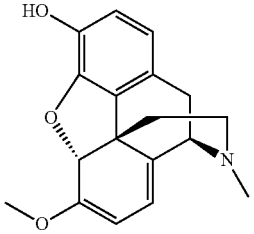
(Compound HO-I-Me)

comprising:
(i)(F) reacting Compound HO-I-Me with benzyl halide, benzyl sulfonate, or activated benzyl alcohol to provide Compound BnO-I-Me:

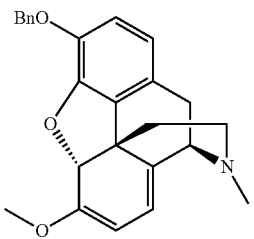
(Compound BnO-I-Me)

(ii)(E) reacting Compound BnO-I-Me with an azodicarboxylate followed by an acid or an addition salt thereof to provide Compound BnO-I-H:

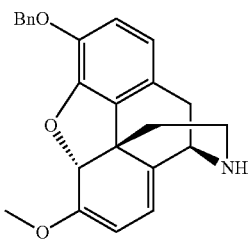
(Compound BnO-I-H)

(iii)(A1) reacting Compound BnO-I-H with cyclopropane carboxaldehyde followed by a hydride source; or
(iii)(A2) reacting Compound BnO-I-H with cyclopropanecarboxylic acid halide followed by a reducing agent; or
(iii)(A3) reacting Compound BnO-I-H with cyclopropylmethyl halide or activated cyclopropane methanol;
to provide Compound BnO-I-MCP:

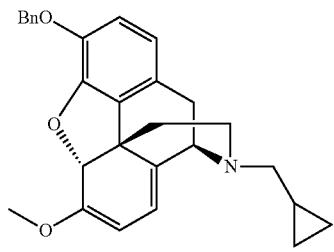
(Compound BnO-I-MCP)

(iv)(B) reacting Compound BnO-I-MCP with methyl vinyl ketone to provide Compound BnO-II-MCP:

(Compound BnO-II-MCP)

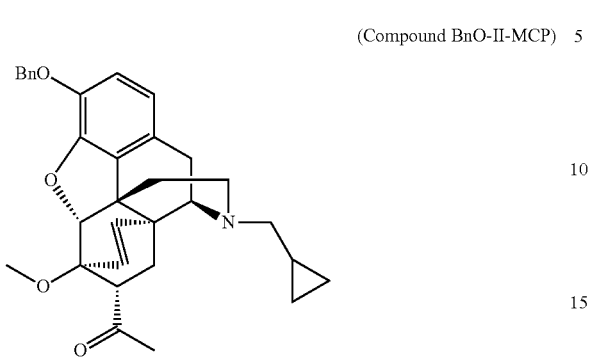

(v)(D) reacting Compound BnO-II-MCP with tert-butyl-magnesium halide to provide Compound BnO-IIIA-MCP:

(Compound BnO-IIIA-MCP)

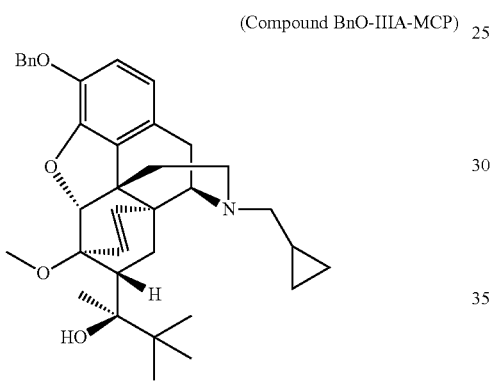

(vi)(C) reacting Compound BnO-IIIA-MCP with $H_2$ in the presence of a hydrogenation catalyst to provide buprenorphine.

Item 8. A method of preparing buprenorphine, or a salt thereof, from Compound HO-I-H, or a salt thereof:

(Compound HO-I-H)

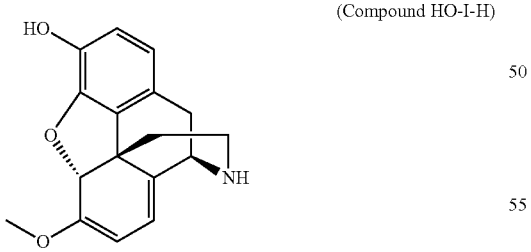

comprising:
(i)(A1) reacting Compound HO-I-H with cyclopropane carboxaldehyde followed by a hydride source; or
(i)(A2) reacting Compound HO-I-H with cyclopropanecarboxylic acid halide followed by a reducing agent; or
(i)(A3) reacting Compound HO-I-H with cyclopropylmethyl halide or activated cyclopropane methanol;

to provide Compound HO-I-MCP:

(Compound HO-I-MCP)

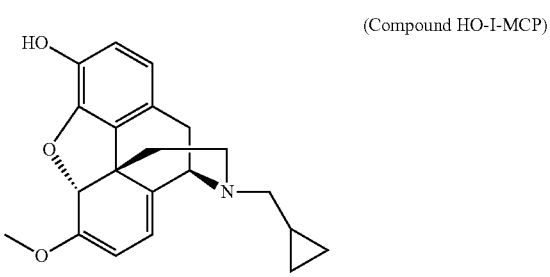 [SMILES: COC1=CC=C2[C@H]3Cc4ccc(O)c5c4[C@@]2(CCN3CC2CC2)[C@H]1O5]

(ii)(B) reacting Compound HO-I-MCP with methyl vinyl ketone to provide Compound HO-II-MCP:

(Compound HO-II-MCP)

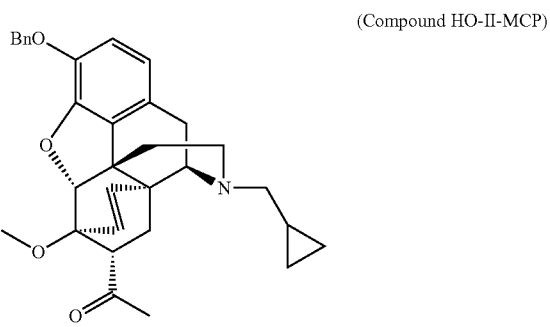 [SMILES: CO[C@]12C=C[C@@]3(C[C@@H]1C(C)=O)[C@H]1Cc4ccc(OCc5ccccc5)c5c4[C@@]3(CCN1CC1CC1)[C@H]2O5]

(iii)(F) reacting Compound HO-II-MCP with benzyl halide, benzyl sulfonate, or activated benzyl alcohol to provide Compound BnO-II-MCP:

(Compound BnO-II-MCP)

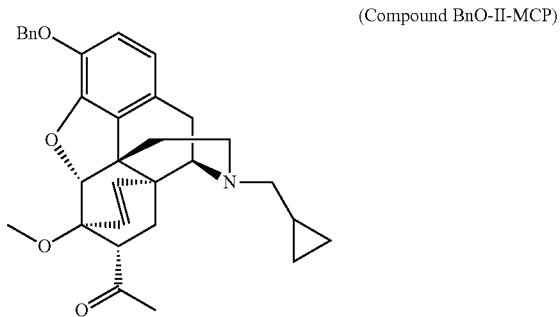 [SMILES: CO[C@]12C=C[C@@]3(C[C@@H]1C(C)=O)[C@H]1Cc4ccc(OCc5ccccc5)c5c4[C@@]3(CCN1CC1CC1)[C@H]2O5]

(iv)(D) reacting Compound BnO-II-MCP with tert-butyl-magnesium halide to provide Compound BnO-IIIA-MCP:

(Compound BnO-IIIA-MCP)

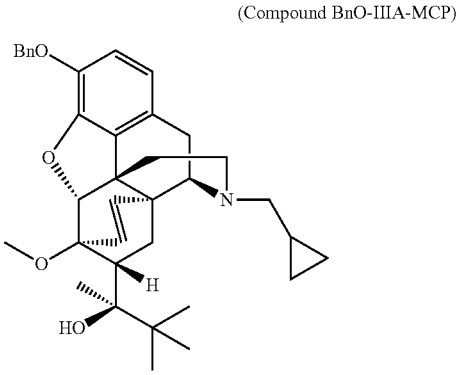 [SMILES: CO[C@]12C=C[C@@]3(C[C@@H]1[C@](C)(O)C(C)(C)C)[C@H]1Cc4ccc(OCc5ccccc5)c5c4[C@@]3(CCN1CC1CC1)[C@H]2O5]

(v)(C) reacting Compound BnO-IIIA-MCP with H$_2$ in the presence of a hydrogenation catalyst to provide buprenorphine.

Item 9. A method of preparing buprenorphine, or a salt thereof, from Compound HO-I-H, or a salt thereof:

(Compound HO-I-H)

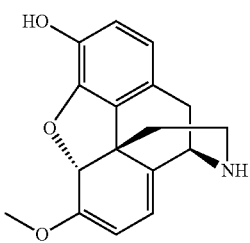

comprising:

(i)(A1) reacting Compound HO-I-H with cyclopropane carboxaldehyde followed by a hydride source; or (i)(A2) reacting Compound HO-I-H with cyclopropanecarboxylic acid halide followed by a reducing agent; or (i)(A3) reacting Compound HO-I-H with cyclopropylmethyl halide or activated cyclopropane methanol;

to provide Compound HO-I-MCP:

(Compound HO-I-MCP)

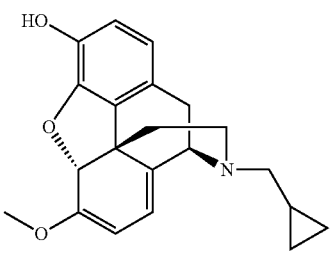

(ii)(F) reacting Compound HO-I-MCP with benzyl halide, benzyl sulfonate, or activated benzyl alcohol to provide Compound BnO-I-MCP:

(Compound BnO-I-MCP)

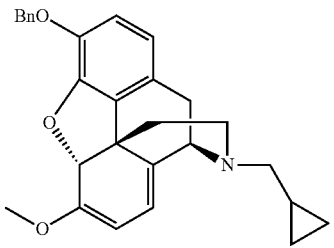

(iii)(B) reacting Compound BnO-I-MCP with methyl vinyl ketone to provide Compound BnO-II-MCP:

(Compound BnO-II-MCP)

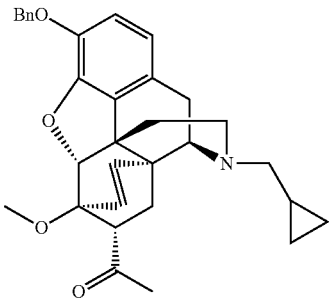

(iv)(D) reacting Compound BnO-II-MCP with tert-butylmagnesium halide to provide Compound BnO-IIIA-MCP:

(Compound BnO-IIIA-MCP)

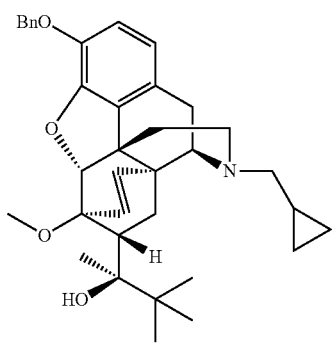

(v)(C) reacting Compound BnO-IIIA-MCP with H$_2$ in the presence of a hydrogenation catalyst to provide buprenorphine.

Item 10. A method of preparing buprenorphine, or a salt thereof, from Compound HO-I-H, or a salt thereof:

(Compound HO-I-H)

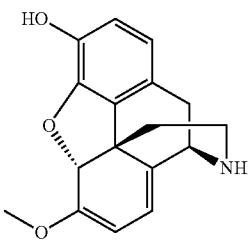

comprising:

(i)(F) reacting Compound HO-I-H with benzyl halide, benzyl sulfonate, or activated benzyl alcohol to provide Compound BnO-I-Bn:

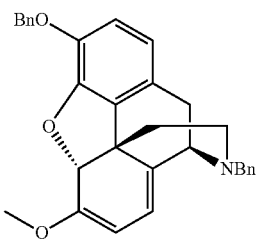
(Compound BnO-I-Bn)

(ii)(B) reacting Compound BnO-I-Bn with methyl vinyl ketone to provide Compound BnO-II-Bn:

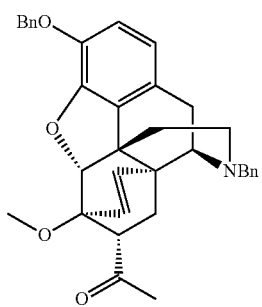
(Compound BnO-II-Bn)

(iii)(D) reacting Compound BnO-II-Bn with tert-butyl-magnesium halide to provide Compound BnO-IIIA-Bn:

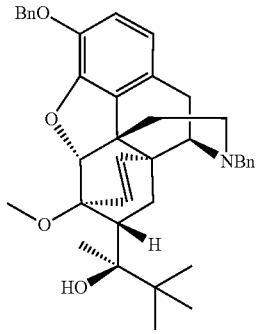
(Compound BnO-IIIA-Bn)

(iv)(C) reacting Compound BnO-IIIA-Bn with $H_2$ in the presence of a hydrogenation catalyst to provide a compound of Compound HO-IV-H:

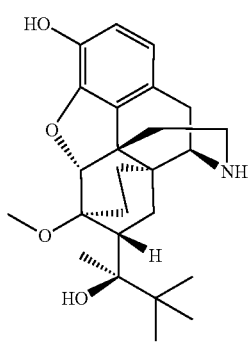
(Compound HO-IV-H)

(v)(A1) reacting Compound HO-IV-H with cyclopropane carboxaldehyde followed by a hydride source; or (v)(A2) reacting Compound HO-IV-H with cyclopropanecarboxylic acid halide followed by a reducing agent; or (v)(A3) reacting Compound HO-IV-H with cyclopropyl-methyl halide or activated cyclopropane methanol;

to provide buprenorphine.

Item 11. A method of preparing buprenorphine, or a salt thereof, from Compound HO-I-H, or a salt thereof:

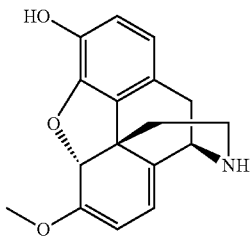
(Compound HO-I-H)

comprising:

(i)(G) reacting Compound HO-I-H with optionally substituted benzoyl halide to provide Compound HO-I-Ac:

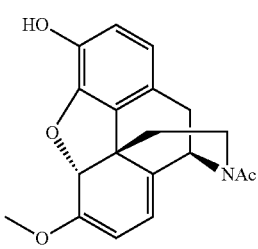
(Compound HO-I-Ac)

(ii)(F) reacting Compound HO-I-Ac with benzyl halide, benzyl sulfonate, or activated benzyl alcohol to provide Compound BnO-I-Ac:

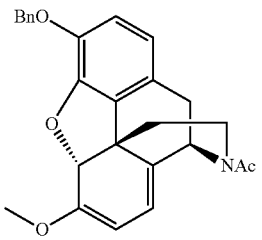
(Compound BnO-I-Ac)

(iii)(H) reacting Compound BnO-I-Ac with lithium aluminum hydride to provide Compound BnO-I-Bn:

(Compound BnO-I-Bn)

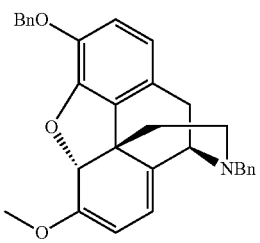

(iv)(B) reacting Compound BnO-I-Bn with methyl vinyl ketone to provide Compound BnO-II-Bn:

(Compound BnO-II-Bn)

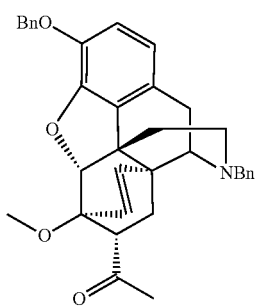

(v)(D) reacting Compound BnO-II-Bn with tert-butylmagnesium halide to provide Compound BnO-IIIA-Bn:

(Compound BnO-IIIA-Bn)

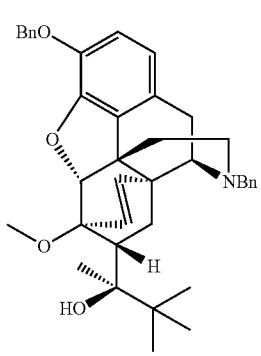

(vi)(C) reacting Compound BnO-IIIA-Bn with $H_2$ in the presence of a hydrogenation catalyst to provide a compound of Compound HO-IV-H:

(Compound HO-IV-H)

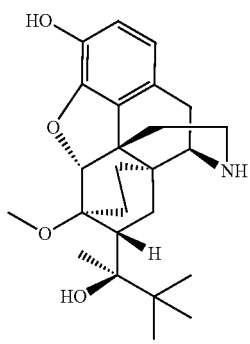

(vii)(A1) reacting Compound HO-IV-H with cyclopropane carboxaldehyde followed by a hydride source; or (vii)(A2) reacting Compound HO-IV-H with cyclopropanecarboxylic acid halide followed by a reducing agent; or (vii)(A3) reacting Compound HO-IV-H with cyclopropylmethyl halide or activated cyclopropane methanol;

to provide buprenorphine.

Item 12. A method of preparing buprenorphine, or a salt thereof, from Compound HO-I-H, or a salt thereof:

(Compound HO-I-H)

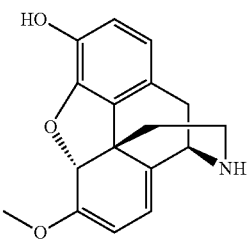

comprising:

(i)(G) reacting Compound HO-I-H with optionally substituted benzoyl halide to provide Compound AcO-I-Ac:

(Compound AcO-I-Ac)

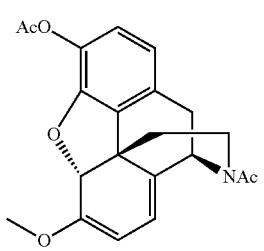

(ii)(B) reacting Compound AcO-I-Ac with methyl vinyl ketone to provide Compound AcO-II-Ac:

(Compound AcO-II-Ac)

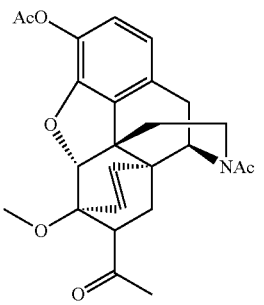

(iii)(D) reacting Compound AcO-II-Ac with tert-butylmagnesium halide to provide Compound HO-IIIA-Ac:

(Compound HO-IIIA-Ac)

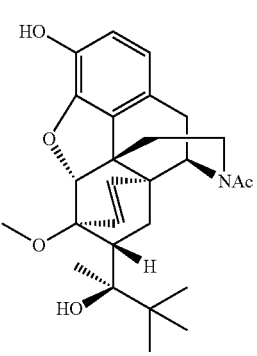

(iv)(H) reacting Compound HO-IIIA-Ac with lithium aluminum hydride to provide Compound HO-IIIA-Bn:

(Compound HO-IV-Bn)

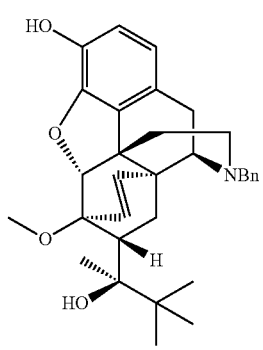

(v)(C) reacting Compound HO-IV-Bn with $H_2$ in the presence of a hydrogenation catalyst to provide a compound of Compound HO-IV-H:

(Compound HO-IV-H)

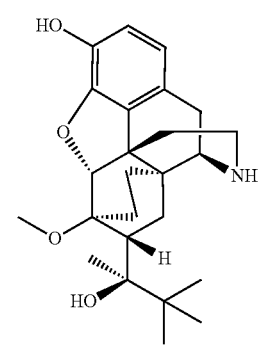

(vi)(A1) reacting Compound HO-IV-H with cyclopropane carboxaldehyde followed by a hydride source; or (vi)(A2) reacting Compound HO-IV-H with cyclopropanecarboxylic acid halide followed by a reducing agent; or (vi)(A3) reacting Compound HO-IV-H with cyclopropylmethyl halide or activated cyclopropane methanol;

to provide buprenorphine.

Item 13. A method of preparing buprenorphine, or a salt thereof, from Compound HO-I-H, or a salt thereof:

(Compound HO-I-H)

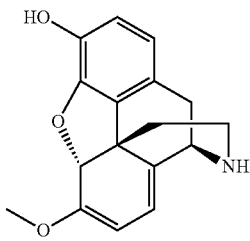

comprising:
(i)(G) reacting Compound HO-I-H with acyl halide to provide Compound AcO-I-Ac:

(Compound AcO-I-Ac)

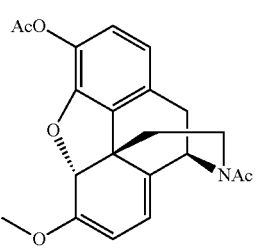

(ii)(B) reacting Compound AcO-I-Ac with methyl vinyl ketone to provide Compound AcO-II-Ac:

(Compound AcO-II-Ac)

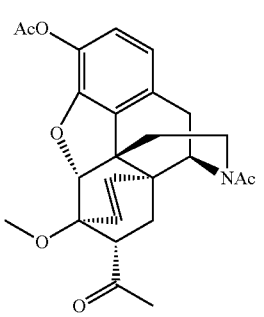

(iii)(D) reacting Compound AcO-II-Ac with tert-butyl-magnesium halide to provide Compound HO-IIIA-Bn:

(Compound HO-IIIA-Ac)

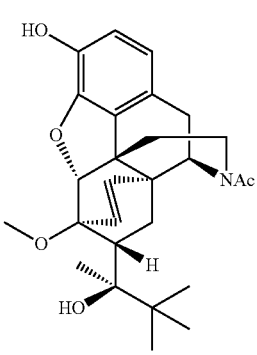

(iv)(C) reacting Compound HO-IIIA-Ac with $H_2$ in the presence of a hydrogenation catalyst to provide a compound of Compound HO-IV-Ac:

(Compound HO-IV-Ac)

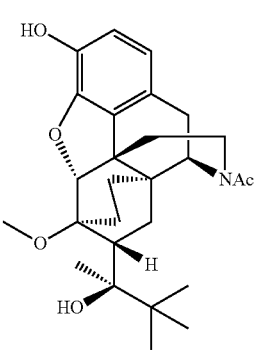

(v)(I) reacting Compound HO-IV-Ac with Schwartz's reagent or base to provide Compound HO-IV-H:

(Compound HO-IV-H)

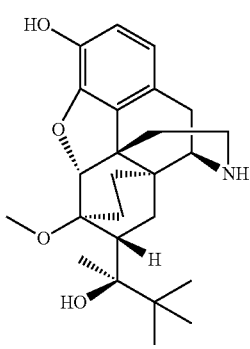

(vi)(A1) reacting Compound HO-IV-H with cyclopropane carboxaldehyde followed by a hydride source; or (vi)(A2) reacting Compound HO-IV-H with cyclopropanecarboxylic acid halide followed by a reducing agent; or (vi)(A3) reacting Compound HO-IV-H with cyclopropylmethyl halide or activated cyclopropane methanol;

to provide buprenorphine.

Item 14. A method of preparing buprenorphine, or a salt thereof, from Compound HO-I-H, or a salt thereof:

(Compound HO-I-H)

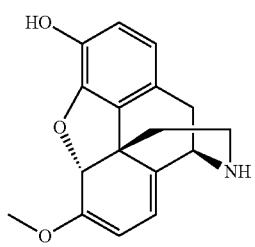

comprising:

(i)(G) reacting Compound HO-I-H with optionally substituted benzoyl halide to provide Compound AcO-I-Ac:

(Compound AcO-I-Ac)

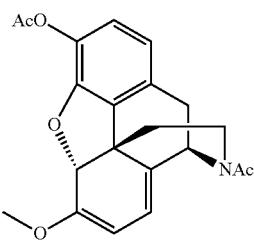

(ii)(B) reacting Compound AcO-I-Ac with methyl vinyl ketone to provide Compound AcO-II-Ac:

(Compound AcO-II-Ac)

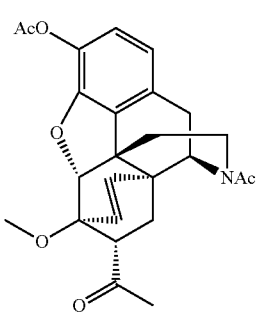

(iii)(C) reacting Compound HO-IIIA-Ac with $H_2$ in the presence of a hydrogenation catalyst to provide a compound of Compound AcO-IIIB-Ac:

(Compound AcO-IIIB-Ac)

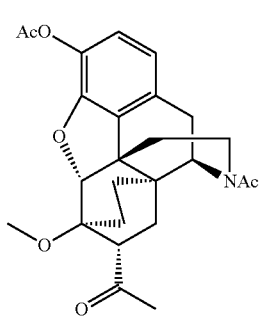

(iv)(D) reacting Compound AcO-II-Ac with tert-butylmagnesium halide to provide Compound HO-IV-Ac:

(Compound HO-IV-Ac)

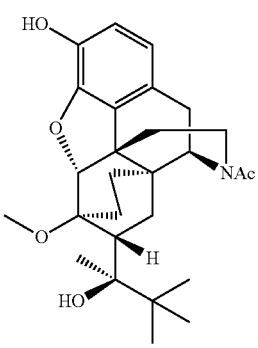

(v)(1) reacting Compound HO-IV-Ac with Schwartz's reagent or base to provide Compound HO-IV-H:

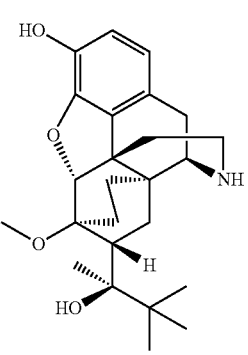

(Compound HO-IV-H)

(vi)(A1) reacting Compound HO-IV-H with cyclopropane carboxaldehyde followed by a hydride source; or (vi)(A2) reacting Compound HO-IV-H with cyclopropanecarboxylic acid halide followed by a reducing agent; or (vi)(A3) reacting Compound HO-IV-H with cyclopropylmethyl halide or activated cyclopropane methanol;

to provide buprenorphine.

Item 15. A method according to any of items 4-7, wherein the demethylating agent of step (E) is a thiolate.

Item 16. A method according to any of items 4-7, wherein the demethylating agent of step (E) is a dodecane thiolate.

Item 17. A method according to any of items 4-7 and 15-16, wherein step (E) is performed in a solvent comprising a polar aprotic solvent.

Item 18. A method according to any of items 4-7 and 15-16, wherein step (E) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

Item 19. A method according to any of items 4-7 and 15-16, wherein the demethylating agent of step (E) is reacted at a temperature within the range of about 50° C. to about 190° C., for a period of time within the range of about 4 hours to about 2 days.

Item 20. A method according to any of items 7-11, wherein the benzyl halide of step (F) is benzyl chloride or benzyl bromide.

Item 21. A method according to any of items 7-11 and 20, wherein step (F) is performed in the presence of a strong base.

Item 22. A method according to any of items 7-11 and 20, wherein step (F) is performed in the presence of an alkali metal hydride.

Item 23. A method according to any of items 7-11 and 20-22, wherein step (F) is performed in a solvent comprising a polar aprotic solvent.

Item 24. A method according to any of items 7-11 and 20-22, wherein step (F) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

Item 25. A method according to any of items 7-11 and 20-24, wherein the benzyl halide, benzyl sulfonate, or activated benzyl alcohol of step (F) is reacted at one or more temperatures within the range of about of about −20° C. to about 40° C., for a period of time within the range of about 6 hours to about 2 days.

Item 26. A method according to any of items 11-12, wherein step (H) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

Item 27. A method according to any of items 11-12 and 26, wherein the lithium aluminum hydride of step (H) is reacted at a temperature within the range of about 40° C. to about 120° C.

Item 28. A method according to any of items 11-14 and 26-27, wherein step (G) is performed in the presence of a trialkylamine, e.g., triethylamine, diisopropylethylamine, 4-methyl-morpholine, or N-methyl-piperidine.

Item 29. A method according to any of items 11-14 and 26-28, wherein step (G) is performed in a solvent comprising dichloromethane, chloroform, toluene, 1,4-dioxane, diethyl ether, benzene, or a mixture thereof.

Item 30. A method according to any of items 11-14 and 26-29, wherein the acyl halide of step (G) is reacted at one or more temperatures within the range of about of about −20° C. to about 40° C., for a period of time within the range of about 30 minutes to about 8 hours.

Item 31. A method according to item 13 or 14, wherein step (I) comprises reacting Compound HO-IV-Ac with Schwartz's reagent.

Item 32. A method according to item 31, wherein step (I) is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

Item 33. A method according to item 31 or 32, wherein the Schwartz's reagent is reacted at a temperature within the range of about 15° C. to about 40° C., for a period of time within the range of about 5 minutes to about 3 hours.

Item 34. A method according to item 13 or 14, wherein step (I) comprises reacting Compound HO-IV-Ac with base, e.g., KOH.

Item 35. A method according to item 34, wherein step (I) is performed in a solvent comprising a high-boiling-point polar protic or aprotic solvent, e.g., ethylene glycol, diethylene glycol, N-methylpyrrolidone, dimethylformamide, or dimethylsulfoxide.

Item 36. A method according to item 34 or 35, wherein the base is reacted at a temperature within the range of about 50° C. to about 240° C., for a period of time within the range of about 4 hours to about 2 days.

Item 37. A method according to any of items 1-36, comprising step (A1).

Item 38. A method according to item 37, wherein the hydride source of step (A1) is formic acid or sodium cyanoborohydride.

Item 39. A method according to item 37, wherein the hydride source of step (A1) is formic acid.

Item 40. A method according to any of items 37-39, wherein step (A1) is catalyzed by a ruthenium(II) complex.

Item 41. A method according to any of items 37-39, wherein step (A1) is catalyzed by dichloro(p-cymene)ruthenium(II) dimer.

Item 42. A method according to any of items 37-41, wherein step (A1) is performed in a solvent comprising a polar aprotic solvent.

Item 43. A method according to any of items 37-41, wherein step (A1) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

Item 44. A method according to any of items 37-43, wherein step (A1) is performed in the presence of a trialkylamine.

Item 45. A method according to any of items 37-43, wherein step (A1) is performed in the presence of triethylamine, diisopropylethylamine, 4-methyl-morpholine, or N-methyl-piperidine.

Item 46. A method according to any of items 37-45, wherein the cyclopropane carboxaldehyde of step (A1) is reacted at a temperature within the range of about 30° C. to about 90° C., for a period of time within the range of about 30 minutes to about 5 hours.

Item 47. A method according to any of items 1-36, comprising step (A2).

Item 48. A method according to item 47, wherein the cyclopropanecarboxylic acid halide is cyclopropanecarboxylic acid chloride or cyclopropanecarboxylic acid bromide.

Item 49. A method according to item 47 or 48, wherein the reducing agent is LiAlH$_4$ or NaBH$_4$.

Item 50. A method according to any of items 47-49, wherein the reaction with cyclopropanecarboxylic acid halide of step (A2) is performed in a solvent comprising a nonpolar solvent.

Item 51. A method according to any of items 47-49, wherein the reaction with cyclopropanecarboxylic acid halide of step (A2) is performed in a solvent comprising dichloromethane, chloroform, toluene, 1,4-dioxane, diethyl ether, benzene, or a mixture thereof.

Item 52. A method according to any of items 47-51, wherein the reaction with a reducing agent of step (A2) is performed in a solvent comprising a polar aprotic solvent.

Item 53. A method according to any of items 47-51, wherein the reaction with a reducing agent of step (A2) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

Item 54. A method according to any of items 47-53, wherein the cyclopropanecarboxylic acid halide of step (A2) is reacted at one or more temperatures within the range of about −20° C. to about 40° C., for a period of time within the range of about 6 hours to about 2 days.

Item 55. A method according to any of items 47-54, wherein the reducing agent of step (A2) is reacted at a temperature within the range of about 35° C. to about 85° C., for a period of time within the range of about 5 minutes to about 3 hours.

Item 56. A method according to any of items 1-36, comprising step (A3).

Item 57. A method according to item 56, wherein the cyclopropylmethyl halide is cyclopropylmethyl chloride or cyclopropylmethyl bromide.

Item 58. A method according to item 56 or 57, wherein step (A3) is performed in a solvent comprising a polar protic solvent.

Item 59. A method according to item 56 or 57, wherein step (A3) is performed in a solvent comprising n-butanol, isopropanol, ethanol, methanol, water, or a mixture thereof.

Item 60. A method according to any of items 56-59, wherein step (A3) is performed in the presence of a trialkylamine.

Item 61. A method according to any of items 56-59, wherein step (A3) is performed in the presence of triethylamine, diisopropylethylamine, 4-methyl-morpholine, or N-methyl-piperidine.

Item 62. A method according to any of items 56-61, wherein the cyclopropylmethyl halide or activated cyclopropane methanol of step (A3) is reacted a temperature within the range of about 40° C. to about 120° C., for a period of time within the range of about 30 minutes to about 6 hours.

Item 63. A method according to any of items 1-62, wherein step (B) is performed in a solvent comprising a nonpolar solvent.

Item 64. A method according to any of items 1-62, wherein step (B) is performed in a solvent comprising dichloromethane, chloroform, toluene, 1,4-dioxane, diethyl ether, benzene, or a mixture thereof.

Item 65. A method according to any of items 1-64, wherein the methyl vinyl ketone of step (B) is reacted at a temperature within the range of about 40° C. to about 120° C. for a period of time within the range of about 2 hours to about 2 days.

Item 66. A method according to any of items 1-65, wherein the hydrogenation catalyst of step (C) comprises nickel, palladium, platinum, rhodium, or ruthenium.

Item 67. A method according to any of items 1-65, wherein the hydrogenation catalyst of step (C) comprises platinum or palladium supported on carbon.

Item 68. A method according to any of items 1-67, wherein step (C) is performed in a solvent comprising a polar protic or aprotic solvent.

Item 69. A method according to any of items 1-67, wherein step (C) is performed in a solvent comprising n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

Item 70. A method according to any of items 1-69, wherein the hydrogen of step (C) is reacted at a temperature within the range of about 15° C. to about 120° C., for a period of time within the range of about 6 hours to about 3 days.

Item 71. A method according to any of items 1-70, wherein the hydrogen of step (C) is reacted at a pressure within the range of about 1 atm. to about 3 atm.

Item 72. A method according to any of items 1-71, wherein the tert-butylmagnesium halide of step (D) is tert-butylmagnesium chloride or tert-butylmagnesium bromide.

Item 73. A method according to any of items 1-72, wherein step (D) is performed in a solvent comprising a nonpolar solvent.

Item 74. A method according to any of items 1-73, wherein step (D) is performed in a solvent comprising tert-butylmethyl ether, 2-methyl-tetrahydrofuran, diethyl ether, dimethoxymethane, benzene, toluene, or a mixture of thereof.

Item 75. A method according to any of items 1-74, wherein the tert-butylmagnesium halide of step (D) is reacted at a temperature within the range of about 15° C. to about 100° C. for a period of time within the range of about 30 minutes to about 8 hours.

Item 76. A compound of Formula I-Ac:

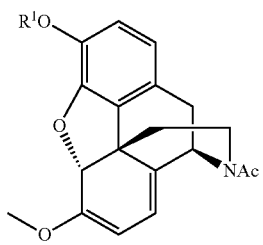

Formula I-Ac wherein Ac is optionally substituted benzoyl; and R¹ is H, Bn, or optionally substituted benzoyl.

Item 77. A compound of Formula II-Ac:

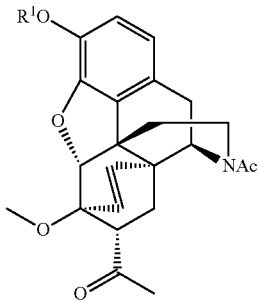

Formula II-Ac wherein Ac and R¹ are each independently optionally substituted benzoyl.

Item 78. A compound of Formula IIIA-Ac:

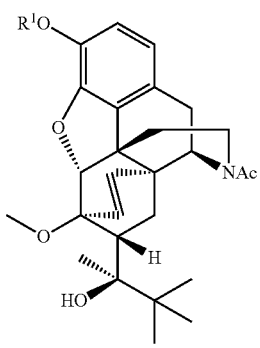

Formula IIIA-Ac wherein Ac is optionally substituted benzoyl, and R¹ is H.

Item 79. A compound of Formula IIIA-Bn:

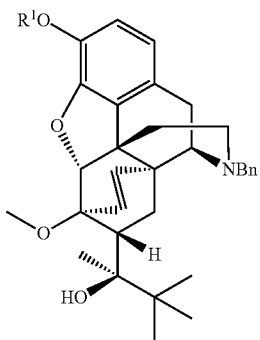

Formula IIIA-Bn wherein R¹ is H or Bn.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A method of preparing buprenorphine, or a salt thereof, (1) from Compound HO-I-H, or a salt thereof:

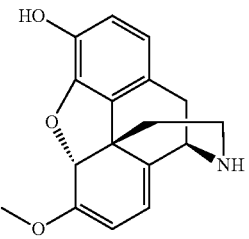

(Compound HO-I-H)

comprising:

(i)(A1) reacting Compound HO-I-H with cyclopropane carboxaldehyde followed by a hydride source; or (i)(A2) reacting Compound HO-I-H with cyclopropanecarboxylic acid halide followed by a reducing agent; or (i)(A3) reacting Compound HO-I-H with cyclopropylmethyl halide or activated cyclopropane methanol;

to provide Compound HO-I-MCP:

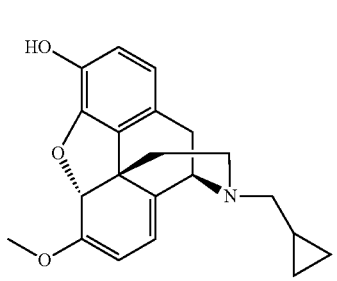

(Compound HO-I-MCP)

(ii)(B) reacting Compound HO-I-MCP with methyl vinyl ketone to provide Compound HO-II-MCP:

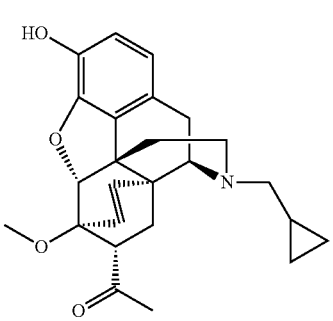

(Compound HO-II-MCP)

and either:

(iii)(C) reacting Compound HO-II-MCP with H₂ in the presence of a hydrogenation catalyst to provide Compound HO-IIIB-MCP:

(Compound HO-IIIB-MCP)

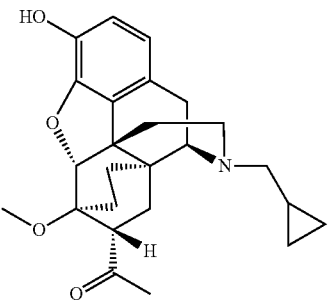

(iv)(D) reacting Compound HO-IIIB-MCP with tert-butylmagnesium halide to provide buprenorphine;

or (iii)(D) reacting Compound HO-II-MCP with tert-butyl-magnesium halide to provide Compound HO-IIIA-MCP:

(Compound HO-IIIA-MCP)

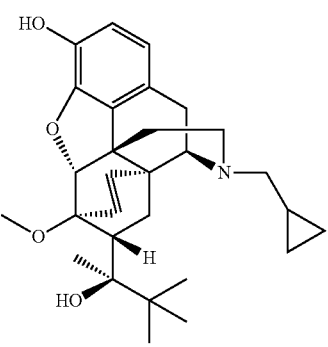

(iv)(C) reacting Compound HO-IIIA-MCP with H$_2$ in the presence of a hydrogenation catalyst to provide buprenorphine; or (2) from Compound BnO-I-H, or a salt thereof:

(Compound BnO-I-H)

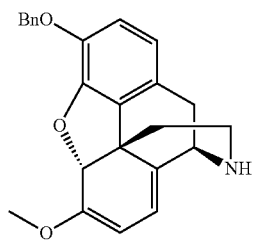

comprising:

(i)(A1) reacting Compound BnO-I-H with cyclopropane carboxaldehyde followed by a hydride source; or (i)(A2) reacting Compound BnO-I-H with cyclopropan-ecarboxylic acid halide followed by a reducing agent; or (i)(A3) reacting Compound BnO-I-H with cyclopropyl-methyl halide or activated cyclopropane methanol;

to provide Compound BnO-I-MCP:

(Compound BnO-I-MCP)

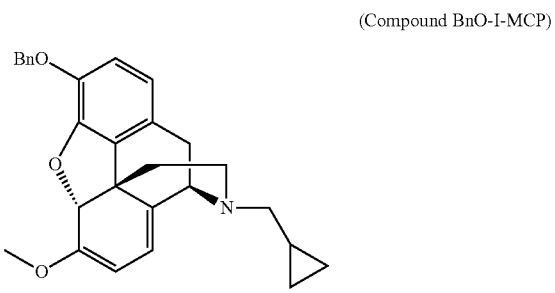 [SMILES: COC1=CC=C2[C@H]3Cc4ccc(OCc5ccccc5)c5c4[C@@]2(CCN3CC2CC2)[C@H]1O5]

(ii)(B) reacting Compound BnO-I-MCP with methyl vinyl ketone to provide Compound BnO-II-MCP:

(Compound BnO-II-MCP)

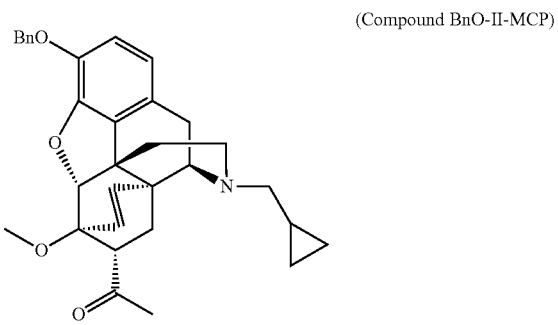 [SMILES: CO[C@]12C=C[C@@]3(C[C@@H]1C(C)=O)[C@H]1Cc4ccc(OCc5ccccc5)c5c4[C@@]3(CCN1CC1CC1)[C@H]2O5]

(iii)(D) reacting Compound BnO-II-MCP with tert-butyl-magnesium halide to provide Compound BnO-IIIA-MCP:

(Compound BnO-IIIA-MCP)

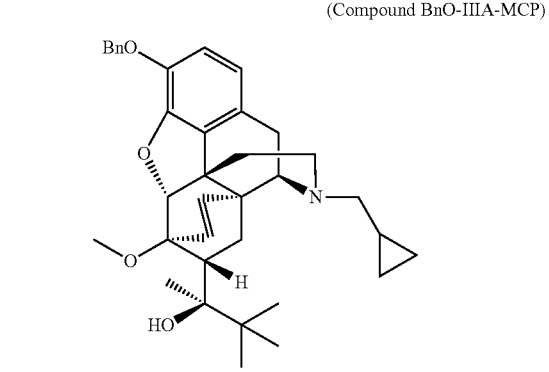 [SMILES: CO[C@]12C=C[C@@]3(C[C@@H]1[C@](C)(O)C(C)(C)C)[C@H]1Cc4ccc(OCc5ccccc5)c5c4[C@@]3(CCN1CC1CC1)[C@H]2O5]

(iv)(C) reacting Compound BnO-IIIA-MCP with H$_2$ in the presence of a hydrogenation catalyst to provide buprenorphine; or (3) from Compound MeO-I-H, or a salt thereof:

(Compound MeO-I-H)

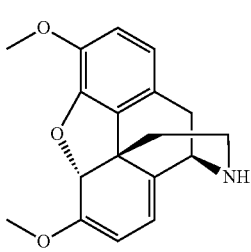

comprising:

(i)(A1) reacting Compound MeO-I-H with cyclopropane carboxaldehyde followed by a hydride source; or (i)(A2) reacting Compound MeO-I-H with cyclopropanecarboxylic acid halide followed by a reducing agent; or (i)(A3) reacting Compound MeO-I-H with cyclopropylmethyl halide or activated cyclopropane methanol;

to provide Compound MeO-I-MCP:

(Compound MeO-I-MCP)

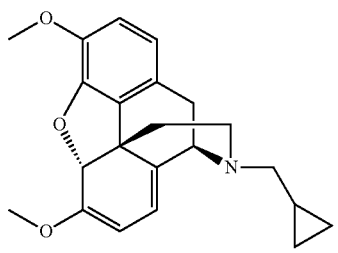

(ii)(B) reacting Compound MeO-I-MCP with methyl vinyl ketone to provide Compound MeO-II-MCP:

(Compound MeO-II-MCP)

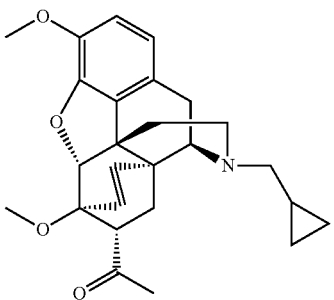

and either:

(iii)(C) reacting Compound MeO-II-MCP with H₂ in the presence of a hydrogenation catalyst to provide Compound MeO-IIIB-MCP:

(Compound MeO-IIIB-MCP)

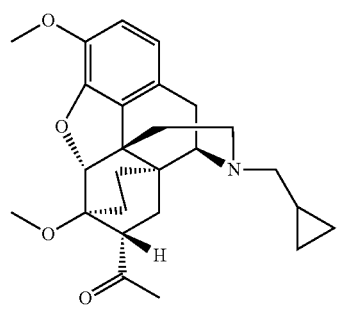

(iv)(D) reacting Compound MeO-IIIB-MCP with tert-butylmagnesium halide to provide Compound MeO-IV-MCP:

(Compound MeO-IV-MCP)

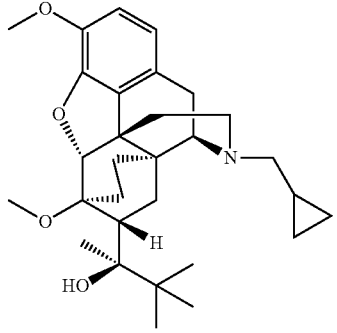

(v)(E) reacting a compound of Compound MeO-IV-MCP with a demethylating agent to provide buprenorphine; or (iii)(D) reacting Compound MeO-II-MCP with tert-butylmagnesium halide to provide Compound MeO-IIIA-MCP:

(Compound MeO-IIIA-MCP)

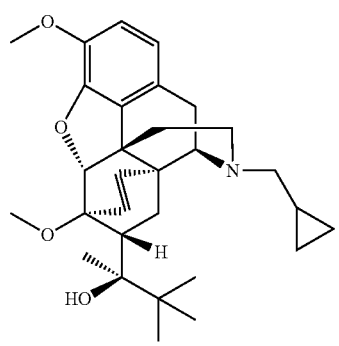

(iv)(C) reacting Compound MeO-IIIA-MCP with H₂ in the presence of a hydrogenation catalyst to provide a compound of Compound MeO-IV-MCP:

(Compound MeO-IV-MCP)

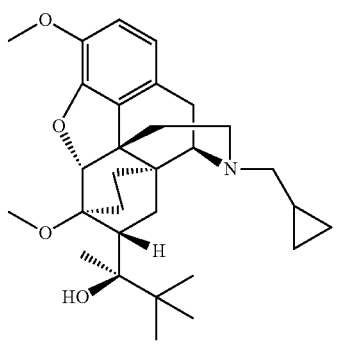

(v)(E) reacting a compound of Compound MeO-IV-MCP with a demethylating agent to provide buprenorphine; or (iii)(D) reacting Compound MeO-II-MCP with tert-butylmagnesium halide to provide Compound MeO-IIIA-MCP:

(Compound MeO-IIIA-MCP)

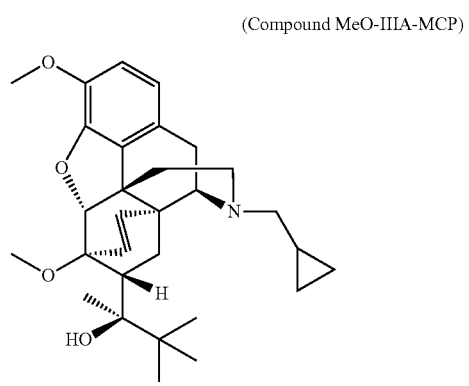 [SMILES: COc1ccc2c3c1O[C@H]1[C@@]4(OC)C=C[C@@]5(C[C@@H]4[C@](C)(O)C(C)(C)C)[C@@H](C2)N(CC2CC2)CC[C@]315]

(iv)(E) reacting Compound MeO-IIIA-MCP with a demethylating agent to provide Compound HO-IIIA-MCP:

(Compound HO-IIIA-MCP)

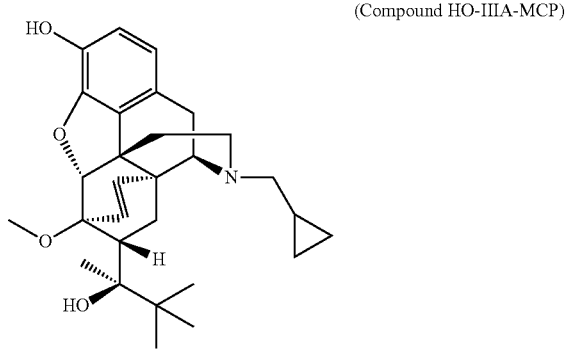 [SMILES: CO[C@]12C=C[C@@]3(C[C@@H]1[C@](C)(O)C(C)(C)C)[C@H]1Cc4ccc(O)c5c4[C@@]3(CCN1CC1CC1)[C@H]2O5]

(v)(C) reacting Compound HO-IIIA-MCP with H₂ in the presence of a hydrogenation catalyst to provide buprenorphine; or (4) from Compound HO-I-H, or a salt thereof:

(Compound HO-I-H)

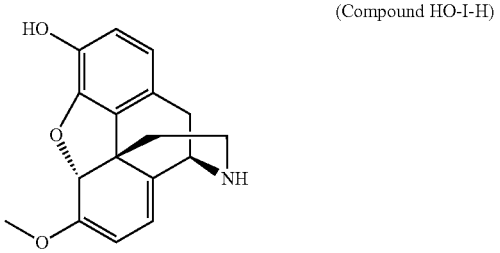 [SMILES: COC1=CC=C2[C@H]3Cc4ccc(O)c5c4[C@@]2(CCN3)[C@H]1O5]

comprising:

(i)(A1) reacting Compound HO-I-H with cyclopropane carboxaldehyde followed by a hydride source; or (i)(A2) reacting Compound HO-I-H with cyclopropanecarboxylic acid halide followed by a reducing agent; or (i)(A3) reacting Compound HO-I-H with cyclopropylmethyl halide or activated cyclopropane methanol;

to provide Compound HO-I-MCP:

(Compound HO-I-MCP)

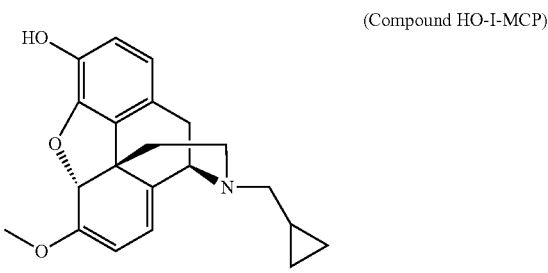 [SMILES: COC1=CC=C2[C@H]3Cc4ccc(O)c5c4[C@@]2(CCN3CC2CC2)[C@H]1O5]

and either:

(ii)(B) reacting Compound HO-I-MCP with methyl vinyl ketone to provide Compound HO-II-MCP:

(Compound HO-II-MCP)

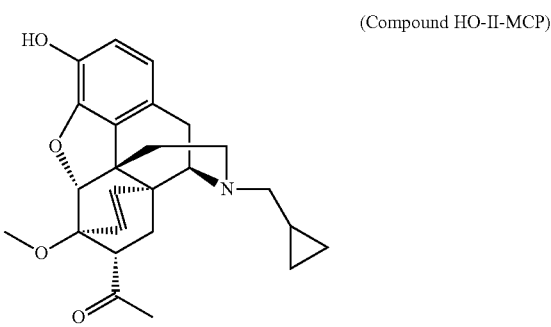 [SMILES: CO[C@]12C=C[C@@]3(C[C@@H]1C(C)=O)[C@H]1Cc4ccc(O)c5c4[C@@]3(CCN1CC1CC1)[C@H]2O5]

(iii)(F) reacting Compound HO-II-MCP with benzyl halide, benzyl sulfonate, or activated benzyl alcohol to provide Compound BnO-II-MCP:

(Compound BnO-II-MCP)

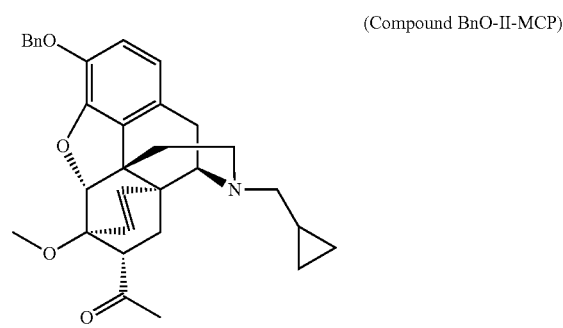 [SMILES: CO[C@]12C=C[C@@]3(C[C@@H]1C(C)=O)[C@H]1Cc4ccc(OCc5ccccc5)c5c4[C@@]3(CCN1CC1CC1)[C@H]2O5]

(iv)(D) reacting Compound BnO-II-MCP with tert-butylmagnesium halide to provide Compound BnO-IIIA-MCP:

(Compound BnO-IIIA-MCP)

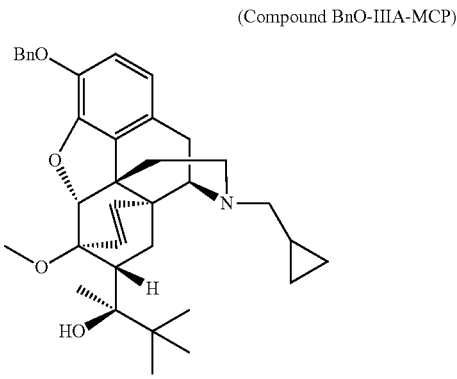 [SMILES: CO[C@]12C=C[C@@]3(C[C@@H]1[C@](C)(O)C(C)(C)C)[C@H]1Cc4ccc(OCc5ccccc5)c5c4[C@@]3(CCN1CC1CC1)[C@H]2O5]

(v)(C) reacting Compound BnO-IIIA-MCP with $H_2$ in the presence of a hydrogenation catalyst to provide buprenorphine;

or (ii)(F) reacting Compound HO-I-MCP with benzyl halide, benzyl sulfonate, or activated benzyl alcohol to provide Compound BnO-I-MCP:

(Compound BnO-I-MCP)

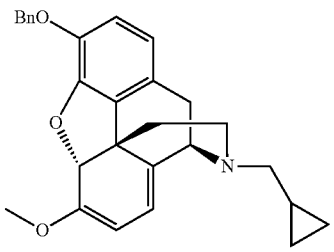

(iii)(B) reacting Compound BnO-I-MCP with methyl vinyl ketone to provide Compound BnO-II-MCP:

(Compound BnO-II-MCP)

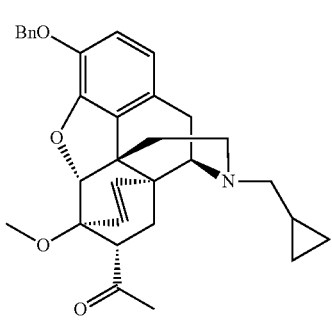

(iv)(D) reacting Compound BnO-II-MCP with tert-butyl-magnesium halide to provide Compound BnO-IIIA-MCP:

(Compound BnO-IIIA-MCP)

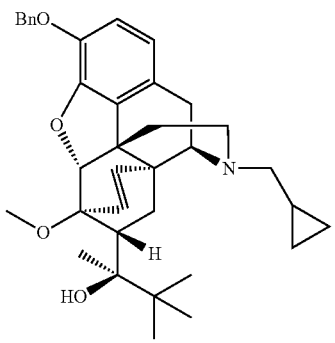

(v)(C) reacting Compound BnO-IIIA-MCP with $H_2$ in the presence of a hydrogenation catalyst to provide buprenorphine; or (5) from Compound HO-I-H, or a salt thereof:

(Compound HO-I-H)

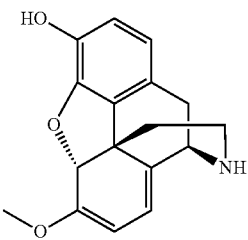

comprising:

(i)(F) reacting Compound HO-I-H with benzyl halide, benzyl sulfonate, or activated benzyl alcohol to provide Compound BnO-I-Bn:

(Compound BnO-I-Bn)

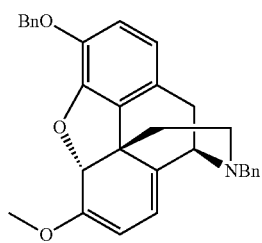

(ii)(B) reacting Compound BnO-I-Bn with methyl vinyl ketone to provide Compound BnO-II-Bn:

(Compound BnO-II-Bn)

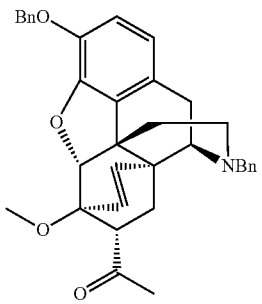

(iii)(D) reacting Compound BnO-II-Bn with tert-butyl-magnesium halide to provide Compound BnO-IIIA-Bn:

(Compound BnO-IIIA-Bn)

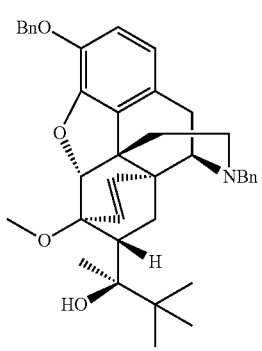

(iv)(C) reacting Compound BnO-IIIA-Bn with H$_2$ in the presence of a hydrogenation catalyst to provide a compound of Compound HO-IV-H:

(Compound HO-IV-H)

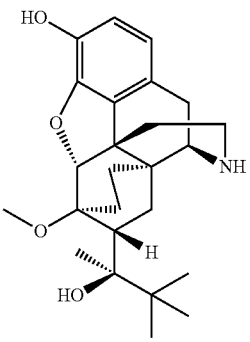

(v)(A1) reacting Compound HO-IV-H with cyclopropane carboxaldehyde followed by a hydride source; or (v)(A2) reacting Compound HO-IV-H with cyclopropanecarboxylic acid halide followed by a reducing agent; or (v)(A3) reacting Compound HO-IV-H with cyclopropylmethyl halide or activated cyclopropane methanol;

to provide buprenorphine; or (6) from Compound HO-I-H, or a salt thereof:

(Compound HO-I-H)

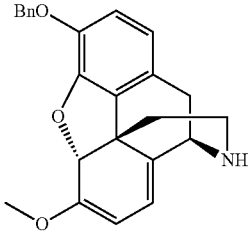

comprising:

(i)(G) reacting Compound HO-I-H with optionally substituted benzoyl halide to provide Compound HO-I-Bz:

(Compound HO-I-Bz)

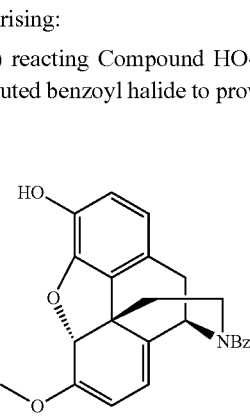

(ii)(F) reacting Compound HO-I-Bz with benzyl halide, benzyl sulfonate, or activated benzyl alcohol to provide Compound BnO-I-Bz:

(Compound BnO-I-Bz)

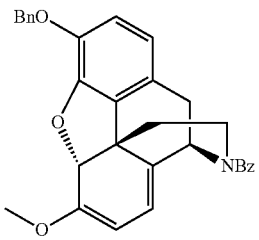

(iii)(H) reacting Compound BnO-I-Bz with lithium aluminum hydride to provide Compound BnO-I-Bn:

(Compound BnO-I-Bn)

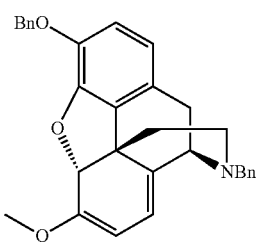

(iv)(B) reacting Compound BnO-I-Bn with methyl vinyl ketone to provide Compound BnO-II-Bn:

(Compound BnO-II-Bn)

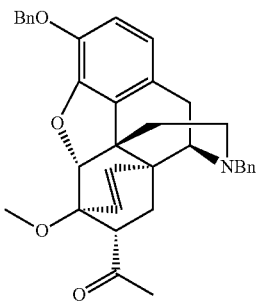

(v)(D) reacting Compound BnO-II-Bn with tert-butylmagnesium halide to provide Compound BnO-IIIA-Bn:

(Compound BnO-IIIA-Bn)

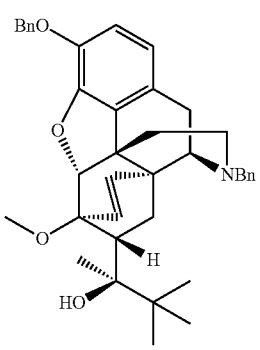

(vi)(C) reacting Compound BnO-IIIA-Bn with H$_2$ in the presence of a hydrogenation catalyst to provide a compound of Compound HO-IV-H:

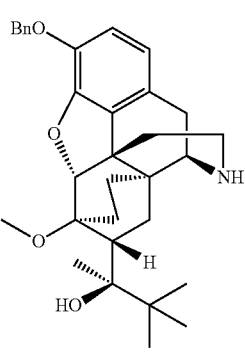
(Compound HO-IV-H)

(vii)(A1) reacting Compound HO-IV-H with cyclopropane carboxaldehyde followed by a hydride source; or (vii)(A2) reacting Compound HO-IV-H with cyclopropanecarboxylic acid halide followed by a reducing agent; or (vii)(A3) reacting Compound HO-IV-H with cyclopropylmethyl halide or activated cyclopropane methanol;

to provide buprenorphine; or (7) from Compound HO-I-H, or a salt thereof:

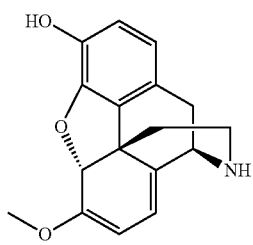
(Compound HO-I-H)

comprising:

(i)(G) reacting Compound HO-I-H with optionally substituted benzoyl halide to provide Compound BzO-I-Bz:

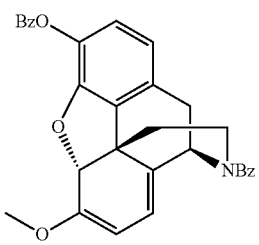
(Compound BzO-I-Bz)

(ii)(B) reacting Compound BzO-I-Bz with methyl vinyl ketone to provide Compound BzO-IIA-Bz:

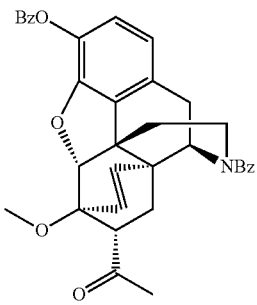
(Compound BzO-IIA-Bz)

(iii)(D) reacting Compound BzO-IIA-Bz with tert-butylmagnesium halide to provide Compound HO-IIIA-Bz:

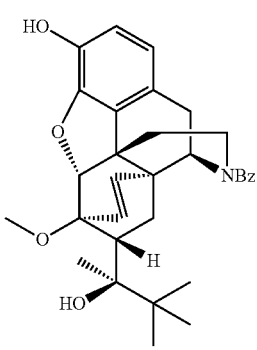
(Compound HO-IIIA-Bz)

(iv)(H) reacting Compound HO-IIIA-Bz with lithium aluminum hydride to provide Compound HO-IV-Bn:

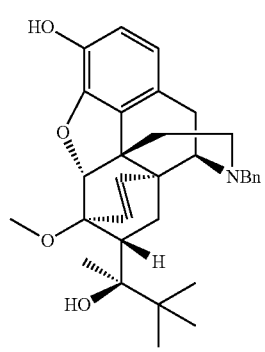
(Compound HO-IV-Bn)

(v)(C) reacting Compound HO-IV-Bn with $H_2$ in the presence of a hydrogenation catalyst to provide a compound of Compound HO-IV-H:

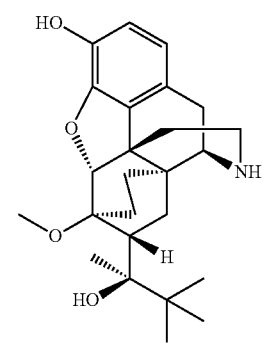
(Compound HO-IV-H)

(vi)(A1) reacting Compound HO-IV-H with cyclopropane carboxaldehyde followed by a hydride source; or (vi)(A2) reacting Compound HO-IV-H with cyclopropanecarboxylic acid halide followed by a reducing agent; or (vi)(A3) reacting Compound HO-IV-H with cyclopropylmethyl halide or activated cyclopropane methanol;

to provide buprenorphine; or (8) from Compound HO-I-H, or a salt thereof:

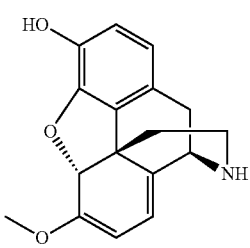

(Compound HO-I-H)

comprising:

(i)(G) reacting Compound HO-I-H with acyl halide to provide Compound AcO-I-Ac:

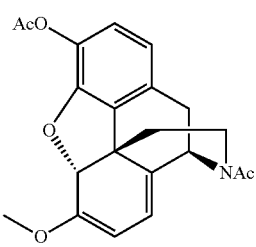

(Compound AcO-I-Ac)

(ii)(B) reacting Compound AcO-I-Ac with methyl vinyl ketone to provide Compound AcO-II-Ac:

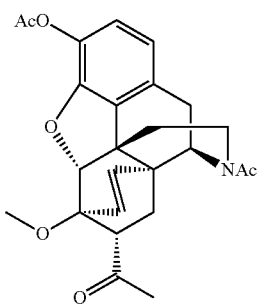

(Compound AcO-II-Ac)

and either:

(iii)(D) reacting Compound AcO-II-Ac with tert-butylmagnesium halide to provide Compound HO-IIIA-Ac:

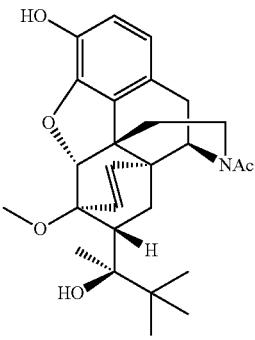

(Compound HO-IIIA-Ac)

(iv)(C) reacting Compound HO-IIIA-Ac with $H_2$ in the presence of a hydrogenation catalyst to provide a compound of Compound HO-IV-Ac:

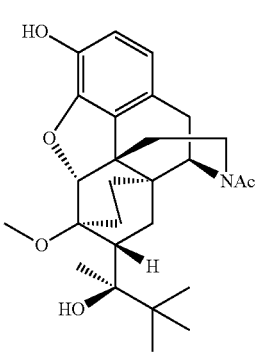

(Compound HO-IV-Ac)

(v)(I) reacting Compound HO-IV-Ac with Schwartz's reagent or base to provide Compound HO-IV-H:

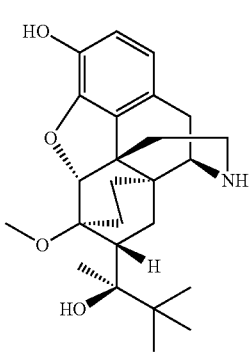

(Compound HO-IV-H)

(vi)(A1) reacting Compound HO-IV-H with cyclopropane carboxaldehyde followed by a hydride source; or (vi)(A2) reacting Compound HO-IV-H with cyclopropanecarboxylic acid halide followed by a reducing agent; or (vi)(A3) reacting Compound HO-IV-H with cyclopropylmethyl halide or activated cyclopropane methanol;

to provide buprenorphine;

or (iii)(C) reacting Compound HO-IIIA-Ac with $H_2$ in the presence of a hydrogenation catalyst to provide a compound of Compound AcO-IIIB-Ac:

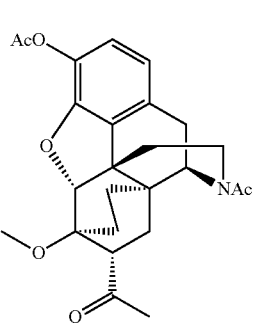
(Compound AcO-IIIB-Ac)

(iv)(D) reacting Compound AcO-IIIB-Ac with tert-butyl-magnesium halide to provide Compound HO-IV-Ac:

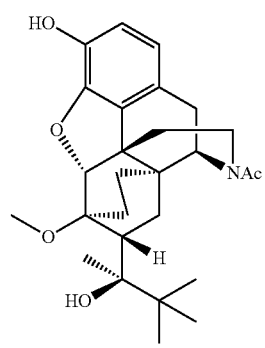
(Compound HO-IV-Ac)

(v)(I) reacting Compound HO-IV-Ac with Schwartz's reagent or base to provide Compound HO-IV-H:

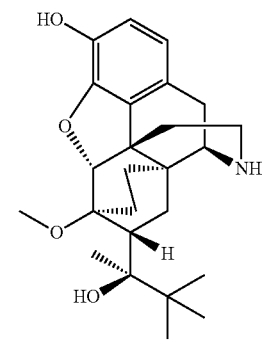
(Compound HO-IV-H)

(vi)(A1) reacting Compound HO-IV-H with cyclopropane carboxaldehyde followed by a hydride source; or (vi)(A2) reacting Compound HO-IV-H with cyclopropanecarboxylic acid halide followed by a reducing agent; or (vi)(A3) reacting Compound HO-IV-H with cyclopropylmethyl halide or activated cyclopropane methanol;

to provide buprenorphine.

2. A method according to claim 1, wherein Compound BnO-I-H is prepared from Compound HO-I-Me, or a salt thereof:

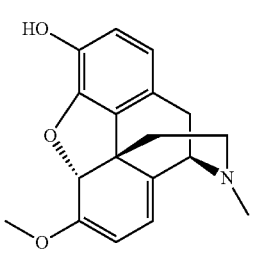
(Compound HO-I-Me)

by a method comprising:

(i)(F) reacting Compound HO-I-Me with benzyl halide, benzyl sulfonate, or activated benzyl alcohol to provide Compound BnO-I-Me:

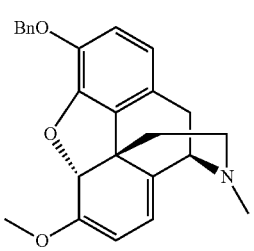
(Compound BnO-I-Me)

(ii)(E) reacting Compound BnO-I-Me with an azodicarboxylate followed by an acid or an addition salt thereof to provide Compound BnO-I-H:

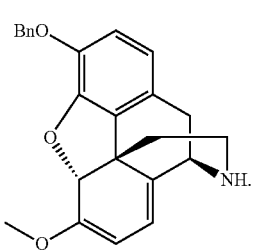
(Compound BnO-I-H)

3. A method according to claim 1, wherein the demethylating agent of step (E) is a thiolate.

4. A method according to claim 1 wherein the demethylating agent of step (E) is a dodecane thiolate.

5. A method according to claim 1, wherein step (E) is performed in a solvent comprising a polar aprotic solvent.

6. A method according to claim 1, wherein step (E) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

7. A method according to claim 1, wherein the demethylating agent of step (E) is reacted at a temperature within the range of about 50° C. to about 190° C., for a period of time within the range of about 4 hours to about 2 days.

8. A method according to claim 1, wherein the benzyl halide of step (F) in (4) is benzyl chloride or benzyl bromide.

9. A method according to claim 1, wherein step (F) in (4) is performed in the presence of a strong base.

10. A method according to claim 1, wherein step (F) in (4) is performed in the presence of an alkali metal hydride.

11. A method according to claim 1, wherein step (F) in (4) is performed in a solvent comprising a polar aprotic solvent.

12. A method according to claim 1, wherein step (F) in (4) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

13. A method according to claim 2, wherein the benzyl halide of step (F) in (4) is benzyl chloride or benzyl bromide.

14. A method according to claim 2, wherein step (F) is performed in the presence of a strong base.

15. A method according to claim 2, wherein step (F) is performed in the presence of an alkali metal hydride.

16. A method according to claim 2, wherein step (F) is performed in a solvent comprising a polar aprotic solvent.

17. A method according to claim 2, wherein step (F) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

\* \* \* \* \*